(12) United States Patent
Shah

(10) Patent No.: US 12,404,519 B2
(45) Date of Patent: *Sep. 2, 2025

(54) ANTIFUNGAL PLANT PROTEINS, PEPTIDES, AND METHODS OF USE

(71) Applicant: Donald Danforth Plant Science Center, St. Louis, MO (US)

(72) Inventor: Dilip Shah, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/336,772

(22) Filed: Jun. 16, 2023

(65) Prior Publication Data
US 2023/0392161 A1 Dec. 7, 2023

Related U.S. Application Data

(60) Continuation of application No. 17/304,156, filed on Jun. 15, 2021, now abandoned, which is a continuation of application No. 16/277,157, filed on Feb. 15, 2019, now abandoned, which is a division of application No. 14/888,011, filed as application No. PCT/US2014/035786 on Apr. 29, 2014, now Pat. No. 10,253,328.

(60) Provisional application No. 61/817,415, filed on Apr. 30, 2013.

(51) Int. Cl.
| | |
|---|---|
| *A01H 5/00* | (2018.01) |
| *A01H 1/00* | (2006.01) |
| *A01N 65/20* | (2009.01) |
| *C07H 21/04* | (2006.01) |
| *C07K 14/415* | (2006.01) |
| *C12N 15/00* | (2006.01) |
| *C12N 15/82* | (2006.01) |

(52) U.S. Cl.
CPC ....... *C12N 15/8282* (2013.01); *A01H 1/1255* (2021.01); *A01H 5/00* (2013.01); *A01N 65/20* (2013.01); *C07H 21/04* (2013.01); *C07K 14/415* (2013.01); *C12N 15/00* (2013.01)

(58) Field of Classification Search
None
See application file for complete search history.

(56) References Cited

U.S. PATENT DOCUMENTS

| | | | |
|---|---|---|---|
| 4,546,082 A | 10/1985 | Kurjan et al. | |
| 4,588,684 A | 5/1986 | Brake | |
| 4,855,231 A | 8/1989 | Stroman et al. | |
| 4,870,008 A | 9/1989 | Brake | |
| 5,004,863 A | 4/1991 | Umbeck | |
| 5,229,112 A | 7/1993 | Obukowicz et al. | |
| 5,389,525 A | 2/1995 | Hollenberg et al. | |
| 5,424,412 A | 6/1995 | Brown et al. | |
| 5,500,365 A | 3/1996 | Fischhoff et al. | |
| 5,538,525 A | 7/1996 | Broekaert et al. | |
| 5,602,034 A | 2/1997 | Tekamp-Olson | |
| 5,689,052 A | 11/1997 | Brown et al. | |
| 5,741,672 A | 4/1998 | Ledeboer et al. | |
| 6,365,807 B1 | 4/2002 | Christou et al. | |
| 6,596,925 B1 | 7/2003 | Perera et al. | |
| 6,602,682 B1 | 8/2003 | Van Den Berg et al. | |
| 6,916,970 B2 | 7/2005 | Liang et al. | |
| 6,972,197 B1 | 12/2005 | Preuss et al. | |
| 7,002,058 B2 | 2/2006 | Martinell et al. | |
| 7,102,055 B1 | 9/2006 | Baszczynski et al. | |
| 7,825,297 B2 | 11/2010 | Shah et al. | |
| 8,163,979 B2 | 4/2012 | Shah et al. | |
| 8,558,057 B2 | 10/2013 | Shah et al. | |
| 2002/0115849 A1 | 8/2002 | Pryor et al. | |
| 2005/0289673 A1 | 12/2005 | Armstrong et al. | |
| 2006/0026710 A1 | 2/2006 | Ali et al. | |
| 2009/0197809 A1 | 8/2009 | Anderson et al. | |
| 2012/0108422 A1 | 5/2012 | Renner et al. | |
| 2012/0180160 A1 | 7/2012 | Shah et al. | |

FOREIGN PATENT DOCUMENTS

| | | |
|---|---|---|
| EP | 0392225 A2 | 10/1990 |
| WO | 2012012480 A2 | 1/2012 |

OTHER PUBLICATIONS

Abdallah et al., "Stable Integration and Expression of a Plant Defensin in Tomato Confers Resistance to Fusarium Wilt", GM Crops, vol. 1, Issue 5, pp. 344-350, Nov. 16, 2010.
European Patent Office, "Extended European Search Report", issued in connection to Application No. 14792240.5, 6 pages, Dec. 9, 2016.
Hanks et al., "Defensin Gene Family in Medicago Truncatula: Structure, Expression and Induction by Signal Molecules", Plant Molecular Biology, vol. 58, No. 3, pp. 385-399, Jun. 1, 2005.
Islam et al., "A novel bi-domain plant defensin MtDef5 with potent broad-spectrum antifungal activity binds to multiple phospholipids and forms oligomers", Scientific Reports, vol. 7, No. 16157, 1 page, Nov. 23, 2017.

(Continued)

*Primary Examiner* — Phuong T Bui
(74) *Attorney, Agent, or Firm* — McKee, Voorhees & Sease, PLC

(57) ABSTRACT

Provided are transgenic plants expressing MtDef5 antifungal proteins and peptides exhibiting high levels of resistance to susceptible fungi. Such transgenic plants contain a recombinant DNA construct comprising a natural or heterologous signal peptide sequence operably linked to a nucleic acid sequence encoding these molecules. Also provided are methods of producing such plants, methods of protecting plants against susceptible fungal infection and damage, as well as compositions that can be applied to the locus of plants, comprising microorganisms expressing these molecules, or these molecules themselves, as well as pharmaceutical compositions containing these molecules. Human and veterinary therapeutic use of MtDef5 antifungal proteins and peptides to treat susceptible fungal infections are also encompassed by the invention.

8 Claims, 2 Drawing Sheets
Specification includes a Sequence Listing.

(56) References Cited

OTHER PUBLICATIONS

Lay et al., "Defensins-components of the innate immune system in plants", Current Protein and Peptide Science, vol. 6, No. 1, pp. 85-101, Feb. 2005.

International Searching Authority in connection with PCT/US2014/035786 filed Apr. 29, 2014, "Written Opinion of the International Searching Authority", 11 pages, Jan. 4, 2016.

International Search Report in connection with PCT/US2014/035786 filed Apr. 29, 2014, 4 pages, mailed Jan. 4, 2016.

Sagaram et al., "Structure-Activity Determinants in Antifungal Plant Defensins MsDef1 and MtDef4 with Different Modes of Action against Fusarium graminearum", PLoS One, vol. 6, Issue 4, e18550, pp. 1-13, Apr. 13, 2011.

Silverstein et al., "Genome Organization of More Than 300 Defensin-Like Genes in Arabidopsis", Plant Physiology, vol. 138, Issue 2, pp. 600-610, Jun. 2005.

Thomma et al., "Plant Defensins", Planta, vol. 216, No. 2, pp. 193-202, Dec. 2002.

Verdoy et al., "Transgenic Medicago truncatula plants that accumulate proline display nitrogen-fixing activity with enhanced tolerance to osmotic stress", Plant Cell Environment, vol. 29, No. 10, pp. 1913-1923, Oct. 2006.

Young et al., "The Medicago genome provides insight into the evolution of rhizobial symbioses", Nature, vol. 480, pp. 520-524, 2011.

SEQUENCE LISTING

```
Sequence total quantity: 81
SEQ ID NO: 1            moltype = AA  length = 136
FEATURE                 Location/Qualifiers
source                  1..136
                        mol_type = protein
                        note = wild-type sequence from Medicago truncatula
                        organism = synthetic construct
SEQUENCE: 1
MTSSASKFYT IFIFVCLAFL FISTSEVEAK LCQKRSTTWS GPCLNTGNCK RQCINVEHAT   60
FGACHRQGFG FACFCYKKCA PKKVEPKLCE RRSKTWSGPC LISGNCKRQC INVEHATSGA  120
CHRQGIGFAC FCKKKC                                                  136

SEQ ID NO: 2            moltype = AA  length = 7
FEATURE                 Location/Qualifiers
source                  1..7
                        mol_type = protein
                        organism = Medicago truncatula
SEQUENCE: 2
APKKVEP                                                              7

SEQ ID NO: 3            moltype = AA  length = 78
FEATURE                 Location/Qualifiers
source                  1..78
                        mol_type = protein
                        organism = Medicago truncatula
SEQUENCE: 3
MASSSPKLFT IFLFLILVVL LFSTSEVQAK LCRGRSKLWS GPCINSKCKR QCINVERAVS   60
GGCHLDNTGV FCFCDFKC                                                 78

SEQ ID NO: 4            moltype = AA  length = 136
FEATURE                 Location/Qualifiers
source                  1..136
                        mol_type = protein
                        organism = Medicago truncatula
SEQUENCE: 4
MTSSASKFYT IFIFVCLAFL FISTSEVEAK LCQKRSTTWS GPCLNTGNCK RQCINVEHAT   60
FGACHRQGFG FACFCYKKCA PKKVEPKLCE RRSKTWSGPC LISGNCKRQC INVEHATSGA  120
CHRQGIGFAC FCKKKC                                                  136

SEQ ID NO: 5            moltype = AA  length = 78
FEATURE                 Location/Qualifiers
```

```
source                  1..78
                        mol_type = protein
                        note = wild-type sequence from Medicago truncatula
                        organism = synthetic construct
SEQUENCE: 5
MASSSPKLFT IFLFLILVVL LFSTSEVQAK LCRGRSKLWS GPCINSKCKR QCINVERAVS    60
GGCHLDNTGV FCFCDFKC                                                 78

SEQ ID NO: 6            moltype = AA  length = 79
FEATURE                 Location/Qualifiers
source                  1..79
                        mol_type = protein
                        note = wild-type sequence from Medicago truncatula
                        organism = synthetic construct
SEQUENCE: 6
MTSSATKFYT IFVFVCLALL LISICEVEAK VCQKRSKTWS GPCLNTGNCK RQCVDVENAT    60
FGACHRQGYG FACFCYKKC                                                79

SEQ ID NO: 7            moltype = AA  length = 79
FEATURE                 Location/Qualifiers
source                  1..79
                        mol_type = protein
                        note = wild-type sequence from Medicago truncatula
                        organism = synthetic construct
SEQUENCE: 7
MASSTLKFNT IFLFLSLALL LFFTLEVQGN ICKRKSTTWS GPCLNTGNCK NQCINVEHAT    60
FGACHQDGFG FACFCYFNC                                                79

SEQ ID NO: 8            moltype = AA  length = 80
FEATURE                 Location/Qualifiers
source                  1..80
                        mol_type = protein
                        note = wild-type sequence from Medicago truncatula
                        organism = synthetic construct
SEQUENCE: 8
MASSALKYYT FFLFFILALI LLPTLEVQGN TCQRKSKTWS GPCLNTANCK NQCISKEPPA    60
TFGACHRDGI GFACFCYFNC                                               80

SEQ ID NO: 9            moltype = AA  length = 57
FEATURE                 Location/Qualifiers
source                  1..57
                        mol_type = protein
                        note = wild-type sequence from Medicago truncatula
                        organism = synthetic construct
SEQUENCE: 9
MVCTEVQAKL CRGRSKLWSG PCINSKCKRQ CINVERAVSG GCHLDNTGVF CFCDFKC       57

SEQ ID NO: 10           moltype = DNA  length = 411
FEATURE                 Location/Qualifiers
source                  1..411
                        mol_type = other DNA
                        organism = synthetic construct
CDS                     1..411
                        note = encodes wild-type protein from Medicago truncatula
                        protein_id = 1
                        translation = MTSSASKFYTIFIFVCLAFLFISTSEVEAKLCQKRSTTWSGPCLNT
                        GNCKRQCINVEHATFGACHRQGFGFACFCYKKCAPKKVEPKLCERRSKTWSGPCLISGN
                        CKRQCINVEHATSGACHRQGIGFACFCKKKC
SEQUENCE: 10
atgacttcct ctgctagtaa attctatacc atcttcattt ttgtctgcct tgcctttctc    60
tttatttcca catctgaggt ggaagcaaaa ctttgtcaaa agcgaagtac aacatgtca   120
ggaccttgtc ttaacacagg aaactgcaaa agacaatgca ttaatgtgga gcatgctact  180
tttggtgctt gtcatcgtca aggctttggt tttgcttgct ctgctacaa aaaatgtgct   240
ccaaagaagg tggaacctaa actttgtgaa aggcgaagca aaacttggtc aggaccttgt  300
cttatctcag gaaattgtaa aagacagtgc atcaatgttg agcatgcaac ttctggtgct  360
tgtcaccgtc aaggcattgg ttttgcttgc ttctgcaaga aaaaatgttg a           411

SEQ ID NO: 11           moltype = DNA  length = 237
FEATURE                 Location/Qualifiers
source                  1..237
                        mol_type = other DNA
                        organism = synthetic construct
CDS                     1..237
                        note = encodes wild-type protein from Medicago truncatula
                        protein_id = 5
                        translation = MASSSPKLFTIFLFLILVVLLFSTSEVQAKLCRGRSKLWSGPCINS
                        KCKRQCINVERAVSGGCHLDNTGVFCFCDFKC
SEQUENCE: 11
atggcttcct cttctcctaa attgtttacc atctttctgt ttctcatcct tgtcgtgctc    60
```

```
ctttttctcaa cttcggaggt gcaagcaaaa ctttgtagag ggagaagcaa actttggtca   120
gggccttgta ttaactcaaa atgcaaagac aatgcatca acgtggagcg cgcagttagc   180
ggggggttgtc accttgataa cactggagtt tttgtttct gcgacttcaa atgctga   237
```

```
SEQ ID NO: 12              moltype = DNA   length = 240
FEATURE                    Location/Qualifiers
source                     1..240
                           mol_type = other DNA
                           organism = synthetic construct
CDS                        1..240
                           note = encodes wild-type protein from Medicago truncatula
                           protein_id = 6
                           translation = MTSSATKFYTIFVFVCLALLLISICEVEAKVCQKRSKTWSGPCLNT
                           GNCKRQCVDVENATFGACHRQGYGFACFCYKKC
SEQUENCE: 12
atgacttcct ctgctactaa attttacacc atctttgttt ttgtctgcct tgcccttctc   60
cttatttcca tatgtgaggt ggaagcaaaa gtgtgtcaaa aacgaagtaa aacgtggtca   120
ggaccttgtc ttaacacagg aaactgtaaa agacaatgcg ttgatgtgga gaatgcaacc   180
ttcggtgctt gtcaccgtca aggctatggt tttgcttgct tctgctacaa aaagtgttga   240
```

```
SEQ ID NO: 13              moltype = DNA   length = 240
FEATURE                    Location/Qualifiers
source                     1..240
                           mol_type = other DNA
                           organism = synthetic construct
CDS                        1..240
                           note = encodes wild-type protein from Medicago truncatula
                           protein_id = 7
                           translation = MASSTLKFNTIFLFLSLALLLFFTLEVQGNICKRKSTTWSGPCLNT
                           GNCKNQCINVEHATFGACHQDGFGFACFCYFNC
SEQUENCE: 13
atggcttcat ctactcttaa attcaacact atctttctgt ttctcagcct tgcacttctc   60
ctgttcttca cattggaggt acaaggaaat atttgtaaaa ggaaaagcac aacatggtca   120
gggccatgtt taaacacggg aaactgtaaa aatcagtgca tcaatgtgga acatgctact   180
tttgggcat gccaccaaga tggatttgga tttgcttgct tctgctactt caattgctga   240
```

```
SEQ ID NO: 14              moltype = DNA   length = 243
FEATURE                    Location/Qualifiers
source                     1..243
                           mol_type = other DNA
                           organism = synthetic construct
CDS                        1..243
                           note = encodes wild-type protein from Medicago truncatula
                           protein_id = 8
                           translation = MASSALKYYTFFLFFILALILLPTLEVQGNTCQRKSKTWSGPCLNT
                           ANCKNQCISKEPPATFGACHRDGIGFACFCYFNC
SEQUENCE: 14
atggcttcct ctgctcttaa atactacact ttctttctgt ttttcatcct tgcacttatc   60
ctgttaccca cattggaggt acaaggaaat acttgtcaaa ggaaaagcaa aacatggtca   120
gggccatgtt taaacacggc aaactgtaaa aatcagtgca tcagtaagga accaccggca   180
acatttgggg catgtcaccg tgatggcatt ggatttgctt gctctgttta cttcaactgc   240
taa                                                                  243
```

```
SEQ ID NO: 15              moltype = DNA   length = 174
FEATURE                    Location/Qualifiers
source                     1..174
                           mol_type = other DNA
                           organism = synthetic construct
CDS                        1..174
                           note = encodes wild-type protein from Medicago truncatula
                           protein_id = 9
                           translation = MVCTEVQAKLCRGRSKLWSGPCINSKCKRQCINVERAVSGGCHLDN
                           TGVFCFCDFKC
SEQUENCE: 15
atggtgtgta cagaggtgca agcaaaactt tgtagaggga gaagcaaact ttggtcaggg   60
ccttgtatta actcaaaatg caaaagacaa tgcatcaacg tggagcgcgc agttagcggg   120
ggttgtcacc ttgataacac tggagttttt gtttctgcg acttcaaatg ctga          174
```

```
SEQ ID NO: 16              moltype = AA   length = 50
FEATURE                    Location/Qualifiers
source                     1..50
                           mol_type = protein
                           note = wild-type sequence from Medicago truncatula
                           organism = synthetic construct
SEQUENCE: 16
KLCQKRSTTW SGPCLNTGNC KRQCINVEHA TFGACHRQGF GFACFCYKKC               50
```

```
SEQ ID NO: 17              moltype = AA   length = 50
FEATURE                    Location/Qualifiers
```

```
source                  1..50
                        mol_type = protein
                        note = wild-type sequence from Medicago truncatula
                        organism = synthetic construct
SEQUENCE: 17
KLCERRSKTW SGPCLISGNC KRQCINVEHA TSGACHRQGI GFACFCKKKC            50

SEQ ID NO: 18           moltype = AA  length = 49
FEATURE                 Location/Qualifiers
source                  1..49
                        mol_type = protein
                        note = wild-type sequence from Medicago truncatula
                        organism = synthetic construct
SEQUENCE: 18
KLCRGRSKLW SGPCINSKCK RQCINVERAV SGGCHLDNTG VFCFCDFKC             49

SEQ ID NO: 19           moltype = AA  length = 50
FEATURE                 Location/Qualifiers
source                  1..50
                        mol_type = protein
                        note = wild-type sequence from Medicago truncatula
                        organism = synthetic construct
SEQUENCE: 19
KVCQKRSKTW SGPCLNTGNC KRQCVDVENA TFGACHRQGY GFACFCYKKC            50

SEQ ID NO: 20           moltype = AA  length = 50
FEATURE                 Location/Qualifiers
source                  1..50
                        mol_type = protein
                        note = wild-type sequence from Medicago truncatula
                        organism = synthetic construct
SEQUENCE: 20
NICKRKSTTW SGPCLNTGNC KNQCINVEHA TFGACHQDGF GFACFCYFNC            50

SEQ ID NO: 21           moltype = AA  length = 51
FEATURE                 Location/Qualifiers
source                  1..51
                        mol_type = protein
                        note = wild-type sequence from Medicago truncatula
                        organism = synthetic construct
SEQUENCE: 21
NTCQRKSKTW SGPCLNTANC KNQCISKEPP ATFGACHRDG IGFACFCYFN C          51

SEQ ID NO: 22           moltype = AA  length = 49
FEATURE                 Location/Qualifiers
source                  1..49
                        mol_type = protein
                        note = wild-type sequence from Medicago truncatula
                        organism = synthetic construct
SEQUENCE: 22
KLCRGRSKLW SGPCINSKCK RQCINVERAV SGGCHLDNTG VFCFCDFKC             49

SEQ ID NO: 23           moltype = DNA  length = 150
FEATURE                 Location/Qualifiers
source                  1..150
                        mol_type = other DNA
                        organism = synthetic construct
CDS                     150
                        note = encodes wild-type protein from Medicago truncatula
                        protein_id = 16
                        translation = KLCQKRSTTWSGPCLNTGNCKRQCINVEHATFGACHRQGFGFACFC
                         YKKC
SEQUENCE: 23
aaactttgtc aaaagcgaag tacaacatgg tcaggacctt gtcttaacac aggaaactgc   60
aaaagacaat gcattaatgt ggagcatgct acttttggtg cttgtcatcg tcaaggcttt  120
ggttttgctt gcttctgcta caaaaaatgt                                   150

SEQ ID NO: 24           moltype = DNA  length = 150
FEATURE                 Location/Qualifiers
source                  1..150
                        mol_type = other DNA
                        organism = synthetic construct
CDS                     150
                        note = encodes wild-type protein from Medicago truncatula
                        protein_id = 17
                        translation = KLCERRSKTWSGPCLISGNCKRQCINVEHATSGACHRQGIGFACFC
                         KKKC
SEQUENCE: 24
aaactttgtg aaaggcgaag caaaacatgg tcaggacctt gtcttatctc aggaaattgt   60
```

```
aaaagacagt gcatcaatgt tgagcatgca acttctggtg cttgtcaccg tcaaggcatt    120
ggttttgctt gcttctgcaa gaaaaaatgt                                     150
```

| SEQ ID NO: 25 | moltype = DNA  length = 147 |
|---|---|
| FEATURE | Location/Qualifiers |
| source | 1..147 |
|  | mol_type = other DNA |
|  | organism = synthetic construct |
| CDS | 147 |
|  | note = encodes wild-type protein from Medicago truncatula |
|  | protein_id = 18 |
|  | translation = KLCRGRSKLWSGPCINSKCKRQCINVERAVSGGCHLDNTGVFCFCD |
|  | FKC |

SEQUENCE: 25
```
aaactttgta gagggagaag caaactttgg tcaggcctt gtattaactc aaaatgcaaa    60
agacaatgca tcaacgtgga gcgcgcagtt agcgggggtt gtcaccttga taacactgga   120
gttttttgtt tctgcgactt caaatgc                                       147
```

| SEQ ID NO: 26 | moltype = DNA  length = 150 |
|---|---|
| FEATURE | Location/Qualifiers |
| source | 1..150 |
|  | mol_type = other DNA |
|  | organism = synthetic construct |
| CDS | 150 |
|  | note = encodes wild-type protein from Medicago truncatula |
|  | protein_id = 19 |
|  | translation = KVCQKRSKTWSGPCLNTGNCKRQCVDVENATFGACHRQGYGFACFC |
|  | YKKC |

SEQUENCE: 26
```
aaagtgtgtc aaaaacgaag taaaacgtgg tcaggaccctt gtcttaacac aggaaactgt   60
aaaagacaat gcgttgatgt ggagaatgca accttcggtg cttgtcaccg tcaaggctat   120
ggttttgctt gcttctgcta caaaaagtgt                                    150
```

| SEQ ID NO: 27 | moltype = DNA  length = 150 |
|---|---|
| FEATURE | Location/Qualifiers |
| source | 1..150 |
|  | mol_type = other DNA |
|  | organism = synthetic construct |
| CDS | 150 |
|  | note = encodes wild-type protein from Medicago truncatula |
|  | protein_id = 20 |
|  | translation = NICKRKSTTWSGPCLNTGNCKNQCINVEHATFGACHQDGFGFACFC |
|  | YFNC |

SEQUENCE: 27
```
aatatttgta aaaggaaaag cacaacatgg tcagggccat gtttaaacac gggaaactgt   60
aaaaatcagt gcatcaatgt ggaacatgct acttttgggg catgccacca agatggattt   120
ggatttgctt gcttctgcta cttcaattgc                                    150
```

| SEQ ID NO: 28 | moltype = DNA  length = 153 |
|---|---|
| FEATURE | Location/Qualifiers |
| source | 1..153 |
|  | mol_type = other DNA |
|  | organism = synthetic construct |
| CDS | 153 |
|  | note = encodes wild-type protein from Medicago truncatula |
|  | protein_id = 21 |
|  | translation = NTCQRKSKTWSGPCLNTANCKNQCISKEPPATFGACHRDGIGFACF |
|  | CYFNC |

SEQUENCE: 28
```
aatacttgtc aaaggaaaag caaaacatgg tcagggccat gtttaaacac ggcaaactgt   60
aaaaatcagt gcatcagtaa ggaaccaccg gcaacatttg gggcatgtca ccgtgatggc   120
attggatttg cttgcttctg ttacttcaac tgc                                153
```

| SEQ ID NO: 29 | moltype = DNA  length = 147 |
|---|---|
| FEATURE | Location/Qualifiers |
| source | 1..147 |
|  | mol_type = other DNA |
|  | organism = synthetic construct |
| CDS | 147 |
|  | note = encodes wild-type protein from Medicago truncatula |
|  | protein_id = 22 |
|  | translation = KLCRGRSKLWSGPCINSKCKRQCINVERAVSGGCHLDNTGVFCFCD |
|  | FKC |

SEQUENCE: 29
```
aaactttgta gagggagaag caaactttgg tcaggcctt gtattaactc aaaatgcaaa    60
agacaatgca tcaacgtgga gcgcgcagtt agcgggggtt gtcaccttga taacactgga   120
gttttttgtt tctgcgactt caaatgc                                       147
```

| SEQ ID NO: 30 | moltype = AA  length = 29 |
|---|---|

| FEATURE | Location/Qualifiers |
|---|---|
| source | 1..29 |
| | mol_type = protein |
| | note = wild-type sequence from Medicago truncatula |
| | organism = synthetic construct |

SEQUENCE: 30
MTSSASKFYT IFIFVCLAFL FISTSEVEA                                      29

| SEQ ID NO: 31 | moltype = AA   length = 29 |
|---|---|
| FEATURE | Location/Qualifiers |
| source | 1..29 |
| | mol_type = protein |
| | note = wild-type sequence from Medicago truncatula |
| | organism = synthetic construct |

SEQUENCE: 31
MASSSPKLFT IFLFLILVVL LFSTSEVQA                                      29

| SEQ ID NO: 32 | moltype = AA   length = 29 |
|---|---|
| FEATURE | Location/Qualifiers |
| source | 1..29 |
| | mol_type = protein |
| | note = wild-type sequence from Medicago truncatula |
| | organism = synthetic construct |

SEQUENCE: 32
MTSSATKFYT IFVFVCLALL LISICEVEA                                      29

| SEQ ID NO: 33 | moltype = AA   length = 29 |
|---|---|
| FEATURE | Location/Qualifiers |
| source | 1..29 |
| | mol_type = protein |
| | note = wild-type sequence from Medicago truncatula |
| | organism = synthetic construct |

SEQUENCE: 33
MASSTLKFNT IFLFLSLALL LFFTLEVQG                                      29

| SEQ ID NO: 34 | moltype = AA   length = 29 |
|---|---|
| FEATURE | Location/Qualifiers |
| source | 1..29 |
| | mol_type = protein |
| | note = wild-type sequence from Medicago truncatula |
| | organism = synthetic construct |

SEQUENCE: 34
MASSALKYYT FFLFFILALI LLPTLEVQG                                      29

| SEQ ID NO: 35 | moltype = AA   length = 8 |
|---|---|
| FEATURE | Location/Qualifiers |
| source | 1..8 |
| | mol_type = protein |
| | note = wild-type sequence from Medicago truncatula |
| | organism = synthetic construct |

SEQUENCE: 35
MVCTEVQA                                                              8

| SEQ ID NO: 36 | moltype = DNA   length = 87 |
|---|---|
| FEATURE | Location/Qualifiers |
| source | 1..87 |
| | mol_type = other DNA |
| | organism = synthetic construct |
| CDS | 1..87 |
| | note = encodes wild-type peptide from Medicago truncatula |
| | protein_id = 30 |
| | translation = MTSSASKFYTIFIFVCLAFLFISTSEVEA |

SEQUENCE: 36
atgacttcct ctgctagtaa attctatacc atcttcattt ttgtctgcct tgcctttctc   60
tttatttcca catctgaggt ggaagca                                        87

| SEQ ID NO: 37 | moltype = DNA   length = 87 |
|---|---|
| FEATURE | Location/Qualifiers |
| source | 1..87 |
| | mol_type = other DNA |
| | organism = synthetic construct |
| CDS | 1..87 |
| | note = encodes wild-type peptide from Medicago truncatula |
| | protein_id = 31 |
| | translation = MASSSPKLFTIFLFLILVVLLFSTSEVQA |

SEQUENCE: 37
atggcttcct cttctcctaa attgtttacc atctttctgt ttctcatcct tgtcgtgctc   60
cttttctcaa cttcggaggt gcaagca                                        87

| SEQ ID NO: 38 | moltype = DNA  length = 87 |
| --- | --- |
| FEATURE | Location/Qualifiers |
| source | 1..87 |
|  | mol_type = other DNA |
|  | organism = synthetic construct |
| CDS | 1..87 |
|  | note = encodes wild-type peptide from Medicago truncatula |
|  | protein_id = 32 |
|  | translation = MTSSATKFYTIFVFVCLALLLISICEVEA |

SEQUENCE: 38
atgacttcct ctgctactaa attttacacc atctttgttt ttgtctgcct tgcccttctc 60
cttatttcca tatgtgaggt ggaagca 87

| SEQ ID NO: 39 | moltype = DNA  length = 87 |
| --- | --- |
| FEATURE | Location/Qualifiers |
| source | 1..87 |
|  | mol_type = other DNA |
|  | organism = synthetic construct |
| CDS | 1..87 |
|  | note = encodes wild-type peptide from Medicago truncatula |
|  | protein_id = 33 |
|  | translation = MASSTLKFNTIFLFLSLALLLFFTLEVQG |

SEQUENCE: 39
atggcttcat ctactcttaa attcaacact atctttctgt ttctcagcct tgcacttctc 60
ctgttcttca cattggaggt acaagga 87

| SEQ ID NO: 40 | moltype = DNA  length = 87 |
| --- | --- |
| FEATURE | Location/Qualifiers |
| source | 1..87 |
|  | mol_type = other DNA |
|  | organism = synthetic construct |
| CDS | 1..87 |
|  | note = encodes wild-type peptide from Medicago truncatula |
|  | protein_id = 34 |
|  | translation = MASSALKYYTFFLFFILALILLPTLEVQG |

SEQUENCE: 40
atggcttcct ctgctcttaa atactacact ttctttctgt ttttcatcct tgcacttatc 60
ctgttaccca cattggaggt acaagga 87

| SEQ ID NO: 41 | moltype = DNA  length = 24 |
| --- | --- |
| FEATURE | Location/Qualifiers |
| source | 1..24 |
|  | mol_type = other DNA |
|  | organism = synthetic construct |
| CDS | 1..24 |
|  | note = encodes wild-type peptide from Medicago truncatula |
|  | protein_id = 35 |
|  | translation = MVCTEVQA |

SEQUENCE: 41
atggtgtgta cagaggtgca agca 24

| SEQ ID NO: 42 | moltype = AA  length = 29 |
| --- | --- |
| FEATURE | Location/Qualifiers |
| source | 1..29 |
|  | mol_type = protein |
|  | organism = Medicago truncatula |

SEQUENCE: 42
MARSVPLVST IFVFLLLLVA TGPSMVAEA 29

| SEQ ID NO: 43 | moltype = AA  length = 30 |
| --- | --- |
| FEATURE | Location/Qualifiers |
| source | 1..30 |
|  | mol_type = protein |
|  | organism = Medicago truncatula |

SEQUENCE: 43
MARSVPLVST IFVFFLLIVA TEMGPSMVAA 30

| SEQ ID NO: 44 | moltype = AA  length = 31 |
| --- | --- |
| FEATURE | Location/Qualifiers |
| source | 1..31 |
|  | mol_type = protein |
|  | organism = Medicago truncatula |

SEQUENCE: 44
MARSVPLVST IFVFFLLLVA TEMGPIMVAE A 31

| SEQ ID NO: 45 | moltype = AA  length = 29 |
| --- | --- |
| FEATURE | Location/Qualifiers |
| source | 1..29 |
|  | mol_type = protein |

```
                          organism = Medicago truncatula
SEQUENCE: 45
MARSVFLVST IFVFLLVLVA TGPSMVAEA                                              29

SEQ ID NO: 46             moltype = AA  length = 29
FEATURE                   Location/Qualifiers
source                    1..29
                          mol_type = protein
                          organism = Medicago truncatula
SEQUENCE: 46
MARSVSLVFT IFVFLLLVVA TGPSMVAEA                                              29

SEQ ID NO: 47             moltype = AA  length = 29
FEATURE                   Location/Qualifiers
source                    1..29
                          mol_type = protein
                          organism = Medicago truncatula
SEQUENCE: 47
MARSVPLVST IFVFLLLLVA TGPSMVGEA                                              29

SEQ ID NO: 48             moltype = AA  length = 29
FEATURE                   Location/Qualifiers
source                    1..29
                          mol_type = protein
                          organism = Medicago truncatula
SEQUENCE: 48
MARSVPLVST IFVFLLLLVA TGPSMVAEA                                              29

SEQ ID NO: 49             moltype = AA  length = 9
FEATURE                   Location/Qualifiers
source                    1..9
                          mol_type = protein
                          organism = Medicago sativa
SEQUENCE: 49
GRCRDDFRC                                                                     9

SEQ ID NO: 50             moltype = AA  length = 10
FEATURE                   Location/Qualifiers
source                    1..10
                          mol_type = protein
                          organism = Medicago truncatula
SEQUENCE: 50
GRCRGFRRRC                                                                   10

SEQ ID NO: 51             moltype = AA  length = 12
FEATURE                   Location/Qualifiers
source                    1..12
                          mol_type = protein
                          note = wild-type sequence from Medicago truncatula
                          organism = synthetic construct
SEQUENCE: 51
GACHRQGFGF AC                                                                12

SEQ ID NO: 52             moltype = AA  length = 12
FEATURE                   Location/Qualifiers
source                    1..12
                          mol_type = protein
                          note = wild-type sequence from Medicago truncatula
                          organism = synthetic construct
SEQUENCE: 52
GACHRQGIGF AC                                                                12

SEQ ID NO: 53             moltype = AA  length = 12
FEATURE                   Location/Qualifiers
source                    1..12
                          mol_type = protein
                          note = wild-type sequence from Medicago truncatula
                          organism = synthetic construct
SEQUENCE: 53
GGCHLDNTGV FC                                                                12

SEQ ID NO: 54             moltype = AA  length = 12
FEATURE                   Location/Qualifiers
source                    1..12
                          mol_type = protein
                          note = wild-type sequence from Medicago truncatula
                          organism = synthetic construct
SEQUENCE: 54
GACHRQGYGF AC                                                                12
```

```
SEQ ID NO: 55              moltype = AA  length = 12
FEATURE                    Location/Qualifiers
source                     1..12
                           mol_type = protein
                           note = wild-type sequence from Medicago truncatula
                           organism = synthetic construct
SEQUENCE: 55
GACHQDGFGF AC                                                         12

SEQ ID NO: 56              moltype = AA  length = 12
FEATURE                    Location/Qualifiers
source                     1..12
                           mol_type = protein
                           note = wild-type sequence from Medicago truncatula
                           organism = synthetic construct
SEQUENCE: 56
GACHRDGIGF AC                                                         12

SEQ ID NO: 57              moltype = AA  length = 12
FEATURE                    Location/Qualifiers
source                     1..12
                           mol_type = protein
                           note = wild-type sequence from Medicago truncatula
                           organism = synthetic construct
SEQUENCE: 57
GGCHLDNTGV FC                                                         12

SEQ ID NO: 58              moltype = AA  length = 18
FEATURE                    Location/Qualifiers
source                     1..18
                           mol_type = protein
                           note = wild-type sequence from Medicago truncatula
                           organism = synthetic construct
SEQUENCE: 58
GACHRQGFGF ACFCYKKC                                                   18

SEQ ID NO: 59              moltype = AA  length = 18
FEATURE                    Location/Qualifiers
source                     1..18
                           mol_type = protein
                           note = wild-type sequence from Medicago truncatula
                           organism = synthetic construct
SEQUENCE: 59
GACHRQGIGF ACFCKKKC                                                   18

SEQ ID NO: 60              moltype = AA  length = 18
FEATURE                    Location/Qualifiers
source                     1..18
                           mol_type = protein
                           note = wild-type sequence from Medicago truncatula
                           organism = synthetic construct
SEQUENCE: 60
GGCHLDNTGV FCFCDFKC                                                   18

SEQ ID NO: 61              moltype = AA  length = 18
FEATURE                    Location/Qualifiers
source                     1..18
                           mol_type = protein
                           note = wild-type sequence from Medicago truncatula
                           organism = synthetic construct
SEQUENCE: 61
GACHRQGYGF ACFCYKKC                                                   18

SEQ ID NO: 62              moltype = AA  length = 18
FEATURE                    Location/Qualifiers
source                     1..18
                           mol_type = protein
                           note = wild-type sequence from Medicago truncatula
                           organism = synthetic construct
SEQUENCE: 62
GACHQDGFGF ACFCYFNC                                                   18

SEQ ID NO: 63              moltype = AA  length = 18
FEATURE                    Location/Qualifiers
source                     1..18
                           mol_type = protein
                           note = wild-type sequence from Medicago truncatula
                           organism = synthetic construct
```

```
SEQUENCE: 63
GACHRDGIGF ACFCYFNC                                                          18

SEQ ID NO: 64          moltype = AA  length = 18
FEATURE                Location/Qualifiers
source                 1..18
                       mol_type = protein
                       note = wild-type sequence from Medicago truncatula
                       organism = synthetic construct
SEQUENCE: 64
GGCHLDNTGV FCFCDFKC                                                          18

SEQ ID NO: 65          moltype = DNA  length = 36
FEATURE                Location/Qualifiers
source                 1..36
                       mol_type = other DNA
                       organism = synthetic construct
CDS                    36
                       note = encodes wild-type peptide from Medicago truncatula
                       protein_id = 51
                       translation = GACHRQGFGFAC
SEQUENCE: 65
ggtgcttgtc atcgtcaagg ctttggtttt gcttgc                                      36

SEQ ID NO: 66          moltype = DNA  length = 36
FEATURE                Location/Qualifiers
source                 1..36
                       mol_type = other DNA
                       organism = synthetic construct
CDS                    36
                       note = encodes wild-type peptide from Medicago truncatula
                       protein_id = 52
                       translation = GACHRQGIGFAC
SEQUENCE: 66
ggtgcttgtc accgtcaagg cattggtttt gcttgc                                      36

SEQ ID NO: 67          moltype = DNA  length = 36
FEATURE                Location/Qualifiers
source                 1..36
                       mol_type = other DNA
                       organism = synthetic construct
CDS                    36
                       note = encodes wild-type peptide from Medicago truncatula
                       protein_id = 53
                       translation = GGCHLDNTGVFC
SEQUENCE: 67
gggggttgtc accttgataa cactggagtt ttttgt                                      36

SEQ ID NO: 68          moltype = DNA  length = 36
FEATURE                Location/Qualifiers
source                 1..36
                       mol_type = other DNA
                       organism = synthetic construct
CDS                    36
                       note = encodes wild-type peptide from Medicago truncatula
                       protein_id = 54
                       translation = GACHRQGYGFAC
SEQUENCE: 68
ggtgcttgtc accgtcaagg ctatggtttt gcttgc                                      36

SEQ ID NO: 69          moltype = DNA  length = 36
FEATURE                Location/Qualifiers
source                 1..36
                       mol_type = other DNA
                       organism = synthetic construct
CDS                    36
                       note = encodes wild-type peptide from Medicago truncatula
                       protein_id = 55
                       translation = GACHQDGFGFAC
SEQUENCE: 69
ggggcatgcc accaagatgg atttggattt gcttgc                                      36

SEQ ID NO: 70          moltype = DNA  length = 36
FEATURE                Location/Qualifiers
source                 1..36
                       mol_type = other DNA
                       organism = synthetic construct
CDS                    36
                       note = encodes wild-type peptide from Medicago truncatula
```

```
                                  protein_id = 56
                                  translation = GACHRDGIGFAC
SEQUENCE: 70
ggggcatgtc accgtgatgg cattggattt gcttgc                          36

SEQ ID NO: 71             moltype = DNA  length = 36
FEATURE                   Location/Qualifiers
source                    1..36
                          mol_type = other DNA
                          organism = synthetic construct
CDS                       36
                          note = encodes wild-type peptide from Medicago truncatula
                          protein_id = 57
                          translation = GGCHLDNTGVFC
SEQUENCE: 71
ggggggttgtc accttgataa cactggagtt ttttgt                         36

SEQ ID NO: 72             moltype = DNA  length = 54
FEATURE                   Location/Qualifiers
source                    1..54
                          mol_type = other DNA
                          organism = synthetic construct
CDS                       54
                          note = encodes wild-type peptide from Medicago truncatula
                          protein_id = 58
                          translation = GACHRQGFGFACFCYKKC
SEQUENCE: 72
ggtgcttgtc atcgtcaagg ctttggtttt gcttgcttct gctacaaaaa atgt      54

SEQ ID NO: 73             moltype = DNA  length = 54
FEATURE                   Location/Qualifiers
source                    1..54
                          mol_type = other DNA
                          organism = synthetic construct
CDS                       54
                          note = encodes wild-type peptide from Medicago truncatula
                          protein_id = 59
                          translation = GACHRQGIGFACFCKKKC
SEQUENCE: 73
ggtgcttgtc accgtcaagg cattggtttt gcttgcttct gcaagaaaaa atgt      54

SEQ ID NO: 74             moltype = DNA  length = 54
FEATURE                   Location/Qualifiers
source                    1..54
                          mol_type = other DNA
                          organism = synthetic construct
CDS                       54
                          note = encodes wild-type peptide from Medicago truncatula
                          protein_id = 60
                          translation = GGCHLDNTGVFCFCDFKC
SEQUENCE: 74
ggggggttgtc accttgataa cactggagtt ttttgtttct gcgacttcaa atgc     54

SEQ ID NO: 75             moltype = DNA  length = 54
FEATURE                   Location/Qualifiers
source                    1..54
                          mol_type = other DNA
                          organism = synthetic construct
CDS                       54
                          note = encodes wild-type peptide from Medicago truncatula
                          protein_id = 61
                          translation = GACHRQGYGFACFCYKKC
SEQUENCE: 75
ggtgcttgtc accgtcaagg ctatggtttt gcttgcttct gctacaaaaa gtgt      54

SEQ ID NO: 76             moltype = DNA  length = 54
FEATURE                   Location/Qualifiers
source                    1..54
                          mol_type = other DNA
                          organism = synthetic construct
CDS                       54
                          note = encodes wild-type peptide from Medicago truncatula
                          protein_id = 62
                          translation = GACHQDGFGFACFCYFNC
SEQUENCE: 76
ggggcatgcc accaagatgg atttggattt gcttgcttct gctacttcaa ttgc      54

SEQ ID NO: 77             moltype = DNA  length = 54
FEATURE                   Location/Qualifiers
```

```
source                  1..54
                        mol_type = other DNA
                        organism = synthetic construct
CDS                     54
                        note = encodes wild-type peptide from Medicago truncatula
                        protein_id = 63
                        translation = GACHRDGIGFACFCYFNC
SEQUENCE: 77
ggggcatgtc accgtgatgg cattggattt gcttgcttct gttacttcaa ctgc          54

SEQ ID NO: 78           moltype = DNA  length = 54
FEATURE                 Location/Qualifiers
source                  1..54
                        mol_type = other DNA
                        organism = synthetic construct
CDS                     54
                        note = encodes wild-type peptide from Medicago truncatula
                        protein_id = 64
                        translation = GGCHLDNTGVFCFCDFKC
SEQUENCE: 78
ggggttgtc accttgataa cactggagtt ttttgtttct gcgacttcaa atgc            54

SEQ ID NO: 79           moltype = AA   length = 6
FEATURE                 Location/Qualifiers
source                  1..6
                        mol_type = protein
                        organism = Saccharomyces cerevisiae
SEQUENCE: 79
KREAEA                                                                6

SEQ ID NO: 80           moltype = AA   length = 4
FEATURE                 Location/Qualifiers
source                  1..4
                        mol_type = protein
                        organism = Saccharomyces cerevisiae
SEQUENCE: 80
EAEA                                                                  4

SEQ ID NO: 81           moltype =    length =
SEQUENCE: 81
000
```

ANTIFUNGAL PLANT PROTEINS, PEPTIDES, AND METHODS OF USE

CROSS-REFERENCE TO RELATED APPLICATIONS

This application is a continuation of U.S. patent application Ser. No. 17/304,156, filed Jun. 15, 2021, which is a continuation of U.S. patent application Ser. No. 16/277,157, filed Feb. 15, 2019, now abandoned, which is a divisional of the U.S. patent application Ser. No. 14/888,011, filed Oct. 29, 2015, now Pat. No. 10,253,328, issued Apr. 9, 2019, which is the U.S. National Phase entry of International Application No. PCT/US2014/035786, filed Apr. 29, 2014, which claims the benefit of priority of U.S. Provisional Application Ser. No. 61/817,415, filed Apr. 30, 2013, the contents of which are herein incorporated by reference in their entireties.

SEQUENCE LISTING

The sequence listing contained in the file named "P13570US04_ST26", which is 107,388 bytes as measured in the Windows operating system, and which was created on Jun. 13, 2023, and electronically filed herewith, is incorporated herein by reference in its entirety.

BACKGROUND OF THE INVENTION

Field of the Invention

The present invention relates to small antifungal proteins and peptides derived from *Medicago truncatula* (Barrel Medic, Barrel Medick, or Barrel Clover), i.e., MtDef5 Defensins, and methods for controlling pathogenic fungi susceptible to the antifungal activity of these molecules. The antifungal proteins and peptides can be applied directly to a plant as a component of an antifungal composition, applied to a plant in the form of microorganisms that produce the proteins or peptides, or plants themselves can be genetically modified to produce the proteins or peptides. The present invention also relates to DNA constructs, microorganisms, and plants transformed with the DNA constructs, and compositions useful in controlling pathogenic plant and other fungi.

Description of Related Art

Protection of agriculturally important crops from pathogenic fungi is crucial in improving crop yields. Fungal infections are a particular problem in damp climates, and may become a major concern during crop storage, where such infections can result in spoilage and contamination of food or feed products with fungal toxins. Unfortunately, modern growing methods and harvesting and storage systems can promote plant pathogen infections.

Control of plant pathogens is further complicated by the need to simultaneously control multiple fungi of distinct genera. For example, fungi such as *Alternaria; Aspergillus; Ascochyta; Botrytis; Cercospora; Colletotrichum; Diplodia; Erysiphe; Fusarium; Gaeumannomyces; Helminthosporium; Macrophomina; Nectria; Peronospora; Phakopsora; Phoma; Phymatotrichum; Phytophthora; Plasmopara; Podosphaera; Puccinia; Pythium; Pyrenophora; Pyricularia; Rhizoctonia; Scerotium; Sclerotinia; Septoria; Thielaviopsis; Uncinula; Venturia*; and *Verticillium* species are all recognized plant pathogens. Consequently, resistant crop plant varieties or fungicides that control only a limited subset of fungal pathogens may fail to deliver adequate protection under conditions where multiple pathogens are present. It is further anticipated that plant pathogenic fungi may become resistant to existing fungicides and transgenic and non-transgenic crop varieties, necessitating the introduction of fungal control agents with distinct modes of action to combat resistant fungi.

One approach to inhibiting plant pathogenic fungal activity has been to identify and isolate peptides, polypeptides, and proteins exhibiting antifungal activity against plant pathogenic fungi (Bowles, 1990; Brears et al., 1994). The antifungal peptides, polypeptides, and proteins that include chitinases, cysteine-rich chitin-binding proteins, β-1,3-glucanases, permatins (including zeamatins), thionins, ribosome-inactivating proteins, and non-specific lipid transfer proteins are believed to play important roles in plant defense against fungal infection. The use of these protein products to control plant pathogens in transgenic plants has been reported, for example, in European Patent Application 0 392 225.

Another group of peptides known as defensins have been shown to inhibit plant pathogens. Defensins are small cysteine-rich peptides of 45-54 amino acids that constitute an important component of the innate immunity of plants (Thomma et al., 2002; Lay and Anderson, 2005). Widely distributed in plants, defensins vary greatly in their amino acid composition. However, they all have a compact shape that is stabilized by either four or five intramolecular disulfide bonds. Plant defensins have been extensively studied for their role in plant defense. Some plant defensins inhibit the growth of a broad range of fungi at micromolar concentrations (Broekaert et al., 1995; Broekaert et al., 1997; da Silva Conceicao and Broekaert, 1999) and, when expressed in transgenic plants, confer strong resistance to fungal pathogens (da Silva Conceicao and Broekaert, 1999; Thomma et al., 2002; Lay and Anderson, 2005). Two small cysteine-rich proteins isolated from radish seed, Rs-AFP1 and Rs-AFP2, inhibited the growth of many pathogenic fungi when the pure protein was added to an in vitro antifungal assay medium (U.S. Pat. No. 5,538,525). Transgenic tobacco plants containing the gene encoding Rs-AFP2 protein were found to be more resistant to attack by fungi than non-transformed plants.

Antifungal defensin proteins have also been identified in Alfalfa (*Medicago sativa*) and shown to inhibit plant pathogens such as *Fusarium* and *Verticillium* in both in vitro tests and in transgenic plants (U.S. Pat. No. 6,916,970). Under low salt in vitro assay conditions, the Alfalfa defensin AlfAFP1 inhibited *Fusarium culmorum* growth by 50% at 1 μg/ml and *Verticillium dahliae* growth by 50% at 4 μg/ml (i.e., $IC_{50}$ values of 1 μg/ml and 4 μg/ml, respectively). Expression of the AlfAFP1 protein in transgenic potato plants was also shown to confer resistance to *Verticillium dahliae* in both greenhouse and field tests (Gao et al, 2000). Mode-of-action analyses have also shown that AlfAFP1 (which is alternatively referred to as MsDef1, for *Medicago sativa* Defensin 1) induces hyper-branching of *F. graminearum* and can block L-type calcium channels (Spelbrink et al, 2004).

Other defensin genes have also been identified in the legume *Medicago truncatula* (Hanks et al, 2005). The cloned MtDef2 protein has been demonstrated through in vitro experiments to have little or no antifungal activity (Spelbrink et al, 2004). Analysis of the sequence database search identified 10 tentative consensus sequences (10 unique defensin-encoding genes represented by multiple ESTs) and six singletons (i.e., six unique defensin genes represented by a single EST) with homology to known *Medicago* defensin genes. One of the tentative consensus sequences was identified as TC85327 and shown to be expressed in both mock-treated and mycorrhizal fungus-infected *Medicago truncatula* roots. There was no demonstration that proteins encoded by any of the TC85327 *Medicago truncatula* sequences possessed anti-fungal activity in this study (Hanks et al, 2005).

Although defensin proteins such as AlfAFP1 (MsDef1) and Rs-AFP2 have been used to obtain transgenic plants that are resistant to fungal infections, other proteins that provide for increased levels of resistance are needed. In particular, proteins with increased specific activities against fungal pathogens would be particularly useful in improving the levels of fungal resistance obtained in transgenic plants. Furthermore, proteins that inhibit fungal pathogens via distinct modes of action would also be useful in combating fungal pathogens that have become resistant to defensin proteins such as AlfAFP1 (MsDef1) and Rs-AFP2.

The present invention meets this need by providing a family of novel small antifungal proteins and peptides from *Medicago truncatula*, MtDef5.1-5.6 (SEQ ID NOs:1, 3-9, 16-22, and 49-64).

SUMMARY OF THE INVENTION

Accordingly, among its various aspects, the present invention provides the following.
1. An isolated, purified antifungal protein or peptide, comprising an amino acid sequence having at least 90% sequence identity to an amino acid sequence selected from the group consisting of amino acid sequences shown in SEQ ID NOs:1, 3-9, 16-22, and 49-64.
2. The isolated, purified antifungal protein or peptide of 1, comprising a plant apoplast, vacuolar, or endoplasmic reticulum targeting amino acid sequence at its N-terminus.
3. The isolated, purified antifungal protein or peptide of 2, wherein said targeting sequence comprises an amino acid sequence having at least 90% sequence identity to an amino acid sequence selected from the group consisting of amino acid sequences shown in shown in SEQ ID NOs:30-35 and 42-48.
4. An isolated, purified nucleotide sequence encoding said isolated, purified antifungal protein or peptide of any one of 1-3.
5. The isolated, purified nucleotide sequence of 4, codon-optimized for expression in a plant of interest.
6. The isolated, purified nucleotide sequence of 4 or 5, wherein said plant of interest is a food crop plant.
7. The isolated, purified nucleotide sequence of 6, wherein said food crop plant is selected from the group consisting of soybean, wheat, maize, sugarcane, rice, and potato.
8. A transgenic plant, cells of which contain an antifungal protein or peptide comprising an amino acid sequence having at least 90% sequence identity to an amino acid sequence selected from the group consisting of amino acid sequences shown in SEQ ID NOs:1, 3-9, 16-22, and 49-64.
9. The transgenic plant of 8, wherein said antifungal protein or peptide further comprises a plant apoplast, vacuolar, or endoplasmic reticulum targeting amino acid sequence at its N-terminus.
10. The transgenic plant of 8 or 9, wherein said antifungal protein or peptide is present in said cells in an antifungal effective amount.
11. The transgenic plant of any one of 8-10, wherein said cells are root cells.
12. The transgenic plant of any one of 8-11, wherein said antifungal protein or peptide inhibits damage to said plant caused by a species of fungus selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.
13. The transgenic plant of any one of 8-12, the genome of which further comprises:
    DNA encoding a plant defensin selected from the group consisting of MsDef1, MtDef2, MtDef4, NaD1, Rs-AFP1, Rs-AFP2, KP4, and KP6, wherein said DNA is expressed and produces an anti-fungal effective amount of said defensin, and/or
    DNA encoding a *Bacillus thuringiensis* endotoxin, wherein said DNA is expressed and produces an anti-insect effective amount of said *Bacillus thuringiensis* endotoxin, and/or
    DNA encoding a protein that confers herbicide resistance to said plant, wherein said DNA is expressed and produces an anti-herbicide effective amount of said protein that confers herbicide resistance.
14. The transgenic plant of any one of 8-13, produced by a method comprising:
    a) inserting into the genome of a plant cell a recombinant, double-stranded DNA molecule comprising, operably linked for expression:
        (i) a promoter sequence that functions in plant cells to cause the transcription of an adjacent coding sequence to RNA;
        (ii) optionally, an intron;
        (iii) a coding sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and a plant apoplast, vacuolar, or endoplasmic reticulum targeting amino acid sequence at its N-terminus;
        (iv) a 3' non-translated sequence that functions in plant cells to cause transcriptional termination and the addition of polyadenylate nucleotides to the 3' end of said transcribed RNA;
    b) obtaining a transformed plant cell; and
    c) regenerating from said transformed plant cell a genetically transformed plant, cells of which express said antifungal protein or peptide.
15. The transgenic plant of 14, wherein said antifungal protein or peptide is expressed in an antifungal effective amount in cells of said transformed plant.
16. The transgenic plant of 14 or 15, wherein said coding sequence comprises a nucleotide sequence having a sequence identity to a nucleotide sequence selected from the group consisting of nucleotide sequences shown in SEQ ID NOs:10-15, 23-29, and 65-78 sufficient to enable said coding sequence to encode said antifungal protein or peptide, or a codon-optimized version of said coding sequence to optimize expression thereof in said plant.

17. The transgenic plant of any one of 14-16, wherein said promoter is a root-specific promoter.

18. The transgenic plant of 17, wherein said root-specific promoter is selected from the group consisting of RB7, RD2, ROOT1, ROOT2, ROOT3, ROOT4, ROOT5, ROOT6, ROOT7, and ROOT8.

19. The transgenic plant of any one of 8-18, which is selected from the group consisting of maize, soybean, wheat, sugarcane, rice, and potato.

20. A part of said transgenic plant of any one of 8-19.

21. The part of 20, which is selected from the group consisting of a protoplast, a cell, a tissue, an organ, a cutting, and an explant.

22. The part of 21, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

23. Progeny of said transgenic plant of any one of 8-19.

24. Seed of said transgenic plant of any one of 8-19.

25. A transgenic plant, cells of which comprise a nucleotide coding sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64.

26. The transgenic plant of 25, wherein said nucleotide coding sequence further encodes a plant apoplast, vacuolar, or endoplasmic reticulum targeting amino acid sequence at the N-terminus of said antifungal protein or peptide.

27. The transgenic plant of 25 or 26, wherein said antifungal protein or peptide is expressed in an antifungal effective amount in said cells.

28. The transgenic plant of any one of 25-27, wherein said cells are root cells.

29. The transgenic plant of any one of 25-28, produced by a method comprising:
    a) inserting into the genome of a plant cell a recombinant, double-stranded DNA molecule comprising, operably linked for expression:
        (i) a promoter that functions in plant cells to cause transcription of an adjacent coding sequence to RNA;
        (ii) optionally, an intron;
        (iii) a coding sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and a plant apoplast, vacuolar, or endoplasmic reticulum targeting amino acid sequence at its N-terminus; and
        (iv) a 3' non-translated region that functions in plant cells to cause transcriptional termination and the addition of polyadenylate nucleotides to the 3' end of said transcribed RNA;
    b) obtaining a transformed plant cell; and
    c) regenerating from said transformed plant cell a genetically transformed plant, cells of which express said antifungal protein or peptide.

30. The transgenic plant of 29, wherein said antifungal protein or peptide is expressed in an antifungal effective amount in cells of said plant.

31. The transgenic plant of 29 or 30, wherein said coding sequence comprises a nucleotide sequence having a sequence identity to a nucleotide sequence selected from the group consisting of nucleotide sequences shown in SEQ ID NOs:10-15, 23-29, and 65-78 sufficient to enable said coding sequence to encode said antifungal protein or peptide, or a codon-optimized version of said coding sequence to optimize expression thereof in said plant.

32. The transgenic plant of any one of 29-31, wherein said promoter is a root-specific promoter.

33. The transgenic plant of 32, wherein said root-specific promoter is selected from the group consisting of RB7, RD2, ROOT1, ROOT2, ROOT3, ROOT4, ROOT5, ROOT6, ROOT7, and ROOT8.

34. The transgenic plant of any one of 29-33, the genome of which further comprises:
    DNA encoding a plant defensin selected from the group consisting of MsDef1, MtDef2, MtDef4, NaD1, Rs-AFP1, Rs-AFP2, KP4, and KP6, wherein said DNA is expressed and produces an anti-fungal effective amount of said defensin, and/or
    DNA encoding a *Bacillus thuringiensis* endotoxin, wherein said DNA is expressed and produces an anti-insect effective amount of said *Bacillus thuringiensis* endotoxin, and/or
    DNA encoding a protein that confers herbicide resistance to said plant, wherein said DNA is expressed and produces an anti-herbicide effective amount of said protein that confers herbicide resistance.

35. The transgenic plant of any one of 29-34, which is selected from the group consisting of maize, soybean, wheat, sugarcane, rice, and potato.

36. A plant normally susceptible to damage from a species of fungus selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp., cells of which contain a coding sequence encoding a antifungal protein or peptide comprising an amino acid sequence having at least 90% sequence identity to an amino acid sequence selected from the group consisting of amino acid sequences shown in SEQ ID NOs:1, 3-9, 16-22, and 49-64.

37. The plant of 36, wherein said antifungal protein or peptide further comprises a plant apoplast, vacuolar, or endoplasmic reticulum targeting amino acid sequence at its N-terminus.

38. The plant of 36 or 37, wherein said antifungal protein or peptide is present in said cells in an antifungal effective amount.
39. The plant of any one of 36-38, wherein said cells are root cells.
40. The plant of any one of 36-39, which is selected from the group consisting of maize, soybean, wheat, sugarcane, rice, and potato.
41. A method of preventing, treating, controlling, combating, reducing, or inhibiting damage to a plant susceptible to damage from a species of fungus selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp., comprising providing to the locus of said susceptible plant an antifungal effective amount of a antifungal protein or peptide comprising an amino acid sequence having at least 90% sequence identity to an amino acid sequence selected from the group consisting of amino acid sequences shown in SEQ ID NOs:1, 3-9, 16-22, and 49-64, and any combination thereof.
42. The method of 41, wherein said antifungal protein or peptide is provided to said susceptible plant locus by expressing DNA encoding said antifungal protein or peptide within cells of said susceptible plant.
43. The method of 42, wherein said DNA encoding said antifungal protein or peptide comprises a nucleotide sequence having a sequence identity to a nucleotide sequence selected from the group consisting of nucleotide sequences shown in SEQ ID NOs:10-15, 23-29, and 65-78 sufficient to enable said coding sequence to encode said antifungal protein or peptide, or a codon-optimized version of said coding sequence to optimize expression thereof in said plant.
44. The method of 43, wherein said DNA further comprises a nucleotide sequence encoding a plant apoplast, vacuolar, or endoplasmic reticulum targeting amino acid sequence at the N-terminus of said antifungal protein or peptide.
45. The method of any one of 41-44, wherein said cells are root cells.
46. The method of 41, wherein said antifungal protein or peptide is provided to said susceptible plant locus by plant colonizing microorganisms that produce said antifungal protein or peptide.
47. The method of 41, wherein said antifungal protein or peptide is provided to said susceptible plant locus by applying a composition comprising plant colonizing microorganisms that produce said antifungal protein or peptide, or by applying said antifungal protein or peptide itself thereto.
48. The method of 47, wherein said composition comprises an agriculturally acceptable diluent, excipient, or carrier.
49. The method of any one of 41-48, wherein said susceptible plant is selected from the group consisting of maize, soybean, wheat, sugarcane, rice, and potato.
50. A method of preventing, treating, controlling, combating, reducing, or inhibiting damage to a plant susceptible to damage from a species of fungus selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp., comprising expressing DNA comprising a nucleotide sequence encoding a protein or peptide comprising an amino acid sequence having at least 90% sequence identity to an amino acid sequence selected from the group consisting of amino acid sequences shown in SEQ ID NOs:1, 3-9, 16-22, and 49-64, and any combination thereof, in cells of said susceptible plant at a level sufficient to inhibit said fungal damage.
51. The method of 50, wherein said antifungal protein or peptide is targeted to apoplasts, vacuoles, or the endoplasmic reticulum of cells of said susceptible plant.
52. The method of 50 or 51, wherein said antifungal protein or peptide is encoded by a nucleotide sequence having a sequence identity to a nucleotide sequence selected from the group consisting of nucleotide sequences shown in SEQ ID NOs:10-15, 23-29, and 65-78 sufficient to enable said nucleotide sequence to encode said antifungal protein or peptide, or a codon-optimized version of said nucleotide sequence to optimize expression thereof in said plant.
53. The method of any one of 50-52, wherein said cells are root cells.
54. The method of any one of 50-53, wherein said susceptible plant is selected from the group consisting of maize, soybean, wheat, sugarcane, rice, and potato.
55. A method of inhibiting damage to a plant susceptible to damage from a species of fungus selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp., comprising:
   a) inserting into the genome of a plant cell a recombinant, double stranded DNA molecule comprising, operably linked for expression:
      (i) a promoter that functions in plant cells to cause the transcription of an adjacent coding sequence to RNA;
      (ii) optionally, an intron;
      (iii) a coding sequence comprising a nucleotide sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64; and
(iv) a 3' nontranslated region that functions in said plant cells to cause transcriptional termination and the addition of polyadenylate nucleotides to the 3' end of said transcribed RNA;
b) obtaining a transformed plant cell; and
c) regenerating from said transformed plant cell a genetically transformed plant, cells of which express said antifungal protein or peptide.

56. The method of 55, wherein said antifungal protein or peptide is expressed in an antifungal amount in cells of said transformed plant.

57. The method of 55 or 56, wherein said antifungal protein or peptide is targeted to apoplasts, vacuoles, or the endoplasmic reticulum of cells of said transformed plant.

58. The method of any one of 55-57, wherein said nucleotide sequence encoding said antifungal protein or peptide is a nucleotide sequence having a sequence identity to a nucleotide sequence selected from the group consisting of nucleotide sequences shown in SEQ ID NOs:10-15, 23-29, and 65-78 sufficient to enable said nucleotide sequence to encode said antifungal protein or peptide, or a codon-optimized version of said nucleotide sequence to optimize expression thereof in said plant.

59. The method of any one of 55-58, wherein said promoter is a root-specific promoter.

60. The method of 59, wherein said root-specific promoter is selected from the group consisting of RB7, RD2, ROOT1, ROOT2, ROOT3, ROOT4, ROOT5, ROOT6, ROOT7, and ROOT8.

61. The method of any one of 55-60, wherein said susceptible plant is selected from the group consisting of maize, soybean, wheat, sugarcane, rice, and potato.

62. A method of controlling, combating, or inhibiting a species of fungus selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp., comprising contacting said fungal species with a composition comprising an antifungal effective amount of an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and any combination thereof.

63. The method of 62, wherein said composition comprises said antifungal protein or peptide, and an agriculturally acceptable carrier, diluent, or excipient.

64. The method of 62, wherein said composition comprises microorganisms expressing said antifungal protein or peptide.

65. A method of preventing, treating, controlling, combating, reducing, or inhibiting damage to a plant caused by a fungus, comprising:
a) inserting into the genome of a plant cell a recombinant, double stranded DNA molecule comprising, operably linked for expression:
(i) a promoter that functions in plant cells to cause the transcription of an adjacent coding sequence to RNA;
(ii) optionally, an intron;
(iii) a coding sequence comprising a nucleotide sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64; and
(iv) a 3' nontranslated region that functions in said plant cells to cause transcriptional termination and the addition of polyadenylate nucleotides to the 3' end of said transcribed RNA;
b) obtaining a transformed plant cell; and
c) regenerating from said transformed plant cell a genetically transformed plant, cells of which express said antifungal protein or peptide.

66. The method of 65, wherein said antifungal protein or peptide is expressed in an antifungal effective amount in cells of said transformed plant.

67. The method of 65 or 66, wherein said coding sequence further comprises a nucleotide sequence encoding a plant apoplast, vacuolar, or endoplasmic reticulum targeting amino acid sequence at the N-terminus of said antifungal protein or peptide.

68. The method of any one of 65-67, wherein said nucleotide sequence encoding said antifungal protein or peptide comprises a nucleotide sequence having a sequence identity to a nucleotide sequence selected from the group consisting of nucleotide sequences shown in SEQ ID NOs:10-15, 23-29, and 65-78 sufficient to enable said coding sequence to encode said antifungal protein or peptide, or a codon-optimized version of said coding sequence to optimize expression thereof in said plant.

69. The method of any one of 65-68, wherein said promoter is a root-specific promoter.

70. The method of 69, wherein said root-specific promoter is selected from the group consisting of RB7, RD2, ROOT1, ROOT2, ROOT3, ROOT4, ROOT5, ROOT6, ROOT7, and ROOT8.

71. The method of any one of 65-70, wherein said fungus is a species selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

72. The method of any one of 65-71, wherein said plant is selected from the group consisting of maize, soybean, wheat, sugarcane, rice, and potato.

73. A method of preventing, treating, controlling, combating, reducing, or inhibiting damage to a plant caused by a fungus, comprising:
transforming a plant with a DNA molecule encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and a plant apoplast, vacuolar, or endoplasmic reticulum targeting amino acid sequence at the N-terminus of said antifungal protein or peptide to produce a transformed plant, wherein cells of said transformed plant produce said antifungal protein or peptide, and wherein said transformed plant exhibits reduced fungal damage as compared to the fungal damage of an otherwise identical, untransformed control plant that does not produce said antifungal protein or peptide when both plants are contacted with similar amounts of said fungus and are grown under the same conditions.

74. The method of 73, wherein said cells are root cells.

75. The method of 73 or 74, wherein said fungus is a species selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

76. The method of any one of 73-75, wherein said plant is selected from the group consisting of maize, soybean, wheat, sugarcane, rice, and potato.

77. A method of reducing or inhibiting fungal contamination of soil, comprising cultivating in said soil transgenic plants expressing an antifungal protein or peptide comprising an amino acid sequence having at least 90% sequence identity to an amino acid sequence selected from the group consisting of amino acid sequences shown in SEQ ID NOs:1, 3-9, 16-22, and 49-64 in cells of roots of said transgenic plants.

78. The method of 77, wherein said root cells produce said antifungal protein or peptide in an antifungal effective amount.

79. The method of 77 or 78, wherein said antifungal protein or peptide is targeted to apoplasts, vacuoles, or the endoplasmic reticulum of said root cells.

80. The method of any one of 77-79, wherein said wherein said fungus is a species selected from the group consisting of an *Alternaria* sp., an *Ascochyta* sp., an *Aspergillus* sp., a *Botrytis* sp., a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

81. The method of any one of 77-80, wherein said transgenic plants are transgenic food crop plants.

82. The method of 81, wherein said transgenic food crop plants are selected from the group consisting of maize, soybean, wheat, sugarcane, rice, and potato.

83. A recombinant, double-stranded DNA molecule comprising, operatively linked for expression:
a) a promoter that functions in plant cells to cause transcription of an adjacent coding sequence to RNA;
b) optionally, an intron;
c) a nucleotide sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and a plant apoplast, vacuolar, or endoplasmic reticulum targeting amino acid sequence at the N-terminus of said antifungal protein or peptide; and
d) a 3' non-translated sequence that functions in plant cells to cause transcriptional termination and the addition of polyadenylate nucleotides to the 3' end of said transcribed RNA.

84. The recombinant, double-stranded DNA molecule of 83, wherein said promoter is a root-specific promoter.

85. The recombinant, double-stranded DNA molecule of 84, wherein said root-specific promoter is selected from the group consisting of RB7, RD2, ROOT1, ROOT2, ROOT3, ROOT4, ROOT5, ROOT6, ROOT7, and ROOT8.

86. The recombinant, double-stranded DNA molecule of any one of 83-85, which is codon-optimized for expression in a plant of interest.

87. The recombinant, double-stranded DNA molecule of 86, wherein said plant of interest is selected from the group consisting of maize, soybean, wheat, sugarcane, rice, and potato.

88. An expression construct, comprising a recombinant, double-stranded DNA molecule comprising, operably linked for expression:
a) a promoter that functions in plant cells to cause transcription of an adjacent coding sequence to RNA;
b) optionally, an intron;
c) a nucleotide sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and a plant apoplast, vacuolar, or endoplasmic reticulum targeting amino acid sequence at the N-terminus of said antifungal protein or peptide; and
d) a 3' non-translated sequence that functions in plant cells to cause transcriptional termination and the addition of polyadenylate nucleotides to the 3' end of said transcribed RNA.

89. The expression construct of 88, wherein said promoter is a root-specific promoter.

90. The expression construct of 89, wherein said root-specific promoter is selected from the group consisting of RB7, RD2, ROOT1, ROOT2, ROOT3, ROOT4, ROOT5, ROOT6, ROOT7, and ROOT8.

91. The expression construct of any one of 89-90, wherein said recombinant, double-stranded DNA molecule is codon-optimized for expression in a plant of interest.

92. The expression construct of 91, wherein said plant of interest is selected from the group consisting of maize, soybean, wheat, sugarcane, rice, and potato.

93. A plant transformation vector, comprising said recombinant, double-stranded DNA molecule of any one of 83-87, or the expression construct of any one of 88-92, and a selectable or scoreable marker for selection of transformed plant cells.

94. An antifungal composition, comprising an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and any combination thereof.

95. The antifungal composition of 94, wherein said antifungal protein or peptide, or combination thereof, is present in an antifungal effective amount.

96. The antifungal composition of 94 or 95, further comprising an agriculturally or pharmaceutically acceptable carrier, diluent, or excipient.

97. The antifungal composition of any one of 94-96, wherein said antifungal protein or peptide, or combination thereof, is present in a concentration in the range of from about 0.1 microgram per milliliter to about 500 milligrams per milliliter.

98. The antifungal composition of any one of 94-96, wherein said wherein said antifungal protein or peptide, or combination thereof, is present in a concentration in the range of from about 5 micrograms per milliliter to about 250 milligrams per milliliter.

99. The antifungal composition of any one of 94-98, having a pH in the range of from about 3 to about 9.

100. The antifungal composition of any one of 94-99, formulated with one or more additives selected from the group consisting of an inert material, a surfactant, and a solvent.

101. The antifungal composition of any one of 94-100, formulated in a mixture of one or more other active agents selected from the group consisting of a pesticidally active substance, a fertilizer, an insecticide, an attractant, a sterilizing agent, an acaricide, a nematocide, a herbicide, and a growth regulator.

102. The antifungal composition of 101, wherein said pesticidally active substance is selected from the group consisting of a fungal antibiotic and a chemical fungicide.

103. The antifungal composition of 102, wherein said fungal antibiotic or chemical fungicide is selected from the group consisting of a polyoxine, a nikkomycine, a carboxyamide, an aromatic carbohydrate, a carboxine, a morpholine, a sterol biosynthesis inhibitor, and an organophosphate.

104. Use of said antifungal composition of any one of 94-103 to inhibit the growth of a susceptible fungal species.

105. The use of 104, wherein said susceptible fungal species is selected from the group consisting of an *Alternaria* sp., an *Ascochyta* sp., an *Aspergillus* sp., a *Botrytis* sp., a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

106. The antifungal composition of any one of 94-103 for use in inhibiting the growth of a susceptible fungal species.

107. The use of 106, wherein said susceptible fungal species is selected from the group consisting of an *Alternaria* sp., an *Ascochyta* sp., an *Aspergillus* sp., a *Botrytis* sp., a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

108. The antifungal composition of any one of 94-103, provided to a plant locus by plant colonizing microorganisms producing said protein, peptide, or combination thereof, or by a composition comprising said plant colonizing microorganisms.

109. The antifungal composition of 94 or 95, wherein said protein, peptide, or combination thereof is expressed from DNA encoding said protein, peptide, or combination thereof within cells of a transgenic plant.

110. A method of controlling, combating, or inhibiting a susceptible fungus, comprising contacting said susceptible fungus with a transgenic plant, cells of which comprise and express a nucleotide sequence encoding an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and a plant apoplast, vacuolar, or endoplasmic reticulum targeting amino acid sequence at the N-terminus of said antifungal protein or peptide.

111. The method of 110, wherein said antifungal protein or peptide is expressed in cells of roots of said transgenic plant.

112. The method of 111, wherein said antifungal protein or peptide is expressed by said root cells in an antifungal effective amount.

113. The method of any one of 110-112, wherein said susceptible fungus is a species is selected from the group consisting of an *Alternaria* sp., an *Ascochyta* sp., an *Aspergillus* sp., a *Botrytis* sp., a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

114. The method of any one of 110-113, wherein said transgenic plant is selected from the group consisting of maize, soybean, wheat, sugarcane, rice, and potato.

115. An antifungal protein or peptide comprising an amino acid sequence having at least 90% sequence identity to an amino acid sequence selected from the group consisting of amino acid sequences shown in SEQ ID NOs:1, 3-9, 16-22, and 49-64, for use in human therapy.

116. An antifungal protein or peptide comprising an amino acid sequence having at least 90% sequence identity to an amino acid sequence selected from the group consisting of amino acid sequences shown in SEQ ID NOs:1, 3-9, 16-22, and 49-64, for use in treating a susceptible fungal infection.

117. Use of an antifungal protein or peptide comprising an amino acid sequence having at least 90% sequence identity to an amino acid sequence selected from the group consisting of amino acid sequences shown in SEQ ID NOs:1, 3-9, 16-22, and 49-64, in human therapy.

118. Use of an antifungal protein or peptide comprising an amino acid sequence having at least 90% sequence identity to an amino acid sequence selected from the group consisting of amino acid sequences shown in SEQ ID NOs:1, 3-9, 16-22, and 49-64, in treating a susceptible fungal infection.

119. Use of an antifungal protein or peptide comprising an amino acid sequence having at least 90% sequence identity to an amino acid sequence selected from the group consisting of amino acid sequences shown in SEQ ID NOs:1, 3-9, 16-22, and 49-64, for the manufacture of a medicament to treat a susceptible fungal infection.

120. A method of treating a susceptible fungal infection in a patient in need thereof, comprising administering to said patient an antifungal effective amount of an antifungal protein or peptide comprising an amino acid sequence having at least 90% sequence identity to an amino acid sequence selected from the group consisting of amino acid sequences shown in SEQ ID NOs:1, 3-9, 16-22, and 49-64, and any combination thereof.

121. The method of 120, wherein said administering is performed topically.

Further scope of the applicability of the present invention will become apparent from the detailed description and drawing(s) provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed descriptions taken in conjunction with the accompanying drawing(s), all of which are given by way of illustration only, and are not limitative of the present invention, in which.

DETAILED DESCRIPTION OF THE INVENTION

Figure 1:
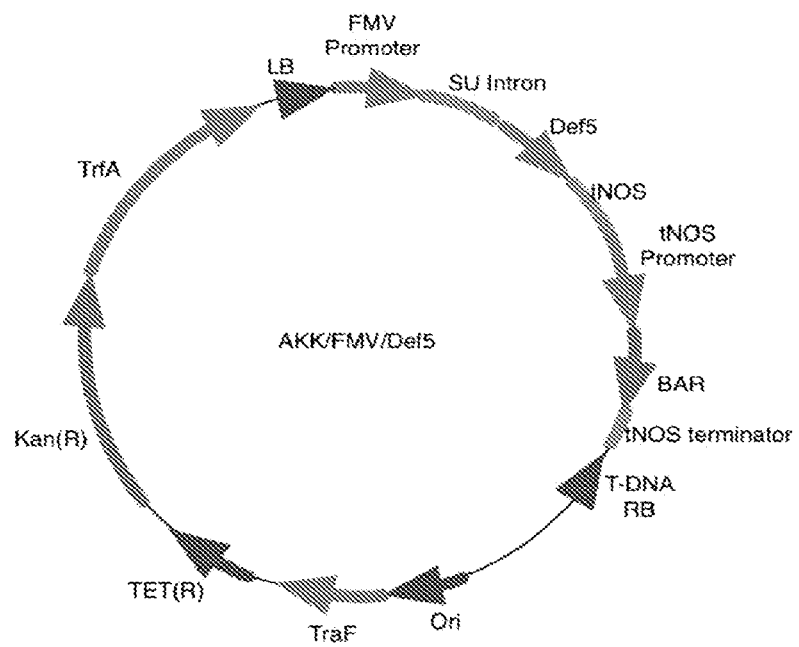
FIG. 1 shows transformation vector AKK/FMV/Def5 used to make MtDef5-expressing soybean lines. "LB"=T-DNA left border; "T-DNA RB"=T-DNA right border; "tNOS"=Nopaline synthase terminator sequence; "FMV"=Figwort mosaic virus 35S; "SU intron"=Super ubiquitin intron; "BAR"=Bialophos resistance gene; "NOS"=Nopaline synthase promoter; "On"=Origin of replication; "TraF"=Transfer F; "Tet(R)"=tetracycline resistance gene; "Kan(R)"=Kanamycin resistance gene; "TrfA"=T-DNA replication factor, and "Def5" represents a MtDef5 protein or peptide coding sequence.
Figure 2:
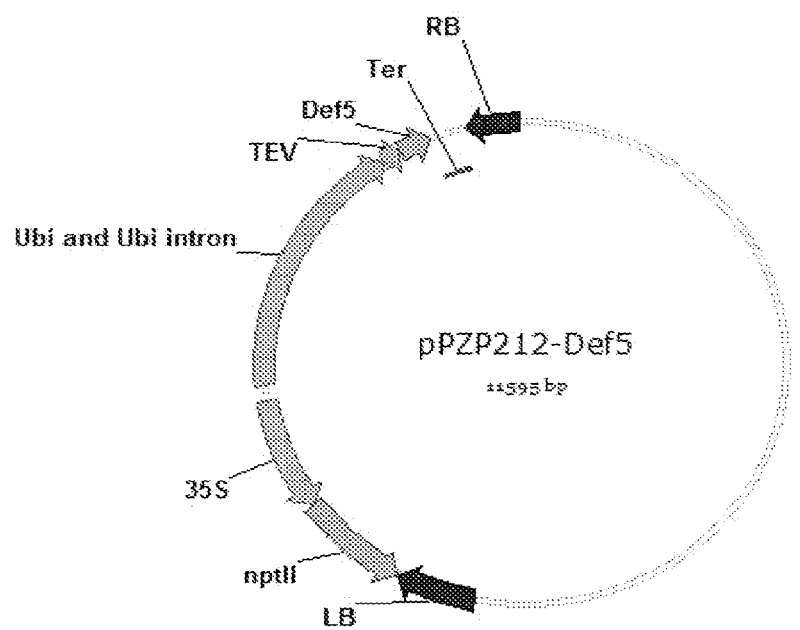
FIG. 2 shows transformation vector pZP212-Def5 to be used for making MtDef5-expressing wheat lines. "LB"=T-DNA left border; "T-DNA RB"=T-DNA right border; nptII=neomycin phosphotransferase II; 35S=CaMV35S promoter; Ubi and Ubi intron=Maize Ubi1A promoter and intron; TEV=tobacco etch virus leader; Def5=a MtDef5 protein or peptide coding sequence; ter=CaMV 35S termination signal.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references discussed in this specification, including the references cited therein, are herein incorporated by reference in their entirety.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

The amino acid and nucleotide sequences of the MtDef5 proteins and peptides, as well as those of the other elements useful in the constructs, methods, and organisms of the present invention, can be found at the end of the specification. All the amino acid and nucleotide sequences encompassed by the present invention include sequences consisting of, consisting essentially of, or comprising those specifically disclosed. As would be appreciated by one of ordinary skill in the art, as a result of the degeneracy of the genetic code, there are many nucleotide sequences that encode the protein and peptide molecules disclosed herein. Some of these polynucleotides may bear minimal homology to the nucleotide sequence of any native coding sequence.

In addition, polynucleotides that vary due to differences in codon usage are specifically contemplated by the present invention, and include those that are optimized for expression in monocots, dicots, yeasts, or bacteria. Nakamura et al. (2000) *Nucl. Acids Res.* 28(1):292 discusses the incorporation of preferred codons to enhance the expression of polynucleotides in various organisms. Codon usage in various monocot or dicot genes has been disclosed in Kawabe and Miyashita (2003) "Patterns of codon usage bias in three dicot and four monocot plant species", *Genes Genet. Syst.* 78:343-352, and in Murray et al. (1989) "Codon Usage in Plant Genes" NAR 17:477-498. Methods for optimizing codon usage in plants are also disclosed in U.S. Pat. Nos. 5,500,365; 5,689,052; 5,500,365; and 5,689,052.

MtDef5 protein- and peptide-encoding nucleotide sequences, and promoter nucleotide sequences used to drive their expression, can be genomic or non-genomic nucleotide sequences. Genomic and non-genomic nucleotide sequences encoding MtDef5 proteins and peptides, and promoters, include, for example, naturally-occurring mRNA, synthetically produced mRNA, naturally-occurring nucleotide sequences encoding MtDef5 proteins and peptides, and promoters, or synthetically produced nucleotide sequences encoding MtDef5 proteins and peptides, and promoters. Synthetic nucleotide sequences can be produced by means well known in the art, including, for example, by chemical or enzymatic synthesis of oligonucleotides, and include, for example, cDNA, codon-optimized sequences for efficient expression in different transgenic plants reflecting the pattern of codon usage in such plants, variants containing conservative (or non-conservative) amino acid substitutions that do not adversely affect their normal activity, PCR-amplified nucleotide sequences, etc.

DEFINITIONS

Unless defined otherwise, all technical and scientific terms used herein have the same meaning as commonly understood by those of ordinary skill in the art to which the invention pertains. Any methods and materials similar or equivalent to those described herein can be used in the practice or testing of the present invention in place of the methods and materials described herein.

For the purposes of the present invention, the following terms are defined below.

The term "food crop plant" to which the methods and compositions disclosed herein can be applied refers to plants that are either directly edible, or which produce edible products, and that are customarily used to feed humans either directly, or indirectly through animals. Non-limiting examples of such plants include:

1. Cereal crops: wheat, rice, maize (corn), barley, oats, sorghum, rye, and millet;
2. Protein crops: peanuts, chickpeas, lentils, kidney beans, soybeans, lima beans;
3. Roots and tubers: potatoes, sweet potatoes, and cassavas;
4. Oil crops: corn, soybeans, canola (rapeseed), wheat, peanuts, palm, coconuts, safflower, cottonseed, sunflower, flax, olive, and safflower;
5. Sugar crops: sugar cane and sugar beets;
6. Fruit crops: bananas, oranges, apples, pears, breadfruit, pineapples, and cherries;
7. Vegetable crops and tubers: tomatoes, lettuce, carrots, melons, asparagus, etc.
8. Nuts: cashews, peanuts, walnuts, pistachio nuts, almonds;
9. Forage and turf grasses;
10. Forage legumes: alfalfa, clover;
11. Drug crops: coffee, cocoa, kola nut, poppy;
12. Spice and flavoring crops: vanilla, sage, thyme, anise, saffron, menthol, peppermint, spearmint, coriander The terms "biofuels crops" or "energy crops" to which the present methods and compositions can also be applied include the oil crops listed in item 4, above, and further include plants such as sugarcane, castor bean, *Camelina*, switchgrass, *Miscanthus*, and *Jatropha*.

The singular terms "a", "an", and "the" include plural referents unless context clearly indicates otherwise. Similarly, the word "or" is intended to include "and" unless the context clearly indicates otherwise. Hence, comprising A or B means including A, or B, or A and B.

By "about" is meant a quantity, level, value, number, frequency, percentage, dimension, size, amount, weight, length, or the like, that varies by as much as ±30, 25, 20, 15, 10, 9, 8, 7, 6, 5, 4, 3, 2, or 1% compared to a reference quantity, level, value, number, frequency, percentage, dimension, size, amount, weight, length, or the like.

The endpoints of all ranges disclosed herein directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.).

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary.

Furthermore, the use of the term "including", as well as other related forms, such as "includes" and "included", is not limiting.

The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such fragment located in its (their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

A "heterologous" MtDef5 protein- or peptide-encoding nucleotide sequence can be one or more additional copies of an endogenous MtDef5 protein- or peptide-encoding nucleotide sequence, or a nucleotide sequence from another plant or other source. Furthermore, these can be genomic or non-genomic nucleotide sequences. Non-genomic nucleotide sequences encoding MtDef5 proteins or peptides include, for example, naturally occurring mRNA; synthetic mRNA produced, for example, by enzymatic synthesis or chemical oligonucleotide synthesis; synthetically produced MtDef5 protein- or peptide-encoding DNA sequences including, for example, those made by chemical oligonucleotide synthesis or enzymatic synthesis, including, for example, cDNA, codon-optimized sequences for efficient expression in different transgenic plants reflecting the pattern of codon usage in such plants, nucleotide sequences that differ from naturally occurring genomic sequences due to the degeneracy of the genetic code but that still encode MtDef5 proteins or peptides disclosed herein, nucleotide sequences encoding MtDef5 proteins or peptides comprising conservative (or non-conservative) amino acid substitutions that do not adversely affect their normal antifungal activity, PCR-amplified nucleotide sequences, and other non-genomic forms of nucleotide sequences familiar to those of ordinary skill in the art.

A "transgenic" organism, such as a transgenic plant, is a host organism that has been genetically engineered to contain one or more heterologous nucleic acid fragments, including nucleotide coding sequences, expression cassettes, vectors, etc. Introduction of heterologous nucleic acids into a host cell to create a transgenic cell is not limited to any particular mode of delivery, and includes, for example, microinjection, adsorption, electroporation, particle gun bombardment, whiskers-mediated transformation, liposome-mediated delivery, Agrobacterium-mediated transfer, the use of viral and retroviral vectors, etc., as is well known to those skilled in the art.

The term "genome" can collectively refer to the totality of different genomes within plant cells, i.e., nuclear genome, plastid (e.g., chloroplast genome), and mitochondrial genome, or separately to the each of these individual genomes when specifically indicated. As used herein, the term "genome" refers to the nuclear genome unless indicated otherwise. The "genome" for expression of the MtDef5 proteins or peptides employed in the present recombinant methods and plants is the nuclear genome. However, expression in a plastid genome, e.g., a chloroplast genome, or targeting of a MtDef5 protein or peptide to a plastid genome such as a chloroplast via the use of a plastid targeting sequence, is also encompassed by the present disclosure.

The term "control plant" refers to a plant without introduced trait-improving recombinant DNA. A control plant is used as a standard against which to measure and compare trait improvement in a transgenic plant comprising such trait-improving recombinant DNA. One suitable type of control plant is a non-transgenic plant of the parental line that was used to generate a transgenic plant, i.e., an otherwise identical wild-type plant. Another type of suitable control plant is a transgenic plant that comprises recombinant DNA without the specific trait-producing DNA, e.g., simply an empty vector.

The phrases "antifungal protein" or "antifungal peptide" as used herein refer to proteins and peptides that exhibit any one or more of the following characteristics: inhibiting or retarding the growth of fungal cells; killing fungal cells; disrupting or retarding stages of the fungal life cycle, such as spore germination, sporulation, or mating; and/or disrupting fungal cell infection, penetration, or spread within a plant. The net effect is thus to limit, decrease, or eliminate fungal pathogenesis and/or damage to a plant.

The phrase "biological functional equivalents" and the like as used herein refer to peptides, polypeptides, and proteins that contain a sequence or structural feature(s) similar or identical to that of an MtDef5 protein or peptide of the present invention, and which exhibit the same or similar, e.g., about ±30%, antifungal activity of an MtDef5 protein or peptide of the present invention. Biological functional equivalents also include peptides, polypeptides, and proteins that react with (i.e., specifically bind) to monoclonal and/or polyclonal antibodies raised against an MtDef5 protein or peptide as disclosed herein, and that exhibit the same or similar, e.g., about ±30%, antifungal activity as an MtDef5 protein or peptide of the present invention.

The phrases "combating fungal damage", "combating or controlling fungal damage", "controlling fungal damage", or the like as used herein refer to reduction in damage to a crop plant or crop plant product due to infection by a fungal pathogen. More generally, these phrases refer to reduction in the adverse effects caused by the presence of an undesired fungus in the crop plant. Adverse effects of fungal growth are understood to include any type of plant tissue damage or necrosis, any type of plant yield reduction, any reduction in the value of the crop plant product, and/or production of undesirable fungal metabolites or fungal growth by-products including, but not limited to, mycotoxins.

The phrase "DNA construct" as used herein refers to any DNA molecule in which two or more ordinarily distinct DNA sequences have been covalently linked. Examples of DNA constructs include, but are not limited to, plasmids, cosmids, viruses, BACs (bacterial artificial chromosome), YACs (yeast artificial chromosome), plant minichromosomes, autonomously replicating sequences, phage, or linear or circular single-stranded or double-stranded DNA sequences, derived from any source, that are capable of genomic integration or autonomous replication. DNA constructs can be assembled by a variety of methods including, but not limited to, recombinant DNA techniques, DNA synthesis techniques, PCR (Polymerase Chain Reaction) techniques, or any combination of techniques.

The phrases "a plant pathogenic fungus inhibitory amount" or "antifungal effective amount", or the like, as used herein in the context of a transgenic plant or microorganism expressing a MtDef5 protein or peptide, or an agricultural or pharmaceutical composition containing a MtDef5 protein, peptide, or any combination thereof used for antifungal purposes, as the case may be, refers to an amount of an MtDef5 protein and/or peptide that results in any measurable decrease in fungal growth in the transgenic plant and/or any measurable decrease in the adverse effects caused by fungal growth in the transgenic plant, or that results in any measurable decrease in fungal growth and/or any measurable decrease in the adverse effects caused by fungal growth in the particular application in which it is employed, respectively. The latter includes, for example, human and veterinary therapeutic applications. An antifungal effective amount of a MtDef5 protein or peptide, or any combination thereof, is an amount or dose that, upon single or multiple dose administration to a patient or subject, provides the desired prevention or treatment.

In the context of a transgenic plant, a plant pathogenic fungus inhibitory amount (antifungal effective amount) of a MtDef5 protein or peptide, is at least about 0.05 PPM, at least about 0.5 PPM, at least about 1.0 PPM, or at least about 2.0 PPM, where PPM are "parts per million" of MtDef5 protein or peptide present in fresh weight plant tissue, where 1 microgram of MtDef5 protein or peptide per 1 gram of fresh weight plant tissue represents a concentration of 1 PPM.

The phrase "a heterologous promoter", as used herein in the context of a DNA construct, refers to either: i) a promoter that is derived from a source distinct from the operably linked structural coding sequence or ii) a promoter derived the same source as the operably linked structural gene, where the promoter's sequence is modified from its original form.

The term "homolog" as used herein refers to a gene related to a second gene by identity of either the DNA sequences or the encoded protein sequences. Genes that are homologs can be genes separated by the event of speciation (see "ortholog"). Genes that are homologs may also be genes separated by the event of genetic duplication (see "paralog"). Homologs can be from the same or a different organism and may perform the same biological function in either the same or a different organism.

The phrase "MtDef5 protein or peptide" as used herein refers to: i) proteins or peptides with at least about 70% sequence identity to a mature MtDef5 protein sequence, or peptide sequence, disclosed herein and ii) proteins with at least about 70% sequence identity to MtDef5 proprotein sequences comprising an MtDef5 signal peptide and a mature MtDef5 protein. Mature MtDef5 protein sequences include, but are not limited to, a MtDef5.1a mature protein sequence (SEQ ID NO:16), a MtDef5.1b mature protein sequence (SEQ ID NO: 17), a MtDef5.2 mature protein sequence (SEQ ID NO:18), a MtDef5.3 mature protein sequence (SEQ ID NO: 19), a MtDef5.4 mature protein sequence (SEQ ID NO:20), a MtDef5.5 mature protein sequence (SEQ ID NO:21), and a MtDef5.6 mature protein sequence (SEQ ID NO:22), as well as coding sequences therefor as exemplified by SEQ ID NOs:23-29, respectively; proteins that have at least about 70% sequence identity to these sequences; and biological functional equivalents of these sequences. MtDef5 proprotein sequences include, but are not limited to, a MtDef5.1a proprotein sequence (SEQ ID NO:1), a MtDef5.1a-5.1b proprotein sequence (SEQ ID NO:4), a MtDef5.2 proprotein sequence (SEQ ID NO:5), a MtDef5.3 proprotein sequence (SEQ ID NO:6), a MtDef5.4 proprotein sequence (SEQ ID NO:7), a MtDef5.5 proprotein sequence (SEQ ID NO:8), and a MtDef5.6 proprotein sequence (SEQ ID NO:9), as well as coding sequences therefor as exemplified by SEQ ID NOs:10-15, respectively; proteins that have at least about 70% sequence identity to these sequences; and biological functional equivalents of these sequences.

It is interesting to note that mature MtDef5.1 a protein (SEQ ID NO:16) and mature MtDef5.1b protein (SEQ ID NO:17) appear to be expressed as a dimer as components of MtDef5.1a-MtDef5.1b proprotein (SEQ ID NO:4), wherein the peptide having the amino acid sequence shown in SEQ ID NO:2, i.e., APKKVEP, acts as a "linker".

The phrase "inhibiting growth of a plant pathogenic fungus" as used herein refers to methods that result in any measurable decrease in fungal growth, where fungal growth includes, but is not limited to, any measurable decrease in the numbers and/or extent of fungal cells, spores, conidia, or mycelia. As used herein, "inhibiting growth of a plant pathogenic fungus" is also understood to include any measurable decrease in the adverse effects cause by fungal growth in a plant. Adverse effects of fungal growth in a plant include any type of plant tissue damage or necrosis, any type of plant yield reduction, any reduction in the value of the crop plant product, and/or production of undesirable fungal metabolites or fungal growth by-products including, but not limited to, mycotoxins.

The term "orthologs" as used herein refers to two or more homologous genes in different species that evolved from a common ancestral gene by speciation. Orthologs may have the same biological function in different species.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and the coding sequence is linked such that the resulting translation product is in frame with the translational open reading frame that encodes the desired protein. Nucleic acid sequences that can be operably linked include, but are not limited to, sequences that provide gene expression functions (e.g., gene expression elements such as promoters, 5' untranslated regions, introns, protein coding regions, 3' untranslated regions, polyadenylation sites, and/or transcriptional terminators), sequences that provide DNA transfer and/or integration functions (e.g., T-DNA border sequences, site specific recombinase recognition sites, integrase recognition sites), sequences that provide for selective functions (e.g., antibiotic resistance markers, biosynthetic genes), sequences that provide scoreable marker functions (e.g., reporter genes), sequences that facilitate in vitro or in vivo manipulations of the sequences (e.g., polylinker sequences, site specific recombination sequences) and sequences that provide replication functions (e.g., bacterial origins of replication, autonomous replication sequences, centromeric sequences).

The phrase "percent identity" as used herein refers to the number of elements (i.e., amino acids or nucleotides) in a sequence that are identical within a defined length of two optimally aligned DNA, RNA, or protein segments. To calculate the "percent identity", the number of identical elements is divided by the total number of elements in the defined length of the aligned segments and multiplied by 100. When percentage of identity is used in reference to proteins it is understood that certain amino acid residues may not be identical but are nonetheless conservative amino acid substitutions that reflect substitutions of amino acid residues with similar chemical properties (e.g., acidic or basic, hydrophobic, hydrophilic, hydrogen bond donor or acceptor residues). Such substitutions may not change the functional properties of the molecule. Consequently, the percent identity of protein sequences can be increased to account for conservative amino acid substitutions.

The term "regeneration" as used herein refers to any method of obtaining a whole plant from any one of, for example, a seed, a protoplast, a plant cell, a group of plant cells, plant callus tissue, or an excised piece of a plant.

The terms "susceptible fungus (or fungi)", susceptible fungal infection, and the like refer to fungi that infect plants, or human or animal patients or subjects, or fungal infections thereof, that are responsive to, and detrimentally affected by, the growth inhibiting or growth retarding effect, and/or pathogenesis-retarding effect, of the MtDef5 molecules disclosed herein. Such susceptible fungi can be killed by these molecules, or stages of their life cycle, such as spore germination, sporulation, or mating; infection, penetration, or spread within a plant or mammal, are disrupted or retarded by the MtDef5 molecules. The net effect of the Def5 molecules on such fungi and fungal infections is to prevent, limit, decrease, treat, inhibit, or completely eliminate fungal pathogenesis and/or damage to a plant, human, or animal in contact with such fungus. Susceptible fungi can be identified by any of the assay methods disclosed herein.

The term "transformation" as used herein refers to a process of introducing an exogenous DNA sequence (e.g., a vector, a recombinant DNA molecule) into a cell or protoplast in which that exogenous DNA is incorporated into a chromosome or is capable of autonomous replication.

The phrase "transgenic plant" refers to a plant or progeny thereof derived from a transformed plant cell, protoplast, or other transformed plant tissue wherein the plant DNA contains an introduced exogenous DNA molecule not originally present in a corresponding native, non-transgenic plant of the same species.

The term "treating" (or "treat" or "treatment") means slowing, interrupting, arresting, controlling, stopping, reducing, or reversing the progression or severity of a symptom, disorder, condition, or disease caused by a plant or other fungal pathogen, and can include a total elimination of all fungal disease-related symptoms, conditions, or disorders of affected plants or human or veterinary subjects.

The term "vector" as used herein refers to a DNA or RNA molecule capable of replication in a host cell and/or to which another DNA or RNA segment can be operatively linked so as to bring about replication of the attached segment. A plasmid is an exemplary vector.

The present invention provides isolated DNA constructs useful for expressing the MtDef5 antifungal proteins and peptides disclosed herein. The isolated DNA constructs comprise a heterologous promoter, optional intron, a sequence that encodes a MtDef5 protein or peptide with at least about 85% sequence identity to any one of SEQ ID NOs:1, 3-9, 16-22, and 49-64), and a polyadenylation sequence, wherein the promoter, optional intron, the sequence encoding a signal peptide, the sequence encoding a mature MtDef5 protein or peptide, and the polyadenylation sequence are operably linked for expression.

Isolated DNA constructs of the invention can further comprise a sequence that encodes a signal peptide that is operably linked to the sequence that encodes the MtDef5 protein. The signal peptides used in DNA constructs of the invention are selected from the group consisting of yeast signal peptides, monocot plant signal peptides, dicot plant signal peptides, and synthetic signal peptides. Yeast signal peptides can be selected from the group consisting of an α-factor signal peptide, an invertase signal peptide, and a PHO1 signal peptide. Dicot plant signal peptides can be selected from the group consisting of a MtDef1.1, a MsDef1.6, a MtDef2.1, a MtDef4, a MtDef5, and a tobacco PR1b signal peptide. Monocot plant signal peptides can be selected from the group consisting of a cysteine endoproteinase signal peptide and an α-amylase signal peptide. The MtDef5 signal peptides can be selected from the group consisting of SEQ ID NOs:30-35 signal peptide sequences.

A variety of DNA sequences encoding the MtDef5 proteins and peptides can be used in the DNA constructs of the instant invention. In general, a sequence that encodes a MtDef5 protein or peptide with at least about 85% sequence identity to any one of SEQ ID NOs:1, 3-9, 16-22, and 49-64 can be used. The encoded MtDef5 protein or peptide sequence of the DNA construct includes, but is not limited to, sequences that encode mature MtDef5 proteins. The encoded MtDef5 protein and peptide sequences of the DNA construct also include nucleic acid sequences that encode MtDef5 proproteins comprising a MtDef5 signal peptide and a mature MtDef5 protein. MtDef5.1a-5.6 proprotein sequences are shown in SEQ ID NOs:1 and 4-9. Proteins having at least 70% sequence identity to these sequences, and biological functional equivalents of these sequences, are encompassed by the present invention. The MtDef5 proteins and peptides encoded by the DNA construct can thus comprise the amino acid sequences shown in SEQ ID NOs:1, 3-9, 16-22, and 49-64. The mature MtDef5 proteins encoded by the DNA construct can also comprise the amino acid sequences shown in SEQ ID NOs:16-22.

In certain embodiments of the invention, the isolated DNA construct uses promoter and polyadenylation sequences that provide for expression of operably linked sequences when introduced into a transgenic plant. Sequences encoding MtDef5 proteins and peptides that are at least about 85% identical to any of SEQ ID NOs:1, 3-9, 16-22, and 49-64 are operably linked to the promoter and polyadenylation sequences that provide for expression in transgenic plants. The promoter that provides for expression in plants can be selected from the group consisting of a constitutive promoter, a tissue specific promoter, a stress induced promoter, a temporal promoter, and a fungal infection induced promoter. Constitutive promoters are selected from the group consisting of a CaMV35S promoter, a FMV35S promoter, a maize ubiquitin promoter, and a rice actin promoter. Polyadenylation sequences can be selected from the group consisting of a CaMV35S, a NOS, a rice lactate dehydrogenase, and a wheat Hsp17 polyadenylation sequence.

In other embodiments of the invention, the isolated DNA construct can further comprise an intron sequence that provides for expression of operably linked sequences when introduced into the nuclear genome of a plant and when the intron sequence is operably linked to the promoter, the sequence that encodes a signal peptide, the sequence that encodes a mature MtDef5 polypeptide, and the polyadenylation sequence. This intron sequence can be selected from the group comprising a rice actin intron, a maize hsp70 intron, a maize small subunit RUBISCO intron, a maize ubiquitin intron, a maizeAdh1 intron, a rice phenylalanine ammonia lyase intron, a sucrose synthase intron, a CAT-1 intron, a pKANNIBAL intron, the PIV2 intron and a Super Ubiquitin intron.

The DNA construct that provides for expression of a mature MtDef5 protein in plants can comprise a polynucleotide containing a maize ubiquitin promoter and intron, a synthetic MtDef5 gene encoding both an MtDef5 signal peptide and a mature MtDef5 protein and polyadenylation signal. Another DNA construct that provides for expression of a mature MtDef5 protein in plants can comprise a FMV promoter, a super ubiquitin intron, a genomic MtDef5 sequence encoding a signal peptide, an intron, and a mature MtDef5 protein, and a tNOS terminator. DNA constructs encompassed by the present invention include those that provide for MtDef5 protein or peptide expression in plants further comprising sequences encoding vacuolar targeting peptides or endoplasmic reticulum retention peptides that are operably linked to the MtDef5 protein or peptide. A DNA construct that provides for expression of a mature MtDef5 protein in plants can comprise a FMV promoter, a super ubiquitin intron, a genomic MtDef5 sequence encoding a signal peptide, an intron, and a mature MtDef5 protein that is operably linked to a vacuolar or endoplasmic reticulum targeting peptide, and a tNOS terminator The DNA constructs of the invention can further comprise a sequence encoding a selectable marker. This selectable marker is typically used to select transgenic plants containing the DNA construct. The selectable marker can be selected from the group consisting of a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichloro-phenoxyacetate monoxygenase protein, a methotrexate insensitive dihydrofolate reductase protein, and an aminoethylcysteine insensitive octopine synthase protein.

The DNA constructs of the invention can further comprise a sequence encoding a scoreable marker. This scoreable marker is typically used to identify transgenic plants containing the DNA construct. The scoreable marker can be selected from the group consisting of a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein, and a chloramphenicol acetyl transferase protein.

Transgenic plants comprising the aforementioned DNA constructs that express MtDef5 proteins and peptides in such plants are also provided by this invention. The transgenic plants can be food crop plants or biofuel crop plants, and either monocots or dicots. Transgenic monocot plants of the invention can be selected from the group consisting of barley, corn, flax, oat, rice, rye, sorghum, turf grass, sugarcane, and wheat. Transgenic dicot plants of the invention can be selected from the group consisting of alfalfa, *Arabidopsis*, barrel medic, banana, broccoli, bean, cabbage, canola, carrot, cassava, cauliflower, celery, citrus, cotton, a cucurbit, *eucalyptus*, garlic, grape, onion, lettuce, pea, peanut, pepper, potato, poplar, pine, sunflower, safflower, soybean, strawberry, sugar beet, sweet potato, tobacco, and tomato.

In other embodiments of the invention, the DNA construct uses a promoter and a polyadenylation sequence that provide for expression of operably linked sequences when introduced into a yeast cell. This promoter can be selected from the group consisting of an AOX1 promoter, an AOX2 promoter, a PHO promoter, a MOX promoter, a DAS promoter, an ADH promoter, a GAPDH promoter, and a LAC4 promoter. This polyadenylation sequence can selected from the group consisting of an AOX1, an AOX2, a CYC1, a p40, a p76, a MOX, a LAC4, and an actin polyadenylation sequence. The DNA construct can comprise a polynucleotide encoding an operably linked AOX1 promoter, yeast α-factor signal sequence, mature MtDef5 defensin sequence, and an AOX1 polyadenylation sequence. Alternatively, the DNA construct can comprise a polynucleotide encoding an operably linked AOX1 promoter, yeast α-factor signal sequence, mature MtDef5defensin sequence, and an AOX1 polyadenylation sequence.

DNA constructs for expression of mature MtDef5 proteins or peptides in yeast can further comprise a selectable or scoreable marker gene. The selectable marker gene can be selected from the group consisting of genes encoding a ADE protein, a HIS5 protein, a HIS4 protein, a LEU2 protein, a URA3 protein, a ARG4 protein, a TRP1 protein, a LYS2 protein, a protein conferring resistance to a bleomycin or phleomycin antibiotic, a protein conferring resistance to chloramphenicol, a protein conferring resistance to G418 or geneticin, a protein conferring resistance to hygromycin, a protein conferring resistance to methotrexate, an a ARO4-OFP protein, and a FZF1-4 protein.

The scoreable marker gene can be selected from the group consisting of genes encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein, and a chloramphenicol acetyl transferase protein.

Yeast cells comprising the aforementioned DNA constructs that comprise a promoter and a polyadenylation sequence that provide for expression of operably linked sequences encoding MtDef5 proteins and peptides in yeast are also provided by this invention. The yeast cells can be selected from the group consisting of *Candida, Kluveromyces, Hansuela, Pichia, Saccharomyces, Schizosaccharomyces*, and *Yarrowia*.

The present invention further provides for methods of obtaining transgenic plants capable of inhibiting growth of a plant pathogenic fungus. These methods comprise the steps of: introducing the DNA construct that provides for expression of a MtDef5 protein or peptide in a plant, plant cell, or plant tissue, and obtaining a transgenic plant comprising the DNA construct that expresses a plant pathogenic fungus inhibitory amount of a MtDef5 protein or peptide. To practice this method, the DNA construct can be introduced into the plant by a method selected, for example, from the group consisting of particle bombardment, DNA transfection, DNA electroporation, and T-DNA mediated transformation.

The DNA construct used in certain embodiments of this method can further comprise a selectable marker gene. When the DNA construct further comprises a selectable marker gene, a transgenic plant of the invention is obtained by growing the plant, plant cell, or plant tissue under conditions requiring expression of the selectable marker gene for plant growth. This selectable marker gene can be selected from the group consisting of genes encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein.

These methods of obtaining transgenic plants can also employ DNA constructs that further comprise a scoreable marker gene that functions in plants. In this case, expression of the scoreable marker gene is assayed to obtain a transgenic plant cell or a regenerated transgenic plant. Scoreable marker genes can be selected from the group consisting of genes encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein, and a chloramphenicol acetyl transferase protein.

In this method, a transgenic plant that expresses a plant pathogenic fungus inhibitory amount of the mature MtDef5 protein or peptide can be obtained by assaying expression of a MtDef5 encoding transgene in the transgenic plant. Expression of the MtDef5 encoding transgene can be assayed by a method selected from, for example, the group consisting of an immunoassay, an enzyme-linked immunoassay, an assay based on detection by RNA hybridization, and an assay based on detection by a reverse-transcriptase polymerase chain reaction. Alternatively, the expression of the MtDef5 encoding transgene is assayed by exposing the transgenic plant to a plant pathogenic fungus and determining if growth of the plant pathogenic fungus is inhibited. A plant pathogenic fungus inhibitory amount of mature MtDef5 protein is at least about 0.05 PPM, about 0.5 PPM, about 1.0 PPM, or about 2.0 PPM, where PPM is "parts per million" of MtDef5 protein present in fresh weight plant tissue. Typically, microgram amounts of MtDef5 protein are present per gram fresh weight of transgenic plant tissue. In preferred embodiments, the plant pathogenic fungus inhibitory amount of MtDef5 protein is at least about 0.5 PPM. In more preferred embodiments, the plant pathogenic fungus inhibitory amount of MtDef5 is at least about 1.0 PPM. In the most preferred embodiments, the plant pathogenic fungus inhibitory amount of MtDef5 is at least about 2.0 PPM.

This method provides for inhibition of the growth of a variety of MtDef5 molecule-susceptible plant pathogenic fungi. Plant pathogenic fungi inhibited by the method can be selected from the group consisting of an *Alternaria* sp., an *Ascochyta* sp., an *Aspergillus* sp., a *Botrytis* sp.; a *Cercospora* sp., a *Colletotrichum* sp., a *Diplodia* sp., an *Erysiphe* sp., a *Fusarium* sp., *Gaeumannomyces* sp., *Helminthosporium* sp., *Macrophomina* sp., a *Nectria* sp., a *Peronospora* sp., a *Phakopsora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp., a *Pythium* sp., a *Rhizoctonia* sp., a *Scerotium* sp., a *Sclerotinia* sp., a *Septoria* sp., a *Thielaviopsis* sp., an *Uncinula* sp., a *Venturia* sp., and a *Verticillium* sp.

The present invention also provides for transgenic plants capable of inhibiting the growth of a plant pathogenic fungus that are produced by the methods described herein. Transgenic plants produced by a process comprising the steps of introducing a DNA construct of the invention into a plant, a plant cell, or a plant tissue and obtaining a transgenic plant comprising the DNA construct that expresses a plant pathogenic fungus inhibitory amount of a MtDef5 protein or peptice are also thus contemplated by this invention. A plant pathogenic fungus inhibitory amount of mature MtDef5 protein or peptide is at least about 0.05 PPM, 0.5 PPM, 1.0 PPM, or 2.0 PPM, where PPM is "parts per million" of MtDef5 protein present in fresh weight plant tissue.

The instant invention further provides for methods of producing a MtDef5 protein or peptide that has at least about 85% sequence identity to the amino acid sequences shown in SEQ ID NOs:1, 3-9, 16-22, and 49-64. The methods for producing the mature MtDef5 protein or peptide comprise the steps of culturing a yeast cell comprising a DNA construct that provides for expression of a MtDef5 protein or peptide in yeast under conditions wherein the yeast cell expresses a MtDef5 protein or peptide, and isolating the MtDef5 protein or peptide from the culture of the preceding step. The MtDef5 protein or peptide can be isolated in the second step from the cell culture medium. Alternatively, the MtDef5 protein or peptide can be isolated from the yeast cells. In certain embodiments of this method, the MtDef5 protein is a mature MtDef5 protein. The yeast cell used in this method can be a *Pichia* cell that comprises a DNA construct containing an AOX1 promoter that is operably linked to a sequence encoding a signal peptide and a sequence encoding a mature MtDef5 protein, and the conditions that provide for expression of the mature MtDef5 protein would comprise culturing the *Pichia* cell in the presence of methanol.

The present invention also provides for an antibody that recognizes a MtDef5 protein or peptide having at least about 85% sequence identity to any one of sequences SEQ ID NOs:1, 3-9, 16-22, and 49-64. Kits for specifically detecting a MtDef5 protein or peptide with at least about 85% sequence identity to any one of SEQ ID NOs:1, 3-9, 16-22, and 49-64, comprising the antibody that recognizes a MtDef5 protein or peptide with at least about 85% sequence identity to any one of SEQ ID NOs:1, 3-9, 16-22, and 49-64 and a reagent for detecting the antibody, are also provided by this invention.

Certain isolated nucleotide sequences are also provided by this invention. The isolated nucleotide sequences of the invention comprise a MtDef5 coding sequence selected from the group consisting of SEQ ID NOs:10-15, 23-29, and 65-78, and a MtDef5 or other signal peptide coding sequence selected from the group consisting of SEQ ID NOs:30-35 and 42-48. Oligo-nucleotides derived from the above sequences are further contemplated. Such oligonucleotides can be used to identify transgenic plants containing the noted nucleotide sequences, or to identify material obtained from these transgenic plants. Methods for using these oligonucleotides to identify the transgenic plant materials and kits for performing these methods are also contemplated.

Various isolated, purified MtDef5 proprotein, mature, and peptide sequences are also provided by this invention as variously shown in SEQ ID NOs:1, 3-9, 16-22, and 49-64, as well as coding sequences therefor as shown in SEQ ID NOs:10-15, 23-29, and 65-78, respectively, as noted above.

DNA Constructs Comprising Plant Expression Cassettes

The construction of expression cassettes for use in monocotyledonous or dicotyledonous plants is well established. Expression cassettes are DNA constructs wherein various promoter, coding, and polyadenylation sequences are operably linked. In general, expression cassettes typically comprise a promoter that is operably linked to a sequence of interest, which is operably linked to a polyadenylation or terminator region. In certain instances including, but not limited to, the expression of transgenes in monocot plants, it may also be useful to include an intron sequence. When an intron sequence is included it is typically placed in the 5' untranslated leader region of the transgene. In certain instances, it may also be useful to incorporate specific 5' untranslated sequences in a transgene to enhance transcript stability or to promote efficient translation of the transcript.

Promoters

A variety of promoters can be used in the practice of this invention. One broad class of useful promoters are referred to as "constitutive" promoters in that they are active in most plant organs throughout plant development. For example, the promoter can be a viral promoter such as a CaMV35S or FMV35S promoter. The CaMV35S and FMV35S promoters are active in a variety of transformed plant tissues and most plant organs (e.g., callus, leaf, seed and root). Enhanced or duplicate versions of the CaMV35S and FMV35S promoters are particularly useful in the practice of this invention (U.S. Pat. No. 5,378,619, incorporated herein by reference in its entirety). Other useful promoters include the nopaline synthase (NOS) and octopine synthase (OCS) promoters (which are carried on tumor-inducing plasmids of *A. tumefaciens*), the cauliflower mosaic virus (CaMV) 19S promoters, a maize ubiquitin promoter, the rice Act1 promoter, and the Figwort Mosaic Virus (FMV) 35S promoter (see, e.g., U.S. Pat. No. 5,463,175, incorporated herein by reference in its entirety). It is understood that this group of exemplary promoters is non-limiting and that one skilled in the art could employ other promoters that are not explicitly cited here in the practice of this invention.

Promoters that are active in certain plant tissues (i.e., tissue specific promoters) can also be used to drive expression of MtDef5 proteins and peptides. Expression of MtDef5 proteins and peptides in the tissue that is typically infected by a fungal pathogen is anticipated to be particularly useful. Thus, expression in reproductive tissues, seeds, roots, stems, or leaves can be particularly useful in combating infection of those tissues by certain fungal pathogens in certain crops. Examples of useful tissue-specific, developmentally regulated promoters include but are not limited to the 0-conglycinin 7S promoter (Doyle et al., 1986), seed-specific promoters (Lam and Chua, 1991), and promoters associated with napin, phaseolin, zein, soybean trypsin inhibitor, ACP, stearoyl-ACP desaturase, or oleosin genes. Examples of root specific promoters include but are not limited to the RB7 and RD2 promoters described in U.S. Pat. Nos. 5,459,252 and 5,837,876, respectively.

Another class of useful promoters are promoters that are induced by various environmental stimuli. Promoters that are induced by environmental stimuli include, but are not limited to, promoters induced by heat (e.g., heat shock promoters such as Hsp70), promoters induced by light (e.g., the light-inducible promoter from the small subunit of ribulose 1,5-bisphosphate carboxylase, ssRUBISCO, a very abundant plant polypeptide), promoters induced by cold (e.g., COR promoters), promoters induced by oxidative stress (e.g., catalase promoters), promoters induced by drought (e.g., the wheat Em and rice rab16A promoters), and promoters induced by multiple environmental signals (e.g., rd29A promoters, Glutathione-S-transferase (GST) promoters).

Promoters that are induced by fungal infections in plants can also be used to drive expression of MtDef5 proteins and peptides. Useful promoters induced by fungal infections include those promoters associated with genes involved in phenylpropanoid metabolism (e.g., phenylalanine ammonia lyase, chalcone synthase promoters), genes that modify plant cell walls (e.g., hydroxyproline-rich glycoprotein, glycine-rich protein, and peroxidase promoters), genes encoding enzymes that degrade fungal cell walls (e.g., chitinase or glucanase promoters), genes encoding thaumatin-like protein promoters, or genes encoding proteins of unknown function that display significant induction upon fungal infection. Maize and flax promoters, designated as Mis1 and Fis1, respectively, are also induced by fungal infections in plants and can be used (U.S. Patent Application 20020115849).

Depending on the fungus to which protection is sought, the present MtDef5 proteins and peptides can be expressed in any tissue or organ in the plant where the fungus attacks. In the case of *Fusarium* for example, a preferred site for expression is in the roots. In the case of those fungi that infect by entering external plant surfaces, accumulation of the MtDef5 proteins and peptides in the apoplast is preferred, and these molecules can be expressed in roots, stems, leaves, etc., by the use of tissue-specific promoters.

Promoters active at particular developmental stages in the plant life cycle can also be used to optimize resistance to fungal infection and/or damage when it is most needed.

Introns

An intron can also be included in the DNA expression construct, especially in instances when the sequence of interest is to be expressed in monocot plants. For monocot plant use, introns such as the maize hsp70 intron (U.S. Pat. No. 5,424,412; incorporated by reference herein in its entirety), the maize ubiquitin intron, the Adh intron 1 (Callis et al., 1987), the sucrose synthase intron (Vasil et al., 1989) or the rice Act1 intron (McElroy et al., 1990) can be used. Dicot plant introns that are useful include introns such as the CAT-1 intron (Cazzonnelli and Velten, 2003), the pKAN-NIBAL intron (Wesley et al., 2001; Collier et al., 2005), the PIV2 intron (Mankin et al., 1997) and the "Super Ubiquitin" intron (U.S. Pat. No. 6,596,925, incorporated herein by reference in its entirety; Collier et al., 2005) that have been operably integrated into transgenes. It is understood that this group of exemplary introns is non-limiting and that one skilled in the art could employ other introns that are not explicitly cited here in the practice of this invention.

Certain embodiments of this invention comprise a sequence encoding a signal peptide that facilitates secretion of the mature MtDef5 proteins or peptides from plant cells. Portions of the MtDef5.1a-5.6 cDNAs (SEQ ID NOs:1 and 4-9) contain sequences (SEQ ID NOs:30-35) that encode MtDef5 signal peptides that can be used for secreting MtDef5 proteins or peptides from plant or other cells.

MtDef5 signal peptide-encoding sequences can be used in the DNA constructs of the invention in a variety of ways. These MtDef5 signal sequences can be the MtDef5 signal sequences that are associated with a given MtDef5 proprotein coding sequence in a given MtDef5 cDNA or genomic clone. Alternatively, the MtDef5 signal peptide can be operably linked to a distinct mature MtDef5 protein (or MtDef5 peptide) encoding sequence (i.e., MtDef5 signal peptide and mature protein (or peptide) encoding sequences derived from distinct genomic or cDNA clones can be operably linked). In the DNA constructs, nucleotide sequences encoding any MtDef5 proprotein comprising both a MtDef5 signal peptide and a mature MtDef5 protein can also be used instead of two distinct signal peptide and mature MtDef5 protein encoding sequences. MtDef5 proproteins encoded by these sequences include, but are not limited to, MtDef5 proprotein sequences including SEQ ID NOs:1 and 4-9, proteins that have at least about 70% sequence identity to these sequences, and the biological functional equivalents of these sequences. It is anticipated that the MtDef5 signal peptides can be used to secrete mature MtDef5 proteins and peptices from either monocot or dicot plant cells. Synthetic nucleotide sequences that encode the MtDef5 signal peptide sequences can also be used. Such synthetic sequences can be deduced from the MtDef5 signal peptide sequences disclosed herein through application of the genetic code. Table 1 provides a list of MtDef5 and other signal peptides that can be used to secrete mature MtDef5 or other proteins from cells.

TABLE 1

MtDef5 and MtDef4 Signal Peptide Sequences

| SEQ ID NO: | Amino Acid Sequence | Source |
|---|---|---|
| SEQ ID NO: 30 | MTSSASKFYTIFIFV CLAFLFISTSEVEA | MtDef5.1a-5.1b |
| SEQ ID NO: 31 | MASSSPKLFTIFLFL ILVVLLFSTSEVQA | MtDef5.2 |
| SEQ ID NO: 32 | MTSSATKFYTIFVFV CLALLLISICEVEA | MtDef5.3 |
| SEQ ID NO: 33 | MASSTLKFNTIFLFL SLALLLFFTLEVQG | MtDef5.4 |
| SEQ ID NO: 34 | MASSALKYYTFFLFF ILALILLPTLEVQG | MtDef5.5 |
| SEQ ID NO: 35 | MVCTEVQA | MtDef5.6 |

TABLE 1-continued

MtDef5 and MtDef4 Signal Peptide Sequences

| SEQ ID NO: | Amino Acid Sequence | Source |
|---|---|---|
| SEQ ID NO: 48 | MARSVPLVSTIFVFL LLLVATGPSMVAEA | MtDef4 signal peptide consensus |
| SEQ ID NO: 42 | MARSVPLVSTIFVFL LLLVATGPSMVAEA | MtDef4.1(H33R) |
| SEQ ID NO: 43 | MARSVPLVSTIFVFFL LIVATEMGPSMVAA | MtDef4.2 |
| SEQ ID NO: 44 | MARSVPLVSTIFVFFL LLVATEMGPIMVAEA | MtDef4.3 |
| SEQ ID NO: 45 | MARSVFLVSTIFVFLL VLVATGPSMVAEA | AL385796* |
| SEQ ID NO: 46 | MARSVSLVFTIFVFLL LVVATGPSMVAEA | AW573770* |
| SEQ ID NO: 47 | MARSVPLVSTIFVFLL LLVATGPSMVGEA | BE999096* |

*GenBank Accession Number (including signal and mature peptide sequences)

Alternatively, signal peptide sequences derived from other *Medicago* defensin proteins (Hanks et al, 2005) can be used. Examples of such other *Medicago* defensin protein signal peptides include, but are not limited to, signal peptides of MtDef1.1, MsDef1.6, and MtDef2.1. Another example of a useful signal peptide encoding sequence that can be used in monocot plants is the signal peptide derived from a barley cysteine endoproteinase gene (Koehler and Ho, 1990). Another example of a useful signal peptide encoding sequence that can be used in dicot plants is the tobacco PR1b signal peptide. This group of signal peptides is meant to be exemplary and non-limiting, and one skilled in the art could employ other signal peptides in the practice of the present invention that are not explicitly cited here.

In the present invention, a sequence encoding a mature MtDef5 protein or peptide is typically linked to the signal peptide encoding sequence. A variety of DNA sequences encoding a variety of mature MtDef5 proteins and peptides can be used in practicing this invention. The DNA sequence can encode mature MtDef5 proteins and peptides that include, but are not limited to, the amino acid sequences shown in SEQ ID NOs:16-22 and 49-64, and biological functional equivalents of any of the foregoing amino acid sequences. Biological functional equivalents of an MtDef5 proprotein, mature protein, or peptide also include, but are not limited to, MtDef5 proproteins, mature proteins, and peptides with at least about 85% sequence identity to any of SEQ ID NOs:1, 3-9, 16-22, and 49-64. In certain embodiments of the invention, a mature MtDef5 protein- or peptide-encoding sequence can be physically derived or obtained from either genomic DNA or cDNA obtained from *Medicago truncatula* plant tissue. Such methods for obtaining similar defensin genes from *Medicago truncatula* have been described (Hanks et al, 2005). The native or endogenous MtDef5-encoding nucleotide sequence is derived from a dicotyledonous plant in which it is ordinarily expressed under the control of the endogenous MtDef5 promoter sequence. Consequently, it is expected that the endogenous or naturally occurring MtDef5-encoding nucleotide sequence can be expressed in plants. In general, nucleic acids that encode MtDef5 proteins and peptides can be obtained from MtDef5 consensus nucleotide sequences, from synthetic MtDef5 genes derived by "back-translation" of MtDef5 polypeptide sequences, from genomic clones, from deduced coding sequences derived from genomic clones, from cDNA or EST sequences, and from any of the foregoing sequences that have been subjected to mutagenesis. Examples of nucleic acids that contain mature MtDef5 protein-encoding nucleotide sequences include, but are not limited to, SEQ ID NOs:10-15 and 23-29. Nucleotide sequences encoding various MtDef5 proteins and peptides can also be obtained from genomic sequences by removing deduced intron sequences to obtain the deduced MtDef5 coding sequences for MtDef5 proteins and peptides. Removal of the intron sequences from MtDef5 genomic clones can be effected by in vitro mutagenesis techniques. Alternatively, the intron sequences can be removed in silico (in a computer file) and the resultant deduced coding sequence synthesized by standard DNA synthesis techniques. It should also be noted that the closely related plant *Medicago sativa* may be a source of MsDef4 ESTs that encode MsDef4 proteins that are either identical to, or otherwise biologically equivalent to, the MtDef5 proteins ands and peptides of the present invention. Nucleotide sequences encoding the MtDef5 proteins and peptides of this invention can thus also be derived from other *Medicago* sp. such as *Medicago sativa*, and can be used in this invention. Portions of the aforementioned nucleotide sequences containing the sequences that encode mature MtDef5 proteins and peptides can be operably linked to either the native MtDef5 signal peptide sequence to which they are ordinarily linked or to another signal peptide via standard recombinant DNA techniques, or by DNA synthesis methods.

In other embodiments of the invention, the MtDef5-encoding nucleotide sequence can be synthesized de novo from an MtDef5 protein or peptide sequence disclosed herein. The sequence of the MtDef5-encoding nucleotide sequence can be deduced from the MtDef5 protein or peptide sequence through use of the genetic code. Computer programs such as "BackTranslate" (GCG™ Package, Acclerys, Inc. San Diego, CA) can be used to convert a protein or peptide sequence to the corresponding nucleotide sequence that encodes the protein or peptide.

Furthermore, the synthetic MtDef5-encoding nucleotide sequence can be designed so that it will be optimally expressed in plants. U.S. Pat. No. 5,500,365 describes a method for synthesizing plant genes to optimize the expression level of the protein encoded by the synthesized gene. This method relates to the modification of the structural gene sequences of the exogenous transgene, to make them more "plant-like" and therefore more efficiently transcribed, processed, translated, and expressed by the plant. Features of genes that are expressed well in plants include use of codons that are commonly used by the plant host and elimination of sequences that can cause undesired intron splicing or polyadenylation in the coding region of a gene transcript. A similar method for obtaining enhanced expression of transgenes in monocotyledonous plants is disclosed in U.S. Pat. No. 5,689,052. Furthermore, the synthetic design methods disclosed in U.S. Pat. Nos. 5,500,365 and 5,689,052 could also be used to synthesize a signal peptide encoding sequence that is optimized for expression in plants in general or monocot plants in particular.

In other embodiments of the invention, sequences encoding peptides that provide for the localization of an MtDef5 in subcellular organelles can be operably linked to the sequences that encode the MtDef5 protein or peptide. MtDef5 proteins and peptides that are operably linked to a signal peptide are expected to enter the secretion pathway and can be retained by organelles such as the endoplasmic reticulum (ER) or targeted to the vacuole by operably linking the appropriate retention or targeting peptides to the C-terminus of the MtDef5 protein or peptide. Examples of vacuolar targeting peptides include, but are not limited to, a CTPP vacuolar targeting signal from the barley lectin gene. Examples of ER targeting peptides include, but are not limited to, a peptide comprising a KDEL amino acid sequence.

Localization of MtDef5 proteins and peptides in either the endoplasmic reticulum or the vacuole can provide for desirable properties such as increased expression in transgenic plants and/or increased efficacy in inhibiting fungal growth in transgenic plants.

As noted above, the sequence of interest can also be operably linked to a 3' non-translated region containing a polyadenylation signal. This polyadenylation signal provides for the addition of a polyadenylate sequence to the 3' end of the RNA. The *Agrobacterium* tumor-inducing (Ti) plasmid nopaline synthase (NOS) gene 3' and the pea ssRUBISCO E9 gene 3' un-translated regions contain polyadenylate signals and represent non-limiting examples of such 3' untranslated regions that can be used in the practice of this invention. It is understood that this group of exemplary polyadenylation regions is non-limiting and that one skilled in the art could employ other polyadenylation regions that are not explicitly cited here in the practice of this invention.

The DNA constructs that comprise the plant expression cassettes described above are typically maintained in various vectors. Vectors contain sequences that provide for the replication of the vector and covalently linked sequences in a host cell. For example, bacterial vectors will contain origins of replication that permit replication of the vector in one or more bacterial hosts. *Agrobacterium*-mediated plant transformation vectors typically comprise sequences that permit replication in both *E. coli* and *Agrobacterium* as well as one or more "border" sequences positioned so as to permit integration of the expression cassette into the plant chromosome. Such *Agrobacterium* vectors can be adapted for use in either *Agrobacterium tumefaciens* or *Agrobacterium rhizogenes*. Selectable markers encoding genes that confer resistance to antibiotics are also typically included in the vectors to provide for their maintenance in bacterial hosts.

Methods for Obtaining Antifungal Plants

Methods of obtaining a transgenic plant capable of inhibiting growth of a plant pathogenic fungus are also provided by this invention. First, expression vectors suitable for expression of the MtDef5 protein or peptide in various dicot and monocot plants are introduced into a plant, a plant cell, a protplast, or a plant tissue using transformation techniques as described herein. Next, a transgenic plant containing or comprising the MtDef5 expression vector is obtained by regenerating that transgenic plant from the plant, plant cell, protoplast, or plant tissue that received the expression vector. The final step is to obtain a transgenic plant that expresses a plant pathogenic fungus inhibitory amount of the mature MtDef5 protein or peptide, where a "plant pathogenic fungus inhibitory amount" is a level of MtDef5 protein or peptide sufficient to provide any measurable decrease in fungal growth in the transgenic plant and/or any measurable decrease in the adverse effects caused by fungal growth in the transgenic plant.

Any of the MtDef5 expression vectors can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. The aforementioned methods of introducing transgenes are well known to those skilled in the art and are described in U.S. Patent Application No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton), each of which are incorporated herein by reference in their entirety. Methods of using bacteria such as *Rhizobium* or *Sinorhizobium* to transform plants are described in Broothaerts, et al., Nature. 2005,10; 433(7026):629-33. It is further understood that the MtDef5 expression vector can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the expression vector into the chromosome of a plant cell, a protoplast, a plant tissue, or a plant.

Methods of introducing plant minichromosomes comprising plant centromeres that provide for the maintenance of the recombinant minichromosome in a transgenic plant can also be used in practicing this invention (U.S. Pat. No. 6,972,197). In these embodiments of the invention, the transgenic plants harbor the minichromosomes as extrachromosomal elements that are not integrated into the chromosomes of the host plant.

Transgenic plants are typically obtained by linking the gene of interest (in this case an MtDef5-encoding nucleotide sequence) to a selectable marker gene, introducing the linked transgenes into a plant cell, a protoplast, a plant tissue, or a plant by any one of the methods described above, and regenerating or otherwise recovering the transgenic plant under conditions requiring expression of the selectable marker gene for plant growth. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, or an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection).

Transgenic plants can also be obtained by linking a gene of interest (in this case an MtDef5-encoding nucleotide sequence) to a scoreable marker gene, introducing the linked transgenes into a plant cell by any one of the methods described above, and regenerating the transgenic plants from transformed plant cells that test positive for expression of the scoreable marker gene. The scoreable marker gene can be a gene encoding a beta-glucuronidase protein, a green fluorescent protein, a yellow fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein, or a chloramphenicol acetyl transferase protein.

When the expression vector is introduced into a plant cell or plant tissue, the transformed cells or tissues are typically regenerated into whole plants by culturing these cells or tissues under conditions that promote the formation of a whole plant (i.e., the process of regenerating leaves, stems, roots, and, in certain plants, reproductive tissues). The development or regeneration of transgenic plants from either single plant protoplasts or various explants is well known in the art (Horsch, R. B. et al. 1985). This regeneration and growth process typically includes the steps of selection of transformed cells and culturing selected cells under conditions that will yield rooted plantlets. The resulting transgenic rooted shoots are thereafter planted in an appropriate plant growth medium such as soil. Alternatively, transgenes can also be introduced into isolated plant shoot meristems and plants regenerated without going through callus stage tissue culture (U.S. Pat. No. 7,002,058). When the transgene is introduced directly into a plant, or more specifically into the meristematic tissue of a plant, seed can be harvested from the plant and selected or scored for presence of the transgene. In the case of transgenic plant species that reproduce sexually, seeds can be collected from plants that have been "selfed" (self-pollinated) or out-crossed (i.e., used as a pollen donor or recipient) to establish and maintain the transgenic plant line. Transgenic plants that do not sexually reproduce can be vegetatively propagated to establish and maintain the transgenic plant line. As used herein, "transgenic plant line" refers to transgenic plants derived from a transformation event where the transgene has inserted into one or more locations in the plant genome. In a related aspect, the present invention also encompasses a seed produced by the transformed plant, a progeny from such seed, and a seed produced by the progeny of the original transgenic plant, produced in accordance with the above process. Such progeny and seeds will have an MtDef5 protein- or peptide-encoding transgene stably incorporated into their genome, and such progeny plants will inherit the traits afforded by the introduction of a stable transgene in Mendelian fashion. All such transgenic plants having incorporated into their genome transgenic DNA segments encoding one or more MtDef5 proteins or peptide are aspects of this invention. It is further recognized that transgenic plants containing the DNA constructs described herein, and materials derived therefrom, may be identified through use of PCR or other methods that can specifically detect the sequences in the DNA constructs.

Identification of Transgenic Plants and Quantitation of MtDef5 Expression

Once a transgenic plant is regenerated or recovered, a variety of methods can be used to identify or obtain a transgenic plant that expresses a plant pathogenic fungus inhibitory amount of MtDef5. One general set of methods is to perform assays that measure the amount of MtDef5 that is produced. For example, various antibody-based detection methods employing antibodies that recognize MtDef5 can be used to quantitate the amount of MtDef5 produced. Examples of such antibody-based assays include, but are not limited to, ELISAs, RIAs, or other methods wherein an MtDef5-recognizing antibody is detectably labelled with an enzyme, an isotope, a fluorophore, a lanthanide, and the like. By using purified or isolated MtDef5 protein or peptide as a reference standard in such assays (i.e., providing known amounts of MtDef5), the amount of MtDef5 present in the plant tissue in a mole per gram of plant material or mass per gram of plant material can be determined. The MtDef5 protein or peptide will typically be expressed in the transgenic plant at the level of "parts per million" or "PPM", where microgram levels of MtDef5 are present in gram amounts of fresh weight plant tissue. In this case, 1 microgram of MtDef5 per 1 gram of fresh weight plant tissue would represent a MtDef5 concentration of 1 PPM. A plant pathogenic fungus inhibitory amount of MtDef5 protein or peptide is at least about 0.05 PPM (i.e., 0.05 µg MtDef5 protein or peptide per gram fresh weight plant tissue). In preferred embodiments, a plant pathogenic fungus inhibitory amount of MtDef5 is at least about 0.5 PPM. In more preferred embodiments, the amount of MtDef5 is at least about 1.0 PPM. In the most preferred embodiments, the amount of MtDef5 protein or peptide is at least about 2.0 PPM.

Alternatively, the amount of MtDef5-encoding mRNA produced by the transgenic plant can be determined to identify plants that express plant pathogenic fungus inhibitory amounts of MtDef5. Techniques for relating the amount of protein produced to the amount of RNA produced are well known to those skilled in the art and include methods such as constructing a standard curve that relates specific RNA levels (i.e., MtDef5 mRNA) to levels of the MtDef5 protein or peptide (determined by immunologic or other methods). Methods of quantitating MtDef5 mRNA typically involve specific hybridization of a polynucleotide to either the MtDef5 mRNA or to a cDNA (complementary DNA) or PCR product derived from the MtDef5 RNA. Such polynucleotide probes can be derived from either the sense and/or antisense strand nucleotide sequences of the MtDef5-encoding transgene. Hybridization of a polynucleotide probe to the MtDef5 mRNA or cDNA can be detected by methods including, but not limited to, use of probes labelled with an isotope, a fluorophore, a lanthanide, or a hapten such as biotin or digoxigenin. Hybridization of the labelled probe can be detected when the MtDef5 RNA is in solution or immobilized on a solid support such as a membrane. When quantitating MtDef5 RNA by use of a quantitative reverse-transcriptase Polymerase Chain Reaction (qRT-PCR), the MtDef5-derived PCR product can be detected by use of any of the aforementioned labelled polynucleotide probes, by use of an intercalating dye such as ethidium bromide or SYBR green, or use of a hybridization probe containing a fluorophore and a quencher such that emission from the fluorophore is only detected when the fluorophore is released by the 5' nuclease activity of the polymerase used in the PCR reaction (i.e., a TaqMan™ reaction; Applied Biosystems, Foster City, CA) or when the fluorophore and quencher are displaced by polymerase mediated synthesis of the complementary strand (i.e., Scorpion™ or Molecular Beacon™ probes). Various methods for conducting qRT-PCR analysis to quantitate mRNA levels are well characterized (Bustin, S. A.; 2002). Fluorescent probes that are activated by the action of enzymes that recognize mismatched nucleic acid complexes (i.e., Invader™, Third Wave Technologies, Madison, WI) can also be used to quantitate RNA. Those skilled in the art will also understand that RNA quantitation techniques such as Quantitative Nucleic Acid Sequence Based Amplification (Q-NASBA™) can be used to quantitate MtDef5-encoding mRNA and identify expressing plants.

Transgenic plants that express plant pathogenic fungus inhibitory amounts of MtDef5 proteins or peptides can also be identified by directly assaying such plants for inhibition of the growth of a plant pathogenic fungus. Such assays can be used either independently or in conjunction with MtDef5 expression assays to identify the resistant transgenic plants. Infection of certain plants with certain plant pathogen fungi can result in distinctive effects on plant growth that are readily observed. Consequently, one can distinguish MtDef5-expressing transgenic plants by simply challenging such plants transformed with MtDef5-encoding transgenes with pathogenic plant fungi and observing reduction of the symptoms normally associated with such infections. Such observations are facilitated by co-infecting otherwise identical, non-transgenic control plants that do not contain an MtDef5 encoding transgene with the same type and dose of plant pathogenic fungi used to infect the transgenic plants that contain an MtDef5-encoding transgene. Identification of transgenic plants that control or combat fungal infection can be based on observation of decreased disease symptoms, measurement of the decreased fungal growth in the infected plant (e.g., by determining the numbers of colony forming units per gram of infected tissue) and/or by measurement of the amount of mycotoxins present in infected plant tissue. The use of fungal disease severity assays and colony formation assays in conjunction with expression assays to identify transgenic MsDef1-expressing potato plants that are resistant to *Verticillium dahliae* has been described (U.S. Pat. No. 6,916,970 and Gao et al, 2000). It is similarly anticipated that a variety of MtDef5-expressing transgenic plants that combat or control fungal pathogens can be identified by scoring transgenic plants for resistance to fungal pathogens that infect those plants. Examples of MtDef5 transgene-conferred fungal resistance that can be assayed by observing reductions in disease symptoms or reductions in fungal growth include, but are not limited to, resistance of transgenic corn to *Fusarium verticilihoides, Fusarium moniliforme, Stenocarpella maydis*, and/or *Cercospora zeae-maydis*; resistance of transgenic wheat to head blight (*Fusarium graminearum*), powdery mildew (*Erysiphe graminis* f. sp. *tritici*), or leaf rust (*Puccinia recondita* f. sp. *tritici*); resistance of transgenic cotton to *Fusarium oxysporum*; resistance of transgenic rice to *Magnaporthe grisea* and *Rhizoctonia solani*, and resistance of transgenic soybean to Asian Soybean rust (*Phakopsora pachyrhizi*), Phytophthora Root Rot (*Phytophthora* sp.), White Mold (*Sclerotinia* sp.), Sudden Death Syndrome (*Fusarium solani*) and/or Brown Stem Rot (*Phialophora gregata*).

Transgenic plants that express plant pathogenic fungus inhibitory amounts of MtDef5 can also be identified by measuring decreases in the adverse effects cause by fungal growth in such plants. Such decreases can be ascertained by comparing the extent of the adverse effect in an MtDef5-expressing transgenic plant relative to an otherwise identical, non-transgenic control plant that does not express MtDef5. Adverse effects of fungal growth in a plant that can be measured include any type of plant tissue damage or necrosis, any type of plant yield reduction, any reduction in the value of the crop plant product, and/or production of undesirable fungal metabolites or fungal growth by-products including, but not limited to, mycotoxins. Mycotoxins comprise a number of toxic molecules produced by fungal species, including but not limited to polyketides (including aflatoxins, demethylsterigmatocystin, O-methylsterigmatocystin, etc.), fumonisins, alperisins (e.g., $A_1$, $A_2$, $B_1$, $B_2$), sphingofungins (A, B, C and D), trichothecenes, fumifungins, and the like. Methods of quantitating mycotoxin levels are widely documented. Moreover, commercial kits for measurement of the mycotoxins such as aflatoxin, fumonisin, deoxynivalenol, and zearalenone are also available (VICAM, Watertown, MA, USA).

Target Plants/Plants of Interest

A wide variety of plants can be transformed with MtDef5-expressing vectors to obtain transgenic plants that combat or control fungal infections, or that resist such infections. Plants of interest include both food crop plants and biofuels or energy crop plants, as listed above. Transgenic monocot plants obtainable by the expression vectors and methods described herein include but are not limited to barley, corn, flax, oat, rice, rye, sorghum, turf grass, sugarcane, and wheat. Transgenic dicot plants obtainable by the expression vectors and methods described herein include but are not limited to alfalfa, *Arabidopsis*, barrel medic, banana, broccoli, bean, cabbage, canola, carrot, cassava, cauliflower, celery, citrus, cotton, cucurbits, *eucalyptus*, garlic, grape, onion, lettuce, pea, peanut, pepper, potato, poplar, pine, sunflower, safflower, soybean, strawberry, sugar beet, sweet potato, tobacco, and tomato.

Stacked Genes: Multiple Resistances

Simultaneous co-expression of multiple antifungal and/or other anti-pathogen proteins in plants is advantageous in that it exploits more than one mode of control of plant pathogens. This may, where two or more antifungal proteins are expressed, minimize the possibility of developing resistant fungal species, broaden the scope of resistance, and potentially result in a synergistic antifungal effect, thereby enhancing the level of resistance.

Other proteins conferring certain advantages that can be co-expressed with the DNAs encoding the MtDef5 molecules of the present invention include: (1) DNAs encoding enzymes such as glucose oxidase (which converts glucose to gluconic acid, concomitantly producing hydrogen peroxide which confers broad spectrum resistance to plant pathogens); pyruvate oxidase; oxalate oxidase; cholesterol oxidase; amino acid oxidases; and other oxidases that use molecular oxygen as a primary or secondary substrates to produce peroxides, including hydrogen peroxide; (2) pathogenesis-related proteins such as SAR8.2a and SAR8.2b proteins; the acidic and basic forms of tobacco PR-1a, PR-1b, PR-1c, PR-1', PR-2, PR-3, PR-4, PR-5, PR-N, PR-O, PR-O', PR—P, PR-Q, PR-S, and PR-R proteins; chitinases such as tobacco basic chitinase and cucumber chitinase/lysozyme; peroxidases such as cucumber basic peroxidase; glucanases such as tobacco basic glucanase; osmotin-like proteins; (3) viral capsid proteins and replicases of plant viruses; (4) plant R-genes (resistance genes) and homologs thereof, including but not limited to *Arabidopsis* RPS2 (Bent et al., 1994), *Arabidopsis* RPM1 (Grant et al., 1995), tobacco N-gene and N'-gene, tomato Cf-9, flax L6, and rice Xa21; (5) pathogen Avr genes, such as *Cladosporium fulvum* Avr9, that can be expressed using pathogen- or chemical-inducible promoters; (6) genes that are involved in the biosynthesis of salicylic acid, such as benzoic acid 2-hydroxylase; and (7) other defensin proteins with antifungal modes-of-action distinct from the mode-of-action of MtDef5 including, but not limited to, MsDef1, MtDef2, NaD1, Rs-AFP1 and Rs-AFP2. Other antifungal proteins that can be co-expressed in transgenic plants with the present MtDef5 defensins to confer resistance to fungal pathogen infections include the KP4 and KP6 proteins.

Co-expression of insect and herbicide resistance genes in transgenic plants expressing MtDef5 proteins and peptides confers even further agricultural benefits. The genomes of such transgenic plants can therefore further comprise:

DNA encoding a plant defensin selected, for example, from the group consisting of MsDef1, MtDef2, MtDef4, NaD1, Rs-AFP1, Rs-AFP2, KP4, and KP6, wherein such DNA is expressed and produces an anti-fungal effective amount of the defensin, and/or DNA encoding a *Bacillus thuringiensis* endotoxin, wherein such DNA is expressed and produces an anti-insect effective amount of the *Bacillus thuringiensis* endotoxin, and/or DNA encoding a protein that confers herbicide resistance to such plants, wherein such DNA is expressed and produces an anti-herbicide effective amount of the protein that confers herbicide resistance.

Yeast Expression Vectors and Transformation Systems

Expression of MtDef5 proteins and peptides in yeast is specifically contemplated herein. The construction of expression vectors for production of heterologous proteins in various yeast genera is well established. In general, such expression vectors typically comprise a promoter that is operably linked to a sequence of interest which is operably linked to a polyadenylation or terminator region. Examples of yeast genera that have been used to successfully express heterologous genes include *Candida, Kluveromyces, Hansuela, Pichia, Saccharomyces, Schizosaccharomyces*, and *Yarrowia*. A general description of expression vectors and transformation systems for *Saccharomyces* is found in Kingsman et al (1985). Expression vectors and transformation systems useful for yeasts other than *Saccharomyces* are described in Reiser et al (1990).

In general, the promoter and polyadenylation region are selected based on their operability in the desired yeast host. For example, the AOX1 or AOX2 promoters of *Pichia* can be used in conjunction with the AOX1, AOX2, p40, or p76 polyadenylation sequences of *Pichia* to express a heterologous protein such as an MtDef5 protein or peptide. Both the AOX1 and AOX2 promoters are particularly useful in *Pichia* as both promoters provide for abundant expression of the linked heterologous gene when induced by addition of methanol to the growth medium. The use of these *Pichia* promoters and polyadenylation sequences is described in U.S. Pat. No. 4,855,231, which is expressly incorporated herein by reference in its entirety.

Similarly, the *Hansuela* MOX, DHAS, or FMDH promoters can be used to express heterologous proteins such as MtDef5 in *Hansuela*. The MOX, DHAS, or FMDH promoters are particularly useful in *Hansuela* as these promoters provide for abundant expression of the linked heterologous gene when induced by addition of methanol to the growth medium. The use of the MOX and DHAS promoters in *Hansuela* is described in U.S. Pat. No. 5,741,672, while the use of the FMDH promoter in *Hansuela* is described in U.S. Pat. No. 5,389,525, each of which is expressly incorporated herein by reference in its entirety.

For *Kluveromyces*, a Lactase promoter and polyadenylation sequence can be used to express heterologous genes such as MtDef5. Expression of heterologous genes that are operably linked to the Lactase promoter and polyadenylation sequence is achieved by growing *Kluveromyces* in the presence of galactose. The use of the Lactase promoter and polyadenylation sequences in *Kluveromyces* is described in U.S. Pat. No. 6,602,682, which is expressly incorporated herein by reference in its entirety.

Yeast expression vectors that provide for secretion of heterologous proteins such as MtDef5 into the growth medium by transformed yeast are also contemplated. Secretion of the mature MtDef5 protein or peptide is typically achieved by operable linkage of a signal peptide sequence or a signal peptide and propeptide sequence to the mature MtDef5 protein- or peptide-encoding sequence. Examples of useful signal peptides for secretion of heterologous proteins in yeast include but are not limited to an α-factor signal peptide, an invertase signal peptide, and a PHO1 signal peptide, all of which are derived from yeast. The α-factor signal peptide is typically derived from *Saccharomyces, Kluveromyces*, or *Candida*, while the PHO1 signal peptide is derived from *Pichia*.

A particularly useful signal peptide sequence or signal peptide and propeptide sequence for secretion of proteins in yeast is derived from the *S. cerevisiae* α-factor, and is described in U.S. Pat. Nos. 4,546,082, 4,588,684, 4,870,008, and 5,602,034. The *S. cerevisiae* α-factor signal peptide and propeptide sequence consist of amino acids 1-83 of the primary, unprocessed translation product of the *S. cerevisiae* alpha mating factor gene (GenBank Accession Number: P01149). In certain embodiments, the signal peptide sequence of the alpha-mating factor comprising amino acids 1 to about 19 to 23 of the alpha-mating factor proprotein can be directly linked to the N-terminus of the mature MtDef5 protein to provide for secretion of mature MtDef5 protein. In this case, the signal peptide is cleaved from the mature MtDef5 protein in the course of the secretion process. Alternatively, the signal peptide and propeptide of the alpha mating factor can be operably linked to the mature MtDef5 encoding sequence via a spacer sequence. This spacer sequence can comprise a variety of sequences that provide for proteolytic processing of the leader sequence and gene of interest. In the native *S. cerevisiae* alpha mating factor gene the spacer sequence corresponds to amino acid residues 84-89 and is represented by the sequence Lys84-Arg85-Glu86-Ala87-Glu88-Ala 89 (SEQ ID NO:79). The sequence Lys-Arg corresponds to a KEX2 protease recognition site while the Glu-Ala-Glu-Ala (SEQ ID NO:80) sequence corresponds to a duplicated dipeptidylaminopeptidase or STE13 recognition site. In certain embodiments, a DNA fragment encoding the 89 amino acid *S. cerevisiae* alpha factor signal, propeptide coding region, and entire native spacer coding region (i.e., the N-terminal 89 amino acid residues of the alpha mating factor precursor protein containing both the Lys-Arg KEX2 protease cleavage site at residues 84 and 85 as well as the Glu-Ala-Glu-Ala (SEQ ID NO:80) dipeptidylaminopeptidase or STE13 recognition site at residues 86-89) is operably linked to the sequence encoding the mature MtDef5 protein. When the N-terminal 89 amino acids of the alpha mating factor precursor protein are fused to the N-terminus of a heterologous protein such as MtDef5, the propeptide sequence is typically dissociated from the heterologous protein via the cleavage by endogenous yeast proteases at either the KEX2 or STE13 recognition sites. In other embodiments, a DNA fragment encoding the smaller 85 amino acid *Saccharomyces cerevisiae* alpha factor signal peptide, propeptide, and KEX2 spacer element (i.e., the N-terminal 85 amino acid residues of the alpha mating factor precursor protein containing just the Lys-Arg KEX2 protease cleavage site at residues 84 and 85) is operably linked to the sequence encoding the mature MtDef5 protein. When the N-terminal 85 amino acids of the alpha mating factor precursor protein are fused to the N-terminus of a heterologous protein such as MtDef5, the propeptide sequence is typically dissociated from the heterologous protein via cleavage by endogenous yeast proteases at the KEX2 recognition site. The MtDef5 protein can thus be expressed without the glu-ala repeats.

To obtain transformed yeast that express MtDef5 proteins and peptides, the yeast MtDef5 expression cassettes (e.g., yeast promoter, yeast signal peptide encoding sequence, mature MtDef5 protein sequence, and polyadenylation sequence) are typically combined with other sequences that provide for selection of transformed yeast. Examples of useful selectable marker genes include, but are not limited to, genes encoding a ADE protein, a HIS5 protein, a HIS4 protein, a LEU2 protein, a URA3 protein, ARG4 protein, a TRP1 protein, a LYS2 protein, a protein conferring resistance to a bleomycin or phleomycin antibiotic, a protein conferring resistance to chloramphenicol, a protein conferring resistance to G418 or geneticin, a protein conferring resistance to hygromycin, a protein conferring resistance to methotrexate, an a ARO4-OFP protein, and a FZF1-4 protein.

DNA molecules comprising the yeast MtDef5 expression cassettes and selectable marker genes are introduced into yeast cells by techniques such as transfection into yeast spheroplasts or electroporation. In certain embodiments of the invention, the DNA molecules comprising the yeast MtDef5 expression cassettes and selectable marker genes are introduced as linear DNA fragments that are integrated into the genome of the transformed yeast host cell. Integration may occur either at random sites in the yeast host cell genome or at specific sites in the yeast host cell genome. Integration at specific sites in the yeast host cell genome is typically accomplished by homologous recombination between sequences contained in the expression vector and sequences in the yeast host cell genome. Homologous recombination is typically accomplished by linearizing the expression vector within the homologous sequence (for example, within the AOX1 promoter sequence of a *Pichia* expression vector when integrating the expression vector into the endogenous AOX1 gene in the *Pichia* host cell). In other embodiments of the invention, the yeast expression cassettes can also comprise additional sequences such as autonomous replication sequences (ARS) that provide for the replication of DNA containing the expression cassette as an extrachromosomal (non-integrated) element. Such extrachromosomal elements are typically maintained in yeast cells by continuous selection for the presence of the linked selectable marker gene. Yeast artificial chromosomes (YACs) containing sequences that provide for replication and mitotic transmission are another type of vector that can be used to maintain the DNA construct in a yeast host.

Methods of Producing MtDef5 Protein in Yeast

Yeast cells transformed with the yeast MtDef5 expression cassettes can be used to produce MtDef5 proteins and peptides. These MtDef5 molecules can be used directly as antifungal agents, to produce antifungal compositions that can be applied to plants, as immunogens to raise antibodies that recognize the MtDef5 proteins or peptides, or as reference standards in kits for measuring concentrations of MtDef5 proteins and peptides in various samples. The transformed yeast cells expressing MtDef5 antifungal molecules can also be applied to plants to combat/control pathogenic fungal infections. The methods of producing MtDef5 proteins and peptides typically first comprise the step of culturing yeast cells transformed with MtDef5 expression cassettes under conditions wherein the yeast cells express a mature MtDef5 molecule. In general, the conditions where the yeast cells express the mature MtDef5 molecules are conditions that allow for or specifically induce expression of the yeast promoter that is operably linked to the MtDef5 coding sequence in the yeast expression cassette. When the yeast is *Pichia* and the signal-peptide/MtDef5 gene is under the control of an AOX1 or AOX2 promoter, addition of methanol to the growth medium will provide for expression of mature MtDef5 protein. Similarly, when the yeast is *Hansuela* and the signal-peptide/MtDef5 gene is under the control of a MOX, DHAS, or FMDH promoter, addition of methanol to the growth medium will provide for expression of mature MtDef5 protein. Alternatively, when the yeast is *Kluveromyces* and the signal-peptide/MtDef5 gene is under the control of a Lactase promoter, addition of galactose to the growth medium will provide for expression of mature MtDef5 protein.

Once the transformed yeast culture has been incubated under culture conditions that provide for expression of mature MtDef5 protein or peptide for a sufficient period of time, the mature MtDef5 molecule can be isolated from the culture. A sufficient period of time can be determined by periodically harvesting portions or aliquots of the culture and assaying for the presence of MtDef5 protein or peptide. Analytical assays such as SDS-PAGE with protein staining, Western blot analysis, or any immunodetection method (e.g., such as an ELISA) can be used to monitor MtDef5 production. For example, incubation in the presence of methanol for between 1 to 8 days is sufficient to provide for expression of mature MtDef5 protein from the AOX1 promoter in *Pichia*.

Isolation of the MtDef5 protein or peptide from the culture can be partial or complete. For MtDef5 expression vectors where a yeast signal peptide is operably linked to the sequence encoding the mature MtDef5 protein, the mature MtDef5 protein can be recovered from the yeast cell culture medium. Yeast cell culture medium that contains the mature MtDef5 protein can be separated from the yeast cells by centrifugation or filtration, thus effecting isolation of mature MtDef5 protein. Yeast cell culture medium that contains the mature MtDef5 protein can be further processed by any combination of dialysis and/or concentration techniques (e.g., precipitation, lyophilization, filtration) to produce a composition containing the MtDef5 protein. Production of MtDef5 protein can also comprise additional purification steps that result in either a partially or completely pure preparation of the MtDef5 protein. To effect such purification, filtration size-exclusion membranes can be used. Alternatively, various types of chromatographic techniques such as size exclusion chromatography, ion-exchange chromatography, or affinity chromatography can be used to produce a partially or completely pure preparation of the MtDef5 protein.

Combinations of various isolation techniques can also be employed to produce the mature MtDef5 protein. For example, the cell culture medium can be separated from the cells by centrifugation and dialyzed or adjusted. A preferred buffer for dialysis or adjustment is a 25 mM sodium acetate buffer at about pH4.5-pH6.0. This dialysate is then subjected to ion-exchange chromatography. For example, a cation-exchange resin such as CM-Sephadex C-25 equilibrated with a 25 mM sodium acetate buffer at about pH6.0 can be used. MtDef5 protein bound to the cation exchange resin is washed and then eluted. For example, the aforementioned column is washed with 25 mM sodium acetate buffer at about pH6.0 and subsequently eluted in 1 M NaCl, 50 mM Tris, pH7.6. Fractions containing the defensin protein are identified by an assay or by UV absorbance and then concentrated by a size-cut-off filtration membrane. The concentrated MtDef5 protein is then dialyzed to obtain an essentially pure MtDef5 protein in a desirable buffer. Desirable buffers include, but are not limited to, buffers such as 10 mM Tris, pH 7.6.

Peptides, Polypeptides, and Proteins Containing Conservative Amino Acid Changes in MtDef5 Sequences Peptides, polypeptides, and proteins biologically functionally equivalent to MtDef5 proproteins, mature proteins, and peptides include, but are not limited to, amino acid sequences containing conservative amino acid substitutions in MtDef5 sequences SEQ ID NOs:1, 3-9, 16-22, and 49-64 disclosed herein. In such amino acid sequences, one or more amino acids in the sequence is (are) substituted with another amino acid(s), the charge and polarity of which is similar to that of the native amino acid, i.e., a conservative amino acid substitution, resulting in a silent change.

Substitutes for an amino acid within the MtDef5 sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within MtDef5 sequences can be made by substituting one amino acid within one of these groups with another amino acid within the same group. Biologically functional equivalents of MtDef5 can have 10 or fewer conservative amino acid changes, more preferably seven or fewer conservative amino acid changes, and most preferably five, four, three, two, or one conservative amino acid changes. The encoding nucleotide sequence (e.g., gene, plasmid DNA, cDNA, or synthetic DNA) will thus have corresponding base substitutions, permitting it to encode biologically functional equivalent forms of MtDef5 molecules.

The biologically functional equivalent peptides, polypeptides, and proteins contemplated herein should possess about 70% or greater sequence identity, preferably about 85% or greater sequence identity, more preferably about 90% to about 95% sequence identity, e.g., about 90%, about 91%, about 92%, about 93%, about 94%, or about 95% sequence identity, and even more preferably greater than about 96%, 97%, or 98% sequence identity, or about 99% sequence identity to the sequence of, or corresponding moiety within, the particular MtDef5 protein or peptide sequence of interest. Such biologically functional equivalent peptides, polypeptides, and proteins preferably exhibit about ±30% of the antifungal activity of the corresponding MtDef5 molecule disclosed herein, or even greater than about +30% antifungal activity, determined by any of the antifungal activity assay methods disclosed herein.

Coding sequences for such biologically functional equivalent peptides, polypeptides, and protein should comprise a nucleotide sequence having a sequence identity to a nucleotide sequence selected from the group consisting of nucleotide sequences shown in SEQ ID NOs:10-15, 23-29, and 65-78 sufficient to enable the coding sequence to encode the biologically functional equivalent antifungal peptide, polypeptide, or protein, or a codon-optimized version of such coding sequence to optimize expression thereof in a plant.

Methods for Determining Sequence Identity

Methods of alignment of sequences for comparison are well-known in the art. Optimal alignment of sequences for comparison can be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Nat. Acad. Sci.* 85: 2444 (1988); by computerized implementations of these algorithms, including, but not limited to: CLUSTAL in the PC/Gene program by Intelligenetics, Mountain View, Calif; and GAP, BESTFIT, BLAST, FASTA, and TFASTA in the GCG® Wisconsin Package™ from Accelrys, Inc., San Diego, Calif.

Gene identities can be determined by conducting BLAST (Basic Local Alignment Search Tool; Altschul, S. F., et al., (1993) *J. Mol. Biol.* 215:403-410; see also information available from NCBI (National Center for Biotechnology Information, U.S. National Library of Medicine, 8600 Rockville Pike, Bethesda, Md. 20894)) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN program. The DNA sequences are translated in all reading frames and compared for similarity to all publicly available protein sequences contained in the "nr" database using the BLASTX program (Gish, W. and States, D. J. *Nature Genetics* 3:266-272 (1993)) provided by the NCBI. In some cases, the sequencing data from two or more clones containing overlapping segments of DNA are used to construct contiguous DNA sequences.

Sequence alignments and percent identity calculations can be performed using software such as GAP, BestFit, PileUp or Pretty, available as part of the GCG® Wisconsin Package™ from Accelrys, Inc., San Diego, Calif Default parameters for pairwise alignments of polynucleotide sequences using GAP and BestFit are Gap Creation Penalty=50, Gap Extension Penalty=3; nwsgapdna.cmp is the scoring matrix. Default parameters for pairwise alignments for polypeptide sequences using GAP and BestFit are Gap Creation Penalty=8, Gap Extension Penalty=2; BLOSUM62 is the scoring matrix. There is no penalty for gaps at ends of polynucleotide or polypeptide alignments.

Default parameters for polynucleotide sequence comparison using PileUp and Pretty are: Gap Creation Penalty=5, Gap Extension Penalty=1. Default parameters for polypeptide sequence comparison using PileUp or Pretty are Gap Creation Penalty=8, Gap Extension Penalty=2; BLOSUM62 is the scoring matrix.

Sequence alignments can also be accomplished with the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

Other pairwise comparison tools are also available and known to those of skill in the art.

As indicated, modifications and changes can be made in the structure of the MtDef5 proteins and peptides of the present invention, and DNA segments that encode them, and still obtain a functional molecule that encodes a peptide, polypeptide, or protein with desirable antifungal characteristics. The following is a discussion based upon changing the amino acids of a protein to create an equivalent, or even an improved, second-generation molecule. In particular embodiments of the invention, mutated MtDef5 proteins or peptides are contemplated to be useful for increasing the antifungal activity of the these molecules, and consequently increasing the antifungal activity and/or expression of the recombinant transgene in a plant cell. The amino acid changes can be achieved by changing the codons of the DNA sequence, according to the codons given in Table 2.

TABLE 2

| Amino Acids | Amino Acid Codes | Codons |
|---|---|---|
| Alanine | Ala (A) | GCA GCC GCG GCU |
| Cysteine | Cys (C) | UGC UGU |
| Aspartic acid | Asp (D) | GAC GAU |
| Glutamic acid | Glu (E) | GAA GAG |
| Phenylalanine | Phe (F) | UUC UUU |
| Glycine | Gly (G) | GGA GGC GGG GGU |
| Histidine | His (H) | CAC CAU |
| Isoleucine | Ile (I) | AUA AUC AUU |
| Lysine | Lys (K) | AAA AAG |
| Leucine | Leu (L) | UUA UUG CUA CUC CUG CUU |
| Methionine | Met (M) | AUG |
| Asparagine | Asn (N) | AAC AAU |
| Proline | Pro (P) | CCA CCC CCG CCU |
| Glutamine | Gln (Q) | CAA CAG |
| Arginine | Arg (R) | AGA AGG CGA CGC CGG CGU |
| Serine | Ser (S) | AGC AGU UCA UCC UCG UCU |
| Threonine | Thr (T) | ACA ACC ACG ACU |
| Valine | Val (V) | GUA GUC GUG GUU |
| Tryptophan | Trp (W) | UGG |
| Tyrosine | Tyr (Y) | UAC UAU |

For example, certain amino acids can be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes can be made in the MtDef5 protein sequences of the invention, or corresponding DNA sequences that encode them, without appreciable loss of their biological utility or activity.

Betts and Russell ((2003), "Amino Acid Properties and Consequences of Substitutions", *Bioinformatics for Geneticists*, Michael R. Barnes and Ian C. Gray, Eds., John Wiley & Sons, Ltd, Chapter 14, pp. 289-316) review the nature of mutations and the properties of amino acids in a variety of different protein contexts with the purpose of aiding in anticipating and interpreting the effect that a particular amino acid change will have on protein structure and function. The authors point out that features of proteins relevant to considering amino acid mutations include cellular environments, three-dimensional structure, and evolution, as well as the classifications of amino acids based on evolutionary, chemical, and structural principles, and the role for amino acids of different classes in protein structure and function in different contexts. The authors note that classification of amino acids into categories such as those shown in FIG. 14.3 of their review, which involves common physico-chemical properties, size, affinity for water (polar and non-polar; negative or positive charge), aromaticity and aliphaticity, hydrogen-bonding ability, propensity for sharply turning regions, etc., makes it clear that reliance on simple classifications can be misleading, and suggests that alternative amino acids could be engineered into a protein at each position. Criteria for interpreting how a particular mutation might affect protein structure and function are summarized in section 14.7 of this review, and include first inquiring about the protein, and then about the particular amino acid substitution contemplated.

As a starting point in making amino acid changes, the hydropathic index of amino acids can be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids can be substituted by other amino acids having a similar hydropathic index or score and still result in a protein with similar biological activity, i.e., still obtain a biological functionally equivalent protein. In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Non-Conservative Substitutions in MtDef5 Sequences

It is further recognized that non-conservative substitutions in MtDef5 sequences can be made to obtain MtDef5 proteins and peptides that are the functional biological equivalents of the MtDef5 molecules disclosed herein. In these instances, the non-conservative substitutions can simply be tested for its effect on inhibition of fungal growth to identify non-conservative substitutions that provide for functional biological equivalents of a given MtDef5 protein or peptide.

Fragments and Variants of MtDef5 Proteins and Peptides

The antifungal defensins of the present invention include MtDef5 proproteins, mature MtDef5 proteins, and MtDef5 peptides. Fragments and variants of these sequences possessing the same, similar, or even greater antifungal activity compared to that of these MtDef5 molecules are also encompassed by the present invention. Thus, contiguous sequences of at least 8 or more amino acids in a mature MtDef5 protein exhibiting antifungal activity are encompassed by this invention. Fragments or variants of MtDef5 molecules with antifungal activity that are encompassed by this invention can also comprise amino acid substitutions, deletions, insertions or additions in an MtDef5 sequence.

Fragments of mature MtDef5 proteins, which can be truncated forms, wherein one or more amino acids are deleted from the N-terminal end, C-terminal end, the middle of the protein, or combinations thereof, and which possess antifungal activity, are also encompassed by this invention. These fragments can be naturally occurring or synthetic mutants of MtDef5 molecules, and retain the antifungal activity of MtDef5, preferably about +30% of the antifungal activity of the corresponding MtDef5 protein or peptide disclosed herein, or even greater than about +30% antifungal activity, determined by any of the presently disclosed antifungal activity assay methods.

Variants of MtDef5 proteins include forms wherein one or more amino acids has/have been inserted into the natural sequence. These variants can also be naturally occurring or synthetic mutants of MtDef5, and should retain about +30% of the antifungal activity of the corresponding MtDef5 protein disclosed herein, or even greater than about +30% antifungal activity, determined by any of the presently disclosed antifungal activity assay methods.

Combinations of the foregoing, i.e., forms of the antifungal MtDef5 defensin containing both amino acid deletions and additions, are also encompassed by the present invention. Amino acid substitutions can also be present therein as well.

The fragments and variants of MtDef5 proteins encompassed by the present invention should preferably possess about 70-75% or greater sequence identity, preferably about 85% or greater sequence identity, more preferably about 90% to 95% sequence identity, and even more preferably greater than about 96%, 97%, 98%, or 99% sequence identity to the sequence of, or corresponding moiety within, the MtDef5 sequence. Such biologically functional equivalent peptides, polypeptides, and proteins preferably exhibit about ±30% of the antifungal activity of the corresponding MtDef5 molecule disclosed herein, or even greater than about +30% antifungal activity, determined by any of the presently disclosed antifungal activity assay methods.

Use of MtDef5 Defensin Structure Function Relationships to Design MtDef5 Variants The MtDef5 proteins are members of the Defensin gene family and are thus anticipated to possess certain structural and biochemical properties shared by Defensins. In particular, the MtDef5 proteins are anticipated to possess a cysteine-stabilized α/β motif, composed of three antiparallel β-strands and one α-helix, that are typically observed in Defensin proteins (Almeida et al, J. Mol. Biol. (2002) 315, 749-757; Thomma et al, Planta (2002) 216: 193-202). Without being limited by theory, the structural homology between MtDef5 and other defensins can be used to identify variants that possess similar or even increased antifungal activity.

Alternatively, the conserved structural features of the MtDef5 defensins can also be used to engineer variant MtDef5 derivatives with other desirable properties. For example, the 8 canonical cysteine residues of MtDef5 that typically form disulfide linkages in Defensin proteins would typically be conserved or maintained in any MtDef5 variants. The predicted pairing of disulfide bonds in MtDef5 is between cysteine residues 3 and 50, 14 and 35, 20 and 44, and 24 and 46. Thus, Cys-pair 1 is predicted to be formed by a Cys3-Cys50 disulfide bond, Cys-pair 2 is predicted to be formed by a Cys14-Cys35 disulfide bond, Cys-pair 3 is predicted to be formed by a Cys20-Cys44 disulfide bond, and Cys-pair 4 is predicted to be formed by a Cys24-Cys46 disulfide bond. While not being limited by theory, it is believed that MtDef5 cysteine variants that lack one or more disulfide linkages may be desirable for use in transgenic plants that are ultimately used as animal feed or as food for human consumption as such variants are predicted to be more readily digested by animal or humans that consume the transgenic plant products. MtDef5 variant proteins that have shorter half-lives in the digestive tracts of animals or humans are in theory anticipated to have less potential to become food allergens while retaining their antifungal activity. It would thus be desirable to design MtDef5 defensin derivatives that have fewer disulfide bonds, yet retain antifungal activity.

Other Biologically Functional Equivalent Forms of MtDef5 Proteins and Peptides

Other biologically functional equivalent forms of MtDef5 proteins and peptides useful in the present invention include conjugates of these molecules, or biologically functional equivalents thereof as described above, with other peptides, polypeptides, or proteins, forming fusion products therewith exhibiting the same, similar, or greater antifungal activity as compared with that of the corresponding MtDef5 molecule.

As noted above in the discussion of stacked genes, simultaneous co-expression of multiple antifungal and/or other anti-pathogen proteins in plants is advantageous in that it exploits more than one mode of control of plant pathogens. This may, where two or more antifungal proteins are expressed, minimize the possibility of developing resistant fungal species, broaden the scope of resistance, and potentially result in a synergistic antifungal effect, thereby enhancing the level of resistance.

Site-Specific Mutagenesis

Site-specific mutagenesis is a technique useful in the preparation of individual peptides, or biologically functional equivalent peptides, polypeptides, or proteins, through specific mutagenesis of the DNA encoding the molecule. The technique further provides a ready ability to prepare and test sequence variants, incorporating, for example, one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector that exists in both a single-stranded and double-stranded form. Typical vectors useful in site-directed mutagenesis include vectors such as the M13 phage. These phage vectors are readily commercially available, and their use is generally well known to those skilled in the art. Double-stranded plasmids are also routinely employed in site directed mutagenesis which eliminates the step of transferring the gene of interest from a plasmid to a phage. Commercially available kits for performing mutagenesis are also available and can be used. Exemplary kits include the QuikChange® sited directed mutagenesis kits (Stratagene, La Jolla, CA, USA).

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them can be obtained. For example, recombinant vectors encoding the desired peptide sequence can be treated with mutagenic agents, such as hydroxylamine, to obtain sequence variants.

MtDef5 Antibody Compositions and Methods of Making Antibodies

In particular embodiments, the inventors contemplate the use of antibodies, either monoclonal or polyclonal, that bind to the MtDef5 proteins and peptides disclosed herein. Means for preparing and characterizing antibodies are well known in the art (see, for example, *Using Antibodies: A Laboratory Manual*, Cold Spring Harbor Laboratory, 1999, and U.S. Pat. No. 4,196,265, both incorporated herein by reference).

MtDef5 Protein Screening and Detection Kits

The present invention contemplates immunodetection methods and kits for screening samples suspected of containing MtDef5 proteins or peptides, or MtDef5-related peptides, polypeptides, or proteins, or cells producing such molecules. A kit can contain one or more antibodies of the present invention, and can also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention. Detection of immunocomplex formation can be achieved, for example, via the application of ELISA, RIA, immunoblot (e.g., dot blot), indirect immunofluorescence techniques, and the like.

MtDef5 Agricultural and Pharmaceutical Antifungal Compositions

The present invention encompasses agricultural and pharmaceutical antifungal compositions comprising either an antifungal plant, or antifungal human or veterinary, pathogenic fungus inhibitory amount ("antifungal effective amount") of one or more the present isolated, purified antifungal MtDef5 proteins or peptides, or biologically functional equivalents thereof, of the present invention. Such compositions can comprise one, or any combination of, MtDef5 proteins or peptides disclosed herein, and an agriculturally or pharmaceutically/veterinarily acceptable carrier, diluent, or excipient. As indicated below, other components relevant in agricultural and therapeutic contexts can be included in such compositions as well. The antifungal compositions can be used for inhibiting the growth of, or killing, MtDef5 protein- or peptide-susceptible pathogenic fungi associated with plant, or human or animal, fungal infections. Such antifungal compositions can be formulated for topical administration, and applied topically to either plants, the plant environment (including soil), or humans or animals.

Agricultural Compositions Comprising MtDef5 Proteins and Peptides, and Protein- and Peptide-Producing Microorganisms Agricultural compositions comprising any of the present MtDef5 molecules alone, or in any combination, can be formulated as described in, for example, Winnacker-Kuchler (1986) *Chemical Technology*, Fourth Edition, Volume 7, Hanser Verlag, Munich; van Falkenberg (1972-1973) *Pesticide Formulations*, Second Edition, Marcel Dekker, N.Y.; and K. Martens (1979) *Spray Drying Handbook*, Third Edition, G. Goodwin, Ltd., London. Necessary formulation aids, such as carriers, inert materials, surfactants, solvents, and other additives are also well known in the art, and are described, for example, in Watkins, *Handbook of Insecticide Dust Diluents and Carriers*, Second Edition, Darland Books, Caldwell, N.J., and Winnacker-Kuchler (1986) *Chemical Technology*, Fourth Edition, Volume 7, Hanser Verlag, Munich. Using these formulations, it is also possible to prepare mixtures of the present MtDef5 proteins and peptides with other pesticidally active substances, fertilizers, and/or growth regulators, etc., in the form of finished formulations or tank mixes.

Whether alone or in combination with other active agents, the present antifungal MtDef5 proteins and peptides can be applied at a concentration in the range of from about 0.1 µg ml to about 100 mg ml, preferably between about 5 µg ml and about 5 mg ml, at a pH in the range of from about 3.0 to about 9.0. Such compositions can be buffered using, for example, phosphate buffers between about 1 mM and 1 M, preferably between about 10 mM and 100 mM, more preferably between about 15 mM and 50 mM. In the case of low buffer concentrations, it is desirable to add a salt to increase the ionic strength, preferably NaCl in the range of from about 1 mM to about 1 M, more preferably about 10 mM to about 100 mM.

Numerous conventional fungal antibiotics and chemical fungicides with which the present MtDef5 proteins and peptides can be combined are known in the art, and are described in Worthington and Walker (1983) *The Pesticide Manual*, Seventh Edition, British Crop Protection Council. These include, for example, polyoxines, nikkomycines, carboxy amides, aromatic carbohydrates, carboxines, morpholines, inhibitors of sterol biosynthesis, and organophosphorus compounds. Other active ingredients which can be formulated in combination with the present antifungal proteins and peptides include, for example, insecticides, attractants, sterilizing agents, acancides, nematocides, and herbicides. U.S. Pat. No. 5,421,839 contains a comprehensive summary of the many active agents with which substances such as the present antifungal MtDef5 proteins and peptides can be formulated.

MtDef5 proteins and peptides and biologically functional equivalents thereof are expected to be useful in controlling a wide variety of susceptible fungi in plants, exemplified by those in the following genera and species: *Alternaria* (*Alternaria brassicola; Alternaria solani*); *Ascochyta* (*Ascochyta pisi*); *Aspergillus* (*Aspergillus flavus; Aspergillus fumigatus*); *Botrytis* (*Botrytis cinerea*); *Cercospora* (*Cercospora kikuchii; Cercospora zeae-maydis*); *Colletotrichum* (*Colletotrichum lindemuthianum*); *Diplodia* (*Diplodia maydis*); *Erysiphe* (*Erysiphe graminis* fsp. *graminis; Erysiphe graminis* fsp. *hordei*); *Fusarium* (*Fusarium nivale; Fusarium oxysporum; Fusarium graminearum; Fusarium culmorum; Fusarium solani; Fusarium moniliforme; Fusarium roseum*); *Gaeumannomyces* (*Gaeumannomyces graminis* f. sp. *tritici*); *Helminthosporium* (*Helminthosporium turcicum; Helminthosporium carbonum; Helminthosporium maydis*); *Macrophomina* (*Macrophomina phaseolina; Maganaporthe grisea*); *Nectria* (*Nectria heamatococca*); *Peronospora* (*Peronospora manshurica; Peronospora tabacina*); *Phakopsora* (*Phakopsora pachyrhizi*); *Phoma* (*Phoma betae*); *Phymatotrichum* (*Phymatotrichum omnivorum*); *Phytophthora* (*Phytophthora cinnamomi; Phytophthora cactorum; Phytophthora phaseoli; Phytophthora parasitica; Phytophthora citrophthora; Phytophthora megasperma* fsp. *sojae; Phytophthora infestans*); *Plasmopara* (*Plasmopara viticola*); *Podosphaera* (*Podosphaera leucotricha*); *Puccinia* (*Puccinia sorghi; Puccinia striiformis; Puccinia graminis* fsp. *tritici; Puccinia asparagi; Puccinia recondita; Puccinia arachidis*); *Pythium* (*Pythium aphanidermatum*); *Pyrenophora* (*Pyrenophora tritici-repentens*); *Pyricularia* (*Pyricularia oryzae*); *Pythium* (*Pythium ultimum*); *Rhizoctonia* (*Rhizoctonia solani; Rhizoctonia cerealis*); *Scerotium* (*Scerotium rolfsii*); *Sclerotinia* (*Sclerotinia sclerotiorum*); *Septoria* (*Septoria lycopersici; Septoria glycines; Septoria nodorum; Septoria tritici*); *Thielaviopsis* (*Thielaviopsis basicola*); *Uncinula* (*Uncinula necator*); *Venturia* (*Venturia inaequalis*); *Verticillium* (*Verticillium dahliae; Verticillium alboatrum*).

Agriculturally useful antifungal compositions encompassed herein also include those in the form of host cells, such as bacterial and fungal cells, capable of the producing the MtDef5 proteins and peptides, and which can colonize plants, including roots, shoots, leaves, or other parts of plants.

The term "plant-colonizing microorganism" is used herein to refer to a microorganism that is capable of colonizing the "plant environment", and which can express the present MtDef5 antifungal proteins and peptides in the "plant environment". A plant colonizing micro-organism is one that can exist in symbiotic or non-detrimental relationship with a plant in the plant environment.

U.S. Pat. No. 5,229,112 discloses a variety of plant-colonizing microorganisms that can be engineered to express antifungal proteins, and methods of use thereof, applicable to the MtDef5 antifungal proteins and peptides disclosed herein. Plant-colonizing microorganisms expressing the presently disclosed MtDef5 antifungal proteins and peptides useful in inhibiting fungal infection and damage in plants according to the present invention include, for example, bacteria selected from the group consisting of genera selected from spore forming organisms of the family Bacillaceae, for example *Bacillus* species such as *Bacillus thuringiensis, Bacillus israelensis*, and *Bacillus subtilis; Pseudomonas; Arthrobacter; Azospyrillum; Clavibacter; Escherichia; Agrobacterium*, for example *A. radiobacter; Rhizobium; Erwinia; Azotobacter; Azospirillum; Klebsiella; Alcaligenes; Rhizobacterium*; and *Flavobacterium*; and yeasts selected from the group consisting of *Saccharomyces cerevisiae; Pichia pastoris*; and *Pichia* methanolica.

The term "plant environment" includes the surface of a plant, e.g., leaf, stem, buds, stalk, floral parts, or root surface, the interior of the plant and its cells, and to the "rhizosphere", i.e., the soil which surrounds and which is influenced by the roots of the plant.

When it is desired to apply the present MtDef5 molecules to the rhizosphere, rhizosphere-colonizing bacteria from the genus *Pseudomonas* are particularly useful, especially the fluorescent pseudomonads, e.g., *Pseudomonas fluorescens*, which is especially competitive in the plant rhizosphere and in colonizing the surface of the plant roots in large numbers. Examples of suitable phylloplane (leaf) colonizing bacteria are *P. putida, P. syringae*, and *Erwinna* species.

The antifungal plant-colonizing microorganisms of the invention can be applied directly to the plant environment, e.g., to the surface of leaves, buds, roots, shoots, floral parts, seeds, etc., or to the soil. When used as a seed coating, the plant-colonizing microorganisms of the invention are applied to the plant seed prior to planting. Generally, small amounts of the antifungally active microorganism will be required to treat such seeds.

The determination of an antifungal effective amount of plant-colonizing microorganisms useful in the methods of the present invention required for a particular plant is within the skill of the art, and will depend on such factors as the plant species, the fungal pathogen, method of planting, and the soil type, (e.g., pH, organic matter content, moisture content).

Theoretically, a single plant-colonizing microorganism of the invention containing DNA encoding the MtDef5 antifungal proteins and peptides disclosed herein is sufficient to control fungal pathogens because it can grow into a colony of clones of sufficient number to express antifungal amounts of the Defensin. However, in practice, due to varying environmental factors which may affect the survival and propagation of the microorganism, a sufficient number of plant colonizing microorganisms should be provided in the plant environment (e.g., roots or foliage) to assure survival and/or proliferation. For example, application of $10^3$ to $10^{10}$ bacteria or yeasts per seed may be sufficient to insure colonization on the surface of the roots by the microorganism. It is preferred to dose the plant environment with enough bacteria or other plant-colonizing microorganism to maintain a population that expresses 50 to 250 nanograms of Defensin. For example, $10^5$ to $10^8$ bacteria per square centimeter of plant surface may be adequate to control fungal infection. At least 0.5 nanograms, preferably 1 to 100 nanograms, of anti-fungal active protein or peptides may be sufficient to control fungal damage to plants.

Compositions containing the antifungally active plant-associated microorganisms of the invention can be prepared by formulating the biologically active microorganism with adjuvants, diluents, carriers, etc., to provide compositions in the form of finely-divided particulate solids, granules, pellets, wettable powders, dusts, aqueous suspensions, dispersions, or emulsions. Illustrative of suitable carrier vehicles are: solvents, e.g., water or organic solvents, and finely divided solids, e.g., kaolin, chalk, calcium carbonate, talc, silicates, and gypsum.

The present invention also encompasses the use of the antifungal plant-colonizing microorganisms in the methods and compositions of the invention in encapsulated form, e.g., the plant-colonizing microorganisms can be encapsulated within shell walls of polymer, gelatin, lipid, and the like. Other formulation aids such as, for example, emulsifiers, dispersants, surfactants, wetting agents, anti-foam agents, and anti-freeze agents, can be incorporated into the antifungal compositions, especially if such compositions will be stored for any period of time prior to use.

In addition to the antifungally active plant-colonizing microorganisms, the compositions of the invention can additionally contain other known biologically active agents, such as, for example, a fungicide, herbicide, or insecticide. Also, two or more antifungally active plant-colonizing microorganisms can be combined.

The application of antifungal compositions containing the genetically engineered plant-colonizing microorganisms of the invention as the active agent can be carried out by conventional techniques utilizing, for example, spreaders, power dusters, boom and hand sprayers, spry dusters, and granular applicators.

The compositions of the invention are applied in an antifungal effective amount, which will vary depending on such factors as, for example, the specific fungal pathogen to be controlled, the specific plant (and plant part or soil) to be treated, and the method of applying the antifungally active compositions.

MtDef5 Antifungal Protein- and Peptide-Containing Pharmaceutical Compositions

The present invention not only encompasses transgenic plants expressing MtDef5 proteins and peptides and transformed microorganisms that can be applied to the loci of plants, but also pharmaceutical compositions that can be used for inhibiting the growth of, or killing, susceptible pathogenic fungi that infect humans or animals, i.e., treating such fungal infections by administering to a patient or other subject in need thereof an antifungal effective amount of MtDef5 proteins, peptides, or biologically functional equivalents thereof.

Such pharmaceutical compositions comprising MtDef5 proteins and peptides, and biologically functional equivalents thereof, can be formulated by conventional methods such as those described in *Remington: The Science and Practice of Pharmacy* (2005), 21$^{st}$ Edition, University of the Sciences in Philadelphia, Lippincott Williams & Wilkins. Such compositions can contain MtDef5 proteins and peptides, and various combinations thereof, at concentrations in the range of from about 0.1 µg ml to about 100 mg ml, preferably between about 5 µg ml and about 5 mg ml, at a pH in the range of from about 3.0 to about 9.0. Such compositions can be buffered using, for example, phosphate buffers between about 1 mM and 1 M, preferably between about 10 mM and 100 mM, more preferably between about 15 mM and 50 mM. In the case of low buffer concentrations, it is desirable to add a salt to increase the ionic strength, preferably NaCl in the range of from about 1 mM to about 1 M, more preferably about 10 mM to about 100 mM.

The MtDef5 proteins and peptides can be formulated alone, in any combination with one another, and either of these can additionally be formulated in combination with other conventional antifungal therapeutic compounds such as, by way of non-limiting example, polyene antifungals; imidazole, triazole, and thiazole antifungals; allylamines; and echinocandins that are routinely used in human and veterinary medicine.

Administration of the present MtDef5 molecules can be accomplished via a variety of conventional routes, with topical application being preferred.

The following examples describe various aspects of the present invention, and are merely intended to be illustrative rather than limiting of the compounds, compositions, and methods useful therein.

Example 1

Construction of Soybean Transformation Vector AKK/FMV/MtDef5

As shown in FIG. 1, a MtDef5 gene or cDNA with its own signal peptide is cloned as a NcoI-XbaI fragment between the Figwort mosaic virus 35S promoter (Sanger et al. (1990) *Plant Molecular Biology* 14:433-443) and nopaline synthase polyadenylation signal (Gleave (1992) *Plant Molecular Biology* 20:1203-1207) in the soybean expression vector AKK1472 (Hammes et al. (2005) *Molecular Plant Microbe Interactions* 18:1247-1257). The AKK1472 vector containing aMtDef5 chimeric gene or cDNA and bar gene conferring Basta® resistance as a selectable marker gene (Thompson et al. (1985) *EMBO Journal* 6:2519-2523) is transferred to *Agrobacterium tumefaciens* strain EHA105 for soybean transformation (Clemente et al. (2000) *Crop Sci.* 40:797-803; Zhang et al. (1999) *Plant Cell, Tiss. Organ Cult.* 56:37-46).

Example 2

Soybean Transformation and Regeneration of Transgenic Plants

The transformation protocol used in this example to create transgenic soybean lines using *Agrobacterium* has been previously described (Clemente et al. (2000) *Crop Sci.* 40:797-803; Zhang et al. (1999) *Plant Cell, Tiss. Organ Cult.* 56:37-46).

The exterior of the seeds (in this case the soybean variety called "Jack") are first sterilized using commercial grade Clorox© (5% aqueous sodium hypochlorite, NaClO) overnight. The sterilized seeds are then allowed to germinate in germination medium (GM; Gamborg's B5 medium (Gamborg et al. (1968) *Experimental Cell Research* 50:151) supplemented with 2% sucrose, pH 5.8, solidified with 0.8% agar) for 5 days at 24° C. (18/6) light regime). The *A. tumefaciens* transformed with the vector of Example 1 are collected via low speed centrifugation and suspended in co-cultivation medium to a final OD$_{650}$ of 0.6 to 1.0. Co-cultivation medium is ¹⁄₁₀th Gamborg's B5 medium supplemented with 1.67 mg/l 6-benzylaminopurine (BAP), 0.25 mg/l gibberellic acid (GA3), 3% sucrose, 200 µM acetosyringone, 20 mM 2-(N-morpholino)-ethanesulfonic acid (MES), pH 5.4.

The following protocol has been previously described (Clemente et al. (2000) supra; Zhang et al. (1999) supra).

*Agrobacterium* inoculum is placed in a petri plate with the prepared explants (from wounded, germinating seed) for 30 min., with occasional agitation. The explants are then placed on co-cultivation plates (Petri dishes containing 0.76 g Gamborg Basal Salt Mixture, 7.4 g MES, 60 g sucrose, pH adjusted to 5.4 using 1 M KOH, and 5 g/L agarose dissolved in warm media), adaxial side down. The plates are wrapped with parafilm and placed at 24° C., 18/6 light regime for 3 days. Following the co-cultivation period, the explants are briefly washed in liquid shoot initiation medium (3.08 g of Gamborgs B5 salts, 30 g Sucrose, 0.56 g MES, adjusted to pH to 5.6 using 1 M KOH) supplemented with 0.25 mg/l GA3. After the first two weeks, the hypocotyl region is cut flush to the developing node, and incubated for two weeks in the absence of glufosinate. The tissue is then transferred to fresh shoot initiation medium every two weeks, for a total of approximately 10 weeks with 3 mg/l glufosinate. The tissue is oriented so that the freshly cut surface is imbedded in the medium, with the differentiating region flush to the surface. At the end of the shoot initiation period, only the differentiating explants are used. The cotyledons are removed from the explants, and a fresh cut is made at the base of the developing node (horizontally), the tissue is transferred to shoot elongation medium, and is cultured at 24° C. with a 18/6 light regime. Shoot elongation medium is composed of MS salts/Gamborg's vitamins supplemented with 1 mg/l zeatin riboside, 0.1 mg/l indole acetic acid (IAA), 0.5 mg/l GA3, 3% sucrose, 100 mg/l pyroglutamic acid, 50 mg/l asparagine, 3 mM MES (pH 5.6), solidified with 0.8% purified agar. Since the bar gene is used as a marker, 3 mg/l glufosinate is added. The tissue is transferred to fresh shoot elongation medium every two weeks. At each transfer, a fresh horizontal slice is made at the base of the tissue. Elongated shoots (greater than 3 cm) are rooted on rooting medium without further selection. Rooting medium is composed of 4.33 g of Murashige & Skoog Basal Salt Mixture, 20 g sucrose, 0.56 g MES. The pH is adjusted to 5.6 using 1 M KOH and 3 g Phytagel per liter are added. The solution is autoclaved (20 min.) and when cooled, 1 ml Gamborg B5 vitamins (1000×), 1 ml L-asparagine monohydrate (50 mg/ml stock), and 1 ml L-Pyroglutamic acid (100 mg/ml stock) are added.

The plants are then grown and selected for using PCR to detect the presence of the MtDef5 gene or cDNA. The expression of the MtDef5 gene or cDNA at the RNA level is determined using the qRT-PCR assay, and expression of the MtDef5 protein is determined by sandwich ELISA using a MtDef5 polyclonal antibody. Homozygotes are eventually selected using quantitative PCR using the Promega GoTaq® qPCR master mix (Promega Corporation, Madison, WI) on an AB StepOne Plus-Real time PCR system (Applied Biosystems, Carlsbad, CA) per the manufacturer's instructions.

Transgenic plants that are homozygous for the MtDef5 DNA construct insertion will be obtained, identified, and subsequently tested for resistance to *Fusarium* head blight as described in Chen et al. (1999) *Theor. Appl. Genet.* 99:755-760; leaf rust and stripe rust as described in Cheng et al. (2010) *Theor. Appl. Genet.* 121:195-204); and stem rust as described in Nirmala et al. (2011) *PNAS* 108:14676-14681.

Example 3

Construction of Wheat Transformation Vector pZP212/Maize Ubi1A Promoter/MtDef5/35S 3'

For expression of MtDef5 in wheat, a MtDef5 gene or cDNA will be synthesized based on monocot preferred codons such that the amino acid sequence of the MtDef5 signal peptide and mature protein remain unchanged. The synthetic MtDef5 gene or cDNA will be obtained from the GenScript Corporation (Piscataway, NJ, USA). The synthetic MtDef5 gene will be placed between the maize ubiquitin (Ubi1) promoter/intron and CaMV 35S polyadenylation signal sequence and cloned between the T-DNA borders of the binary plant expression vector pZP212 (Hajdukiewicz et al., 1994) as shown in FIG. 2.

The pZP212 vector containing the synthetic MtDef5 gene or cDNA and a neomycin phosphotransferase selectable marker gene (nptII) will be introduced into Bobwhite and/or XC9 wheat. The transgenic wheat will be obtained as described below in Example 4.

Example 4

Wheat Transformation and Regeneration of Transgenic Plants

The protocol used for wheat transformation was previously described by Cheng et al. (1997) *Plant Physiology* 115:971-980.

For these transformations, *Triticum aestivum* cv Bobwhite, is used. Immature caryopses are collected from plants 14 days after anthesis. Immature embryos are dissected aseptically and cultured on a semisolid or liquid CM4 medium (Zhou et al. (1995) *Plant Cell Replication* 15:159-163) with 100 mg L-ascorbic acid (CM4C). The MS salts (Murashige and Skoog (1962) *Physiology Plant.* 15:473-497) in the CM4 medium are adjusted to full strength (the original amounts) or one-tenth-strength (Fry et al. (1987) *Plant Cell Reports* 6: 321-325). The immature embryos are cultured for 3 to 4 hours. Embryogenic calli are prepared by culturing the immature embryos on CM4C medium for 10 to 25 days. The callus pieces derived from immature embryos are inoculated with *A. tumefaciens* using the embryogenic callus sectors. *A. tumefaciens* C58 (ABI) harboring the vector described in Example 3 (FIG. 2) is prepared as described above in Example 3 for soybean transformation. The *A. tumefaciens* is grown to a cell density of $A_{600}$ of 1 to 2 for inoculation. The immature embryos and embryogenic calli maintained on the CM4C medium are transferred into an *A. tumefaciens* cell suspension in Petri dishes. The inoculation is conducted at 23 to 25° C. for 3 hours in the dark. After inoculation, the *A. tumefaciens* cells are removed and the explants are placed on semisolid medium (Gelrite) with liquid CM4C with full-strength MS salts and supplemented with 10 g/L glucose and 200 μM acetosyringone. The co-cultivation is performed at 24 to 26° C. in the dark for 2 or 3 days. After co-culture, the infected immature embryos and calli are cultured on the solid CM4C medium with 250 mg/L carbenicillin for 2 to 5 days without selection. *A. tumefaciens* infected explants are then transferred to CM4C medium supplemented with 3 mg/l glufosinate and 250 mg/L carbenicillin for callus induction. Two weeks later, the explants are transferred to the first regeneration medium, MMS0.2C (consisting of MS salts and vitamins, 1.95 g/L MES, 0.2 mg/L 2,4-dichloro-phenoxyacetic acid, 100 mg/L ascorbic acid, and 40 g/L maltose, solidified by 2 g/L gelrite supplemented with 3 mg/l glufosinate and 250 mg/L carbenicillin). At transfer to the regeneration medium, each piece of callus derived from one immature embryo or one piece of inoculated callus is divided into several small pieces (approximately 2 mm). In another 2 weeks, young shoots and viable callus tissues are transferred to the second regeneration medium, MMSOC, which contains the same components as MMS0.2C, with all antibiotics included. When the shoots develop into about 3 cm or longer plantlets, they are transferred to larger culture vessels containing the regeneration medium for further growth and selection. Leaf samples are taken from some of the plantlets for PCR testing at this stage. Plants that are highly glufosinate resistant are transferred to soil. All of the plants derived from the same embryo or piece of callus are considered to be clones of a given event.

The plants are then grown and selected for using PCR to detect the presence of the MtDef5 gene or cDNA. The expression of the MtDef5 gene or cDNA at the RNA level is determined using the qRT-PCR assay, and expression of the MtDef5 protein is determined by sandwich ELISA using a MtDef5 polyclonal antibody. Homozygotes are eventually selected using quantitative PCR using the Promega GoTaq® qPCR master mix (Promega Corporation, Madison, WI) on an AB StepOne Plus-Real time PCR system (Applied Biosystems, Carlsbad, CA) per the manufacturer's instructions.

Transgenic plants that are homozygous for the MtDef5 DNA construct insertion will be obtained, identified, and subsequently tested for resistance to *Fusarium* head blight as described in Chen et al. (1999) *Theor. Appl. Genet.* 99:755-760; leaf rust and stripe rust as described in Cheng et al. (2010) *Theor. Appl. Genet.* 121:195-204); and stem rust as described in Nirmala et al. (2011) *PNAS* 108:14676-14681.

Example 5

In Vitro Antifungal Activity of Chemically Synthesized MtDef5.1a Gamma Core Peptide with C-Terminal Extension (GMA-5C) (GACHRQGFGFACFCYKKC (SEQ ID NO:58))

In order to determine if a small peptide derived from the full-length MtDef5 protein exhibits antifungal activity, a peptide consisting of the C-terminal 18 amino acids is obtained from Genemed, Inc., Texas, and tested for its antifungal activity against *Fusarium graminearum* PH-1. This peptide contains the gamma-core motif and the last 6 amino acids of the mature MtDef5 protein.

Figure 3:
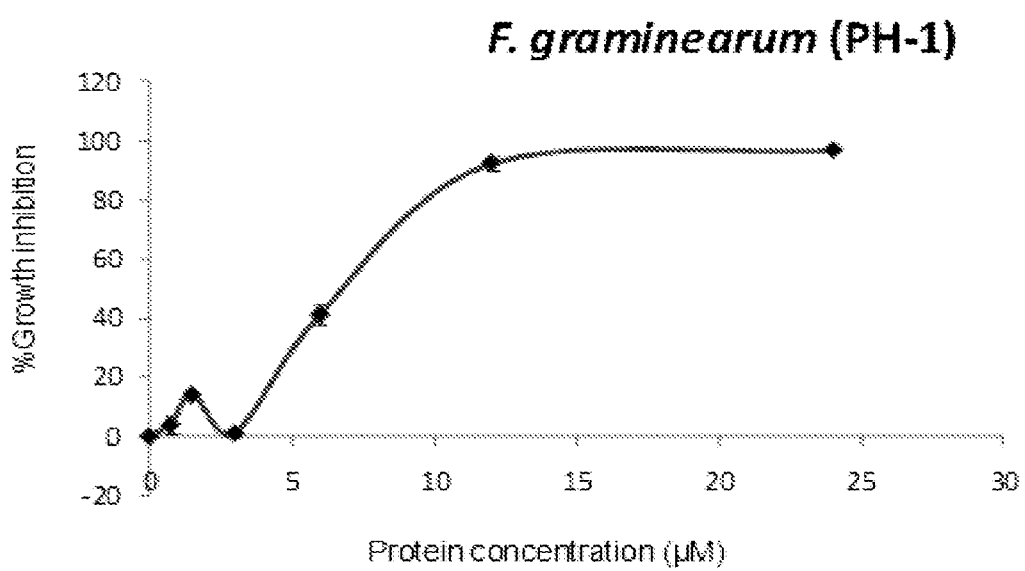
FIG. 3 shows the quantitative assessment of the in vitro antifungal activity of the chemically synthesized GMA-5C peptide GACHRQGFGFACFCYKKC (SEQ ID NO:58) of MtDef5.1a at 24 h after incubation of *Fusarium graminearum* PH-1 conidia with the peptide. Values are means of thee replications. Error bars indicate standard deviations. The in vitro antifungal activity of the peptide was determined as previously described (Ramamoorthy et al. (2007) *Cellular Microbiology* 9:1491-1506).

The antifungal activity of the gamma-core motif of MtDef5.1a is assessed using the chemically synthesized GMA-5C peptide having the amino acid sequence GACH-RQGFGFACFCYKKC (SEQ ID NO:58). Quantitative assessment of the in vitro antifungal activity of the chemically synthesized GMA-5C peptide is assessed at 24 h after incubation of *Fusarium graminearum* PH-1 conidia with the peptide as described in Ramamoorthy et al. (2007) *Cellular Microbiology* 9:1491-1506. The results are shown in FIG. 3, where the values reported are means of thee replications. Error bars indicate standard deviations.

The data demonstrate that the $IC_{50}$ (concentration required for 50% inhibition of fungal growth) of this peptide is about 6-12 µM, while the $IC_{100}$ (concentration required for 100% inhibition of fungal growth) is about 24 µM.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Amino Acid and Nucleotide Sequence Information

```
Medicago truncatula MtDef5.1a-MtDef5.6 defensin proprotein
amino acid sequences, comprising a MtDef5 signal peptide
(8-29 amino acids, underlined) and a mature
MtDef5 defensin protein (approximately 50 amino acids),
with the γ-core motif of each MtDef5 defensin shown in
bold, italic, 10 point type
MtDef5.1a:
SEQ ID NO: 1
MTSSASKFYTIFIFVCLAFLFISTSEVEAKLCQKRSTTWSGPCLNTGNCKRQCINVEHATFGACHRQGFGFACFCYKKC MtDef5.1a-MtDef5.1b "linker sequence":
SEQ ID NO: 2
APKKVEP MtDef5.1b:
SEQ ID NO: 3
KLCERRSKTWSGPCLISGNCKRQCINVEHATSGACHRQGIGFACFCKKKC MtDef5.1a-"linker"-MtDef5.1b:
SEQ ID NO: 4
MTSSASKFYTIFIFVCLAFLFISTSEVEAKLCQKRSTTWSGPCLNTGNCKRQCINVEHATF GACHRQGFGFAC FCYKKC

APKKVEPKLCERRSKTWSGPCLISGNCKRQCINVEHATSGACHRQGIGFACFCKKKC

MtDef5.2:
SEQ ID NO: 5
MASSSPKLFTIFLFLILVVLLFSTSEVQAKLCRGRSKLWSGPCINSKCKRQCINVERAVS GGCHLDNTGVFC FCDFKC

MtDef5.3:
SEQ ID NO: 6
MTSSATKFYTIFVFVCLALLLISICEVEAKVCQKRSKTWSGPCLNTGNCKRQCVDVENATF GACHRQGYGFAC FCYKKC
```

-continued

MtDef5.4:
SEQ ID NO: 7
MASSTLKFNTIFLFLSLALLLFFTLEVQGNICKRKSTTWSGPCLNTGNCKNQCINVEHATF*GACHQDGFGFAC*FCYFNC

MtDef5.5:
SEQ ID NO: 8
<u>MASSALKYYTFFLFFILALILLPTLEVQG</u>NTCQRKSKTWSGPCLNTANCKNQCISKEPPATF*GACHRDGIGFAC*FCYFNC

MtDef5.6:
SEQ ID NO: 9
MVCTEVQAKLCRGRSKLWSGPCINSKCKRQCINVERAVS*GGCHLDNTGVFC*FCDFKC
*Medicago truncatula* MtDef5.1a-MtDef5.6 proprotein cDNA
coding sequences, comprising a MtDef5 signal peptide
(8-29 amino acids) coding sequence (underlined),
and a mature MtDef5 protein (approximately 50 amino
acids) coding sequence, with the γ-core motif coding
sequence shown in bold type
MtDef5.1a and MtDef5.1b cDNA (SEQ ID NO: 10).
The nucleotide sequence shown in
bold, italics, and underlined encodes "linker"
peptide amino acid sequence APKKVEP:
<u>ATGACTTCCTCTGCTAGTAAATTCTATACCATCTTCATTTTTGTCTGCCTTGCCTTTCTCTTTATTTC</u>

<u>CACATCTGAGGTGGAAGCAAAACTTTGTCAAAAGCGAAGTACAACATGGTCAGGACCTTGTCTTAACA</u>

CAGGAAACTGCAAAAGACAATGCATTAATGTGGAGCATGCTACTTTTGGTGCTTGTCATCGTCAAGGC

TTTGGTTTTGCTTGCTTCTGCTACAAAAAATGT*GCTCCAAAGAAGGTGGAACCT*AAACTTTGTGAAAG

GCGAAGCAAAACATGGTCAGGACCTTGTCTTATCTCAGGAAATTGTAAAAGACAGTGCATCAATGTTG

AGCATGCAACTTCTGGTGCTTGTCACCGTCAAGGCATTGGTTTTGCTTGCTTCTGCAAGAAAAAATGT

TGA

MtDef5.2 cDNA (SEQ ID NO: 11):
<u>ATGGCTTCCTCTTCTCCTAAATTGTTTACCATCTTTCTGTTTCTCATCCTTGTCGTGCTCCTTTTCTC</u>

<u>AACTTCGGAGGTGCAAGCAAAACTTTGTAGAGGGAGAAGCAAACTTTGGTCAGGGCCTTGTATTAACT</u>

CAAAATGCAAAAGACAATGCATCAACGTGGAGCGCGCAGTTAGCGGGGGTTGTCACCTTGATAACACT

GGAGTTTTTTGTTTCTGCGACTTCAAATGCTGA

MtDef5.3 cDNA (SEQ ID NO: 12):
<u>ATGACTTCCTCTGCTACTAAATTTTACACCATCTTTGTTTTTGTCTGCCTTGCCCTTCTCCTTATTTC</u>

<u>CATATGTGAGGTGGAAGCAAAAGTGTGTCAAAAACGAAGTAAAACGTGGTCAGGACCTTGTCTTAACA</u>

CAGGAAACTGTAAAAGACAATGCGTTGATGTGGAGAATGCAACCTTCGGTGCTTGTCACCGTCAAGGC

TATGGTTTTGCTTGCTTCTGCTACAAAAAGTGTTGA

MtDef5.4 cDNA (SEQ ID NO: 13):
<u>ATGGCTTCATCTACTCTTAAATTCAACACTATCTTTCTGTTTCTCAGCCTTGCACTTCTCCTGTTCTT</u>

<u>CACATTGGAGGTACAAGGAAATATTTGTAAAAGGAAAAGCACAACATGGTCAGGGCCATGTTTAAACA</u>

CGGGAAACTGTAAAAATCAGTGCATCAATGTGGAACATGCTACTTTTGGGGCATGCCACCAAGATGGA

TTTGGATTTGCTTGCTTCTGCTACTTCAATTGCTGA

MtDef5.5 cDNA (SEQ ID NO: 14):
<u>ATGGCTTCCTCTGCTCTTAAATACACACTTTCTTTCTGTTTTTCATCCTTGCACTTATCCTGTTACC</u>

<u>CACATTGGAGGTACAAGGAAATACTTGTCAAAGGAAAAGCAAACATGGTCAGGGCCATGTTTAAACA</u>

CGGCAAACTGTAAAAATCAGTGCATCAGTAAGGAACCACCGGCAACATTTGGGGCATGTCACCGTGAT

GGCATTGGATTTGCTTGCTTCTGTTACTTCAACTGCTAA

MtDef5.6 cDNA (SEQ ID NO: 15):
<u>ATGGTGTGTACAGAGGTGCAAGCAAAACTTTGTAGAGGGAGAAGCAAACTTTGGTCAGGGCCTTGTAT</u>

TAACTCAAAATGCAAAAGACAATGCATCAACGTGGAGCGCGCAGTTAGCGGGGGTTGTCACCTTGATA

ACACTGGAGTTTTTTGTTTCTGCGACTTCAAATGCTGA

Mature *Medicago truncatula* MtDef5.1a-MtDef5.6
Defensin Protein Amino Acid Sequences
MtDef5.1a:
SEQ ID NO: 16
KLCQKRSTTWSGPCLNTGNCKRQCINVEHATFGACHRQGFGFACFCYKKC MtDef5.1b:
SEQ ID NO: 17
KLCERRSKTWSGPCLISGNCKRQCINVEHATSGACHRQGIGFACFCKKKC MtDef5.2:
SEQ ID NO: 18
KLCRGRSKLWSGPCINSKCKRQCINVERAVSGGCHLDNTGVFCFCDFKC MtDef5.3:
SEQ ID NO: 19
KVCQKRSKTWSGPCLNTGNCKRQCVDVENATFGACHROGYGFACFCYKKC MtDef5.4:
SEQ ID NO: 20
NICKRKSTTWSGPCLNTGNCKNQCINVEHATFGACHQDGFGFACFCYFNC MtDef5.5:
SEQ ID NO: 21
NTCQRKSKTWSGPCLNTANCKNQCISKEPPATFGACHRDGIGFACFCYFNC MtDef5.6:
SEQ ID NO: 22
KLCRGRSKLWSGPCINSKCKRQCINVERAVSGGCHLDNTGVFCFCDFKC Mature *Medicago truncatula* MtDef5.1a-MtDef5.6 Defensin
Protein cDNA Coding Sequences
MtDef5.1a:
SEQ ID NO: 23
AAACTTTGTCAAAAGCGAAGTACAACATGGTCAGGACCTTGTCTTAACACAGGAAACTGCAAAAGACA

ATGCATTAATGTGGAGCATGCTACTTTTGGTGCTTGTCATCGTCAAGGCTTTGGTTTTGCTTGCTTCT

GCTACAAAAAATGT

MtDef5.1b:
SEQ ID NO: 24
AAACTTTGTGAAAGGCGAAGCAAAACATGGTCAGGACCTTGTCTTATCTCAGGAAATTGTAAAAGACA

GTGCATCAATGTTGAGCATGCAACTTCTGGTGCTTGTCACCGTCAAGGCATTGGTTTTGCTTGCTTCT

GCAAGAAAAAATGT

MtDef5.2:
SEQ ID NO: 25
AAACTTTGTAGAGGGAGAAGCAAACTTTGGTCAGGGCCTTGTATTAACTCAAAATGCAAAAGACAATG

CATCAACGTGGAGCGCGCAGTTAGCGGGGGTTGTCACCTTGATAACACTGGAGTTTTTTGTTTCTGCG

ACTTCAAATGC

MtDef5.3:
SEQ ID NO: 26
AAAGTGTGTCAAAAACGAAGTAAAACGTGGTCAGGACCTTGTCTTAACACAGGAAACTGTAAAAGACA

ATGCGTTGATGTGGAGAATGCAACCTTCGGTGCTTGTCACCGTCAAGGCTATGGTTTTGCTTGCTTCT

GCTACAAAAAGTGT

MtDef5.4:
SEQ ID NO: 27
AATATTTGTAAAAGGAAAAGCACAACATGGTCAGGGCCATGTTTAAACACGGGAAACTGTAAAAATCA

GTGCATCAATGTGGAACATGCTACTTTTGGGGCATGCCACCAAGATGGATTTGGATTTGCTTGCTTCT

GCTACTTCAATTGC

MtDef5.5:
SEQ ID NO: 28
AATACTTGTCAAAGGAAAAGCAAAACATGGTCAGGGCCATGTTTAAACACGGCAAACTGTAAAAATCA

GTGCATCAGTAAGGAACCACCGGCAACATTTGGGGCATGTCACCGTGATGGCATTGGATTTGCTTGCT

TCTGTTACTTCAACTGC

-continued

MtDef5.6:
SEQ ID NO: 29
AAACTTTGTAGAGGGAGAAGCAAACTTTGGTCAGGGCCTTGTATTAACTCAAAATGCAAAAGACAATG

CATCAACGTGGAGCGCGCAGTTAGCGGGGGTTGTCACCTTGATAACACTGGAGTTTTTTGTTTCTGCG

ACTTCAAATGC

MtDef5.1a-5.6 Signal Peptide Amino Acid Sequences

MtDef5.1a-5.1b Signal Peptide Sequence:
MTSSASKFYTIFIFVCLAFLFISTSEVEA (SEQ ID NO: 30)

MtDef5.2 Signal Peptide Sequence:
MASSSPKLFTIFLFLILVVLLFSTSEVQA (SEQ ID NO: 31)

MtDef5.3 Signal Peptide Sequence:
MTSSATKFYTIFVFVCLALLLISICEVEA (SEQ ID NO: 32)

MtDef5.4 Signal Peptide Sequence:
MASSTLKFNTIFLFLSLALLLFFTLEVQG (SEQ ID NO: 33)

MtDef5.5 Signal Peptide Sequence:
MASSALKYYTFFLFFILALILLPTLEVQG (SEQ ID NO: 34)

MtDef5.6 Putative Signal Peptide Sequence:
MVCTEVQA (SEQ ID NO: 35)

MtDef5.1a-5.6 Signal Peptide cDNA Coding Sequences

MtDef5.1a-5.1b Signal Peptide cDNA Coding Sequence:
ATGACTTCCTCTGCTAGTAAATTCTATACCATCTTCATTTTTGTCTGCCTTGCCTTTCTCTTTATTTC

CACATCTGAGGTGGAAGCA
(SEQ ID NO: 36)

MtDef5.2 Signal Peptide cDNA Coding Sequence:
ATGGCTTCCTCTTCTCCTAAATTGTTTACCATCTTTCTGTTTCTCATCCTTGTCGTGCTCCTTTTCTC

AACTTCGGAGGTGCAAGCA (SEQ ID NO: 37)

MtDef5.3 Signal Peptide cDNA Coding Sequence:
ATGACTTCCTCTGCTACTAAATTTTACACCATCTTTGTTTTTGTCTGCCTTGCCCTTCTCCTTATTTC

CATATGTGAGGTGGAAGCA (SEQ ID NO: 38)

MtDef5.4 Signal Peptide cDNA Coding Sequence:
ATGGCTTCATCTACTCTTAAATTCAACACTATCTTTCTGTTTCTCAGCCTTGCACTTCTCCTGTTCTT

CACATTGGAGGTACAAGGA
(SEQ ID NO: 39)

MtDef5.5 Signal Peptide cDNA Coding Sequence:
ATGGCTTCCTCTGCTCTTAAATACTACACTTTCTTTCTGTTTTTCATCCTTGCACTTATCCTGTTACC

CACATTGGAGGTACAAGGA
(SEQ ID NO: 40)

MtDef5.6 Signal Peptide cDNA Coding Sequence:
ATGGTGTGTACAGAGGTGCAAGCA (SEQ ID NO: 41)

MtDef4.1-4.3 and Other Signal Peptide Amino Acid Sequences

MtDef4.1(H33R) Signal Peptide Sequence:
MARSVPLVSTIFVFLLLLVATGPSMVAEA (SEQ ID NO: 42)

MtDef4.2 Signal Peptide Sequence:
MARSVPLVSTIFVFFLLIVATEMGPSMVAA (SEQ ID NO: 43)

MtDef4.3 Signal Peptide Sequence:
MARSVPLVSTIFVFFLLLVATEMGPIMVAEA (SEQ ID NO: 44)

AL385796 Signal Peptide Sequence:
MARSVFLVSTIFVFLLVLVATGPSMVAEA (SEQ ID NO: 45)

AW573770 Signal Peptide Sequence:
MARSVSLVFTIFVFLLLVVATGPSMVAEA (SEQ ID NO: 46)

BE999096 Signal Peptide Sequence:
MARSVPLVSTIFVFLLLLVATGPSMVGEA (SEQ ID NO: 47)

MtDef4 Signal Peptide Consensus Sequence:
MARSVPLVSTIFVFLLLLVATGPSMVAEA (SEQ ID NO: 48)

MsDef1, MtDef4, and MtDef5.1a-5.6 γ-Core Motif (GXCX$_{3-9}$C)
(SEQ ID NO: 81) Peptide Amino Acid Sequences
MsDef1: GRCRDDFRC (SEQ ID NO: 49)

MtDef4: GRCRGFRRRC (SEQ ID NO: 50)

MtDef5.1a: GACHROGFGFAC (SEQ ID NO: 51)

MtDef5.1b: GACHRQGIGFAC (SEQ ID NO: 52)

MtDef5.2: GGCHLDNTGVFC (SEQ ID NO: 53)

MtDef5.3: GACHROGYGFAC (SEQ ID NO: 54)

MtDef5.4: GACHQDGFGFAC (SEQ ID NO: 55)

MtDef5.5: GACHRDGIGFAC (SEQ ID NO: 56)

MtDef5.6: GGCHLDNTGVFC (SEQ ID NO: 57)

MtDef5.1a-5.6 γ Core Peptides With C-Terminal Extensions (GMA-5C)

MtDef5.1a: GACHRQGFGFACFCYKKC (SEQ ID NO: 58)

MtDef5.1b: GACHRQGIGFACFCKKKC (SEQ ID NO: 59)

MtDef5.2: GGCHLDNTGVFCFCDFKC (SEQ ID NO: 60)

MtDef5.3: GACHROGYGFACFCYKKC (SEQ ID NO: 61)

MtDef5.4: GACHQDGFGFACFCYFNC (SEQ ID NO: 62)

MtDef5.5: GACHRDGIGFACFCYFNC (SEQ ID NO: 63)

MtDef5.6: GGCHLDNTGVFCFCDFKC (SEQ ID NO: 64)

MtDef5.1a-5.6 γ-Core Motif (GXCX$_{3-9}$C) Peptide Amino Acid
Sequence cDNA Coding Sequences
MtDef5.1a: GGTGCTTGTCATCGTCAAGGCTTTGGTTTTGCTTGC (SEQ ID NO: 65)

MtDef5.1b: GGTGCTTGTCACCGTCAAGGCATTGGTTTTGCTTGC (SEQ ID NO: 66)

MtDef5.2: GGGGGTTGTCACCTTGATAACACTGGAGTTTTTTGT (SEQ ID NO: 67)

MtDef5.3: GGTGCTTGTCACCGTCAAGGCTATGGTTTTGCTTGC (SEQ ID NO: 68)

MtDef5.4: GGGGCATGCCACCAAGATGGATTTGGATTTGCTTGC (SEQ ID NO: 69)

MtDef5.5: GGGGCATGTCACCGTGATGGCATTGGATTTGCTTGC (SEQ ID NO: 70)

MtDef5.6: GGGGGTTGTCACCTTGATAACACTGGAGTTTTTTGT (SEQ ID NO: 71)

MtDef5.1a-5.6 γ Core Peptide With C-Terminal
Extensions (GMA-5C) cDNA Coding Sequences
MtDef5.1a:
(SEQ ID NO: 72)
GGTGCTTGTCATCGTCAAGGCTTTGGTTTTGCTTGCTTCTGCTACAAAAAATGT MtDef5.1b:
(SEQ ID NO: 73)
GGTGCTTGTCACCGTCAAGGCATTGGTTTTGCTTGCTTCTGCAAGAAAAAATGT MtDef5.2:
(SEQ ID NO: 74)
GGGGGTTGTCACCTTGATAACACTGGAGTTTTTTGTTTCTGCGACTTCAAATGC MtDef5.3:
(SEQ ID NO: 75)
GGTGCTTGTCACCGTCAAGGCTATGGTTTTGCTTGCTTCTGCTACAAAAAGTGT MtDef5.4:
(SEQ ID NO: 76)
GGGGCATGCCACCAAGATGGATTTGGATTTGCTTGCTTCTGCTACTTCAATTGC -continued MtDef5.5:
(SEQ ID NO: 77)
GGGGCATGTCACCGTGATGGCATTGGATTTGCTTGCTTCTGTTACTTCAACTGC MtDef5.6:
(SEQ ID NO: 78)
GGGGGTTGTCACCTTGATAACACTGGAGTTTTTTGTTTCTGCGACTTCAAATGC

NON-PATENT PUBLICATIONS CITED

Various patent and non-patent publications are cited herein, the disclosures of each of which are incorporated herein by reference in their entirety.

Bent A F, Kunkel B N, Dahlbeck D, Brown K L, Schmidt R, Giraudat J, Leung J, Staskawicz B J. (1994) RPS2 of *Arabidopsis thaliana*: a leucine-rich repeat class of plant disease resistance genes. Science 265(5180):1856-60.

Broekaert, W. F., Terras, F. R., Cammue, B. P., and Vanderleyden, J. (1990). An automated quantitative assay for fungal growth inhibition. FEMS Microbiology Letters 69, 55-60.

Broekaert, W. F., Terras, F. R., Cammue, B. P., and Osborn, R. W. (1995). Plant defensins: novel antimicrobial peptides as components of the host defense system. Plant Physiol 108, 1353-1358.

Broekaert, W. F., Cammue, B. P. A., De Bolle, M. F. C., Thevissen, K., De Samblanx, G. W., and Osborn, R. W. (1997). Antimicrobial peptides from plants. Critical Reviews in Plant Sciences 16, 297-323.

Broothaerts W, Mitchell H J, Weir B, Kaines S, Smith L M, Yang W, Mayer J E, Roa-Rodriguez C, Jefferson R A. 2005. Gene transfer to plants by diverse species of bacteria. 2005. Nature. 433(7026):629-33.

Bustin, S. A. Quantification of mRNA using real-time reverse transcription PCR (RT-PCR): trends and problems. Journal of Molecular Endocrinology (2002) 29, 23-39.

Callis, J, Fromm, M, Walbot, V. (1987) Introns increase gene expression in cultured maize cells. Genes Dev. 1987 December; 1(10):1183-200.

Cappelini, R. A., and Peterson, J. L. (1965). Macroconidium formation in submerged cultures by a non-sporulating strain of Gibberella zeae. Mycologia 57, 962-966.

Cazzonnelli, C. I. and J. Velten. (2003) Construction and Testing of an Intron-Containing Luciferase Reporter Gene From Renilla reniformis. Plant Molecular Biology Reporter 21: 271-280.

Collier, R., B. Fuchs, N. Walter, W. K. Lutke, and C. G. Taylor. (2005) Ex vitro composite plants: an inexpensive, rapid method for root biology. Plant J 43: 449-457.

Correll, J. C., Klittich, C. J. R., and Leslie, J. F. (1987). Nitrate nonutilizing mutants of *Fusarium graminearum* and their use in vegetative compatibility tests. Phytopathology 77, 1640-1646.

da Silva Conceicao, A., and Broekaert, W. F. (1999). Plant Defensins. In Pathogenesis-related proteins in plants, S. Muthukrishnan, ed (New York: CRC Press), pp. 247-260.

Doyle J J, Schuler M A, Godette W D, Zenger V, Beachy R N, Slightom J L. (1986) The glycosylated seed storage proteins of Glycine max and Phaseolus vulgaris. Structural homologies of genes and proteins. J Biol Chem. 261(20):9228-38.

Frame, B. R., Shou, H., Chikwamba, R. K., Zhang, Z., Xiang C., Fonger, T. M., Pegg S E, Li B, Nettleton D S, Pei D, and Wang K. (2002) *Agrobacterium tumefaciens*-mediated transformation of maize embryos using a standard binary vector system. Plant Physiol. 129(1):13-22.

Gao, A., Hakimi, S. M., Mittanck, C. A., Wu, Y., Woerner, M. B., Stark, D. M., Shah, D. M., Liang, J., and Rommens, C. M. T. (2000). Fungal pathogen protection in potato by expression of a plant defensin peptide. Nature Biotechnology 18, 1307-1310.

Grant M R, Godiard L, Straube E, Ashfield T, Lewald J, Sattler A, Imes R W, Dangl, J L. (1995) Structure of the *Arabidopsis* RPM1 gene enabling dual specificity disease Resistance Science. 269(5225):843-6.

Hammond-Kosack, K. E., Urban, M., Baldwin, T., Daudi, A., Rudd, J. J., Keon, J., Lucas, J. A., Maguire, K., Komyukhin, D., Jing, H.-C., Bass, C., and Antoniw, J. (2004). 4th International Crop Science Congress. In New directions for a diverse planet, T. Fischer, Turner, N., Angus, J., McIntyre, L., Robertson, M., Borrell, A., Lloyd, D., ed (Brisbane, Australia: The Regional Institute, Ltd, Gosford, Austraila).

Hanks, J. N., Snyder, A. K., Graham, M. A., Shah, R. K., Blaylock, L. A., Harrison, M. J., and Shah, D. M. (2005). Defensin gene family in *Medicago truncatula*: structure, expression and induction by signal molecules. Plant Mol Biol 58, 385-399.

Horsch, R. B., J. E. Fry, N. Hoffman et al. (1985) A simple and general method for transferring genes into plants. Science. 227: 1229-1231

Kingsman S M, Kingsman A J, Dobson M J, Mellor J, Roberts N A. (1985) Heterologous gene expression in *Saccharomyces cerevisiae*. Biotechnol Genet Eng Rev. 3:377-416.

Koehler S M, and Ho, TH. (1990) Hormonal regulation, processing, and secretion of cysteine proteinases in barley aleurone layers. Plant Cell. (8):769-83.

Lam E, and Chua N H. (1991) Tetramer of a 21-base pair synthetic element confers seed expression and transcriptional enhancement in response to water stress and abscisic acid. J Biol Chem. 1991 Sep. 15; 266(26):17131-5.

Lay, F. T., and Anderson, M. A. (2005). Defensins—components of the innate immune system in plants. Curr Protein Pept Sci 6, 85-101.

Liang, J., Shah, D. M., Wu, Y., Rosenberger, C. A., and Hakimi, S. M. U.S. Pat. No. 6,916,970 for Transgenic plants comprising antifungal polypeptides from alfalfa and methods for controlling plant pathogenic fungi; issued Jul. 12, 2005.

Mankin, S. L, G. C. Allen, and W. F. Thompson. 1997. Introduction of a Plant Intron into the Luciferase Gene of Photinus Pyralis. Plant Mol Biol Rep 15(2): 186-196.

McElroy, D, Zhang W, Cao J, Wu R. 1990. Isolation of an efficient actin promoter for use in rice transformation. The Plant Cell, Vol. 2, 163-171

Reiser G, Glumoff V, Kalin M, Ochsner U. (1990) Transfer and expression of heterologous genes in yeasts other than *Saccharomyces cerevisiae*. Adv Biochem Eng Biotechnol.; 43:75-102.

Sambrook, J., and Russell, D. W. (2001). Molecular Cloning: A Laboratory Manual. (Cold Sprong Harbor Laboratory Press, Cold Sprong Harbor, New York).

Seong, K., Hou, Z., Tracy, M., Kistler, H. C., and Xu, J.-R. (2005). Random insertional mutagensis identifies genes associated with virulence in the wheat scab fungus *Fusarium graminearum*. Phytopathology 95, 744-750.

Sidorov, V, Gilbertson, L, Addae, P, and Duncan, D. (2006) *Agrobacterium*-mediated transformation of seedling-derived maize callus. Plant Cell Rep. 2006 April; 25(4):320-8. (Epub 2005 Oct. 27)

Spelbrink, R. G., Dilmac, N., Allen, A., Smith, T. J., Shah, D. M., and Hockerman, G. H. (2004). Differential antifungal and calcium channel-blocking activity among structurally related plant defensins. Plant Physiol 135, 2055-2067.

Terras, F. R., Schoofs, H. M., De Bolle, M. F., Van Leuven, F., Rees, S. B., Vanderleyden, J., Cammue, B. P., and Broekaert, W. F. (1992). Analysis of two novel classes of plant antifungal proteins from radish (Raphanus sativus L.) seeds. J Biol Chem 267, 15301-15309.

Thevissen, K., Francois, I. E., Aerts, A. M., and Cammue, B. P. (2005). Fungal sphingolipids as targets for the development of selective antifungal therapeutics. Curr Drug Targets 6, 923-928.

Thevissen, K., Ghazi, A., De Samblanx, G. W., Brownlee, C., Osborn, R. W., and Broekaert, W. F. (1996). Fungal membrane responses induced by plant defensins and thionins. J Biol Chem 271, 15018-15025.

Thevissen, K., Cammue, B. P., Lemaire, K., Winderickx, J., Dickson, R. C., Lester, R. L., Ferket, K. K., Van Even, F., Parret, A. H., and Broekaert, W. F. (2000). A gene encoding a sphingolipid biosynthesis enzyme determines the sensitivity of *Saccharomyces cerevisiae* to an antifungal plant defensin from dahlia (*Dahlia merckii*). Proc Natl Acad Sci USA 97, 9531-9536.

Thevissen, K., Warnecke, D. C., Francois, I. E., Leipelt, M., Heinz, E., Ott, C., Zahringer, U., Thomma, B. P., Ferket, K. K., and Cammue, B. P. (2004). Defensins from insects and plants interact with fungal glucosylceramides. J Biol Chem 279, 3900-3905.

Thomma, B. P., Cammue, B. P., and Thevissen, K. (2003). Mode of action of plant defensins suggests therapeutic potential. Curr Drug Targets Infect Disord 3, 1-8.

Thomma, B. P. H. J., Cammue, B. P. A., and Thevissen, K. (2002). Plant defensins. Planta 216, 193-202.

Using Antibodies: A Laboratory Manual. (1999). Ed. Harlow and Lane. Cold Spring Harbor Laboratory Press.

Vasil V, Clancy M, Ferl R J, Vasil I K, Hannah L C. (1989) Increased Gene Expression by the First Intron of Maize Shrunken-1 Locus in Grass Species. Plant Physiol. 1989 December; 91(4):1575-1579.

Wesley S V, Helliwell C A, Smith N A, Wang M B, Rouse D T, Liu Q, Gooding P S, SinghSP, Abbott D, Stoutjesdijk P A, Robinson S P, Gleave A P, Green A G, Waterhouse P M. (2001). Construct design for efficient, effective and high-throughput gene silencing in plants. Plant J. 27(6): 581-590.

---

What is claimed is:

1. A polynucleotide comprising a nucleic acid fragment that encodes an antifungal protein comprising an amino acid sequence having at least 95% sequence identity to the amino acid sequence of SEQ ID NO: 16 or SEQ ID NO: 17, wherein the amino acid residues corresponding to the defensin gamma core amino acid sequence at residues 33 to 44 of SEQ ID NO: 16 or SEQ ID NO: 17 comprise the amino acid sequences of SEQ ID NO:51 or SEQ ID NO:52 and are unmodified, wherein any substitutions of other said amino acid residues of SEQ ID NO: 16 or SEQ ID NO: 17 are conservative amino acid residue substitutions, and wherein the nucleic acid fragment is operably linked to a heterologous promoter and to a translational initiation codon that is in frame with the nucleic acid fragment that encodes the antifungal protein.

2. The polynucleotide of claim 1, wherein the nucleic acid fragment further comprises a polynucleotide encoding a signal peptide which is operably linked to the polynucleotide which encodes the antifungal protein.

3. The polynucleotide claim 1, wherein the nucleic acid fragment is operably linked to a heterologous promoter that provides for expression of the nucleic acid fragment in a plant or in a yeast cell.

4. The polynucleotide of claim 1, wherein the antifungal protein comprises the amino acid sequence SEQ ID NO: 16 or SEQ ID NO: 17.

5. A yeast cell comprising the polynucleotide of claim 1.

6. The yeast cell of claim 5, wherein the yeast cell is selected from the group consisting of *Candida, Kluveromyces, Hansuela, Pichia, Saccharomyces, Schizosaccharomyces,* and *Yarrowia.*

7. A plant comprising the polynucleotide of claim 1.

8. The plant of claim 7, wherein the plant is selected from the group consisting of soybean, wheat, maize, sugarcane, rice, and potato.

* * * * *